(12) United States Patent
Belfield et al.

(10) Patent No.: US 7,285,399 B2
(45) Date of Patent: Oct. 23, 2007

(54) COMPOSITIONS AND METHODS USING THE YEAST YMR107W PROMOTER

(75) Inventors: Graham P Belfield, Loughborough (GB); Caroline Oakley, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/430,250

(22) Filed: May 9, 2006

(65) Prior Publication Data

US 2006/0211118 A1 Sep. 21, 2006

Related U.S. Application Data

(63) Continuation of application No. 11/239,107, filed on Sep. 30, 2005, now Pat. No. 7,067,282, which is a continuation of application No. 10/776,213, filed on Feb. 12, 2004, now Pat. No. 7,078,190, which is a continuation of application No. 09/743,194, filed on Jan. 8, 2001, now Pat. No. 6,716,601.

(51) Int. Cl.
| | |
|---|---|
| *C12N 15/00* | (2006.01) |
| *C12N 15/09* | (2006.01) |
| *C12N 1/19* | (2006.01) |
| *C07H 21/04* | (2006.01) |
| *C12P 21/00* | (2006.01) |

(52) U.S. Cl. .................... 435/69.1; 435/6; 435/29; 435/91.4; 435/91.41; 435/254.2; 435/320.1; 435/476; 536/24.1; 536/23.1

(58) Field of Classification Search ............ None
See application file for complete search history.

(56) References Cited

OTHER PUBLICATIONS

The Nucleotide Sequence of . . . ; M. Johnson et al., Nature, vol. 387, Supp. pp. 87-90 (1997).

Yeast Sequencing Reports, Sequence analysis of a 44 kb DNA . . . , M. Vandenbol et al., Yeast, vol. 11 pp. 1069-1075 (1995).

Yeast Sequencing Reports, Sequence Analysis of a 37 6 kbp Cosmid . . . , P. Verhasselt et al., Yeast, vol. 13, pp. 241-250 (1997).

B-Door-External, Terminal-4247-1.2.Log, pp. 5-8 (2000).

B-Door-External, Terminal-4247-4.Log, pp. 5-6 (2000).

B-Door-External, Terminal-4247-2.Log, pp. 3-5 (2000).

B-Door-External, Terminal-4247-3.Log, pp. 3-5 (2000).

Johnston, M., et al; "*Saccharomyces cerevisiae* chromosome XII cosmid 9354"; *Medline*; 97313267; B-Door-External, Terminal 4247-1-2.Log, pp. 5-8; Jul. 24, 2000; Aug. 13, 1997 (Rel. 52, Last Updated, Ver. 3).

Vandenbol, M., et al; "*S. cerevisiae* chromosome XV DNA (44 Kb fragment)"; *Medline*; 96076631; B-Door-External Terminal 4247-4.Log, pp. 5-6; Jul. 24, 2000; Mar. 24, 1997 (Rel. 51, Last Updated, Ver. 7).

Hunt, S., et al; "*S. cerevisiae* chromosome XIII cosmid 9920"; Unpublished; B-Door-External Terminal 4247-2.Log, pp. 3-5; Jul. 24, 2000; Submitted Mar. 10, 1995 to the EMBL/GenBank/DDBJ databases.

Hunt, S., et al; "*S. cerevisiae* chromosome XIII cosmid 9718"; Unpublished; B-Door-External Terminal 4247-3.Log; pp. 3-5; Jul. 24, 2000; Submitted May 19, 1995 to the EMBL/GenBank/DDBJ databases.

Goffeau, et al.; Science, 1996, vol. 274, pp. 546-567.

*Primary Examiner*—Nancy Vogel
(74) *Attorney, Agent, or Firm*—Nixon & Vanderhye

(57) ABSTRACT

The invention provides novel yeast promoters useful for controlling the expression of homologous and heterologous nucleic acid molecules in yeast cells. The yeast promoters are induced by a fermentable carbon source, such as glucose, or a non-fermentable carbon source, such as ethanol, or both. Therefore, expression of nucleic acid molecules encoding a polypeptide under the control of the novel yeast promoters may be regulated by varying the level of a fermentable carbon source, or a non-fermentable carbon source, or both.

15 Claims, 16 Drawing Sheets

Figure 13 YLR110C promoter region (SEQ ID NO:29)
Sequence shown: Chr XII 370650 to 370051 (reverse orientation)

```
                  ATGCAAGCTTCGCGGCCGC              YLR-F
  1    AGAACCAAAT GGGAAAATCG AATGGGTCC AGAACTGCTT TGAGTGCTGG
         TCTTGGTTTA CCCTTTTAGC CTTACCCAGG TCTTGACGAA ACTCACGACC

51    CTATTGGCGT CTGATTTCCG TTTGGGAAT CCTTGCCGC GCGCCCTCT
         GATAACCGCA GACTAAAGGC AAACCCTTA GGAACGGCG CGCGGGAGA

101    CAAACTCCG CACAAGTCCC AGAAAGCGGG AAAGAATAA AACGCCACCA
         GTTTGAGGC GTGTTCAGGG TCTTCGCCC TTTCTTATT TTGCGGTGGT

151    AAAAAAAAAA AATAAAGCC AATCCTCGAA GCGTGGGTGG TAGGCCCTGG
         TTTTTTTTTT TTATTTCGG TTAGGAGCTT CGCACCCACC ATCCGGGACC

201    ATTATCCCGT ACAAGTATTT CTCAGGAGTA AAAAAACCGT TTGTTTTGGA
         TAATAGGGCA TGTTCATAAA GAGTCCTCAT TTTTTGGCA AACAAAACCT

251    ATTCCCCATT TCGCGGCCAC CTACGCCGCT ATCTTTGCAA CAACTATCTG
         TAAGGGGTAA AGCGCCGGTG GATGCGGCGA TAGAAACGTT GTTGATAGAC

301    CGATAACTCA GCAAATTTTG CATATTCGTG TTGCAGTATT GCGATAATGG
         GCTATTGAGT CGTTTAAAAC GTATAAGCAC AACGTCATAA CGCTATTACC

351    GAGTCTTACT TCCAACATAA CGGCAGAAAG AAATGTGAGA AAATTTGCA
         CTCAGAATGA AGGTTGTATT GCCGTCTTTC TTTACACTCT TTTAAAACGT

401    TCCTTTGCCT CCGTTCAAGT ATATAAAGTC GGCATGCTTG ATAATCTTTC
         AGGAAACGGA GGCAAGTTCA TATATTTCAG CCGTACGAAC TATTAGAAAG

451    TTTCCATCCT ACATTGTTCT AATTATTCTT ATTCTCCTTT ATTCTTTCCT
         AAAGGTAGGA TGTAACAAGA TTAATAAGAA TAAGAGGAAA TAAGAAAGGA

501    AACATACCAA GAAATTAATC TTCTGTCATT CGCTAAACA CTATATCAAT
         TTGTATGGTT CTTTAATTAG AAGACAGTAA GCGAATTGT GATATACTTA
                                                    ← YLR-R          GT
551    AATGCAATTT TCTACTGTCG CTTCTATCGC CGCTGTCGCC GCTGTCGCTT
         TTACGTTAAA AGATGACAGC GAAGATAGCG GCGACAGCGG CGACAGCGAA
       A CCGGACC
```

YLR111W ORF = Underline

YLR110C ORF = Bold

YLR-F = SEQ ID NO:5

YLR-R = SEQ ID NO:6

Figure 14 YMR251WA promoter region (SEQ ID NO:30)

Sequence shown: CHR XIII 773951 TO 774800

```
              AGCTAAGCTTCGCGGCCGC                          YMR-F
  1   GCCACGGGTC AACCCGATTG GGATCACCCC ACTGGGCCC AAGCCTGATA
      CGGTGCCCAG TTGGGCTAAC CCTAGTGGGG TGACCCGGG TTCGGACTAT

51   TCCGACCTCC ATGAAATTTT TTTTTTTCTT TCGATTAGCA CGCACACACA
      AGGCTGGAGG TACTTTAAAA AAAAAAAGAA AGCTAATCGT GCGTGTGTGT

101   TCACATAGAC TGCGTCATAA AAATACACTA CGGAAAAACC ATAAAGAGCA
      AGTGTATCTG ACGCAGTATT TTTATGTGAT GCCTTTTGG TATTTCTCGT

151   AAGCGATACC TACTTGGAAG GAAAAGGAGC ACGCTTGTAA GGGGGATGGG
      TTCGCTATGG ATGAACCTTC CTTTTCCTCG TGCGAACATT CCCCCTACCC

201   GGCTAAGAAG TCATTCACTT TCTTTTCCCT TCGCGGTCCG GACCCGGGAC
      CCGATTCTTC AGTAAGTGAA AGAAAAGGGA AGCGCCAGGC CTGGGCCCTG

251   CCCTCCTCTC CCCGCACGAT TTCTTCCTTT CATATCTTCC TTTTATTCCT
      GGGAGGAGAG GGGCGTGCTA AAGAAGGAAA GTATAGAAGG AAAATAAGGA

301   ATCCCGTTGA AGCAACCGCA CTATGACTAA ATGGTGCTGG ACATCTCCAT
      TAGGGCAACT TCGTTGGCGT GATACTGATT TACCACGACC TGTAGAGGTA

351   GGCTGTGACT TGTGTGTATC TCACAGTGGT AACGGCACCG TGGCTCGGAA
      CCGACACTGA ACACACATAG AGTGTCACCA TTGCCGTGGC ACCGAGCCTT

401   ACGGTTCCTT CGTGACAATT CTAGAACAGG GGCTACAGTC TCGATAATAG
      TGCCAAGGAA GCACTGTTAA GATCTTGTCC CCGATGTCAG AGCTATTATC

451   AATAATAAGC GCATTTTTGC TAGCGCCGCC GCGGCGCCCG TTTCCCAATA
      TTATTATTCG CGTAAAAACG ATCGCGGCGG CGCCGCGGGC AAAGGGTTAT

501   GGGAGGCGCA GTTTATCGGC GGAGCTCTAC TTCTTCCTAT TTGGGTAAGC
      CCCTCCGCGT CAAATAGCCG CCTCGAGATG AAGAAGGATA AACCCATTCG

551   CCCTTTCTGT TTTCGGCCAG TGGTTGCTGC AGGCTGCGCC GGAGAACATA
      GGGAAAGACA AAAGCCGGTC ACCAACGACG TCCGACGCGG CCTCTTGTAT

601   GTGATAAGGG ATGTAACTTT CGATGAGAGA ATTAGCAAGC GGAAAAAAAC
      CACTATTCCC TACATTGAAA GCTACTCTCT TAATCGTTCG CCTTTTTTTG

651   TATGGCTAGC TGGGAGTTGT TTTCAATCA TATAAAAGGG AGAAATTGTT
      ATACCGATCG ACCCTCAACA AAAGTTAGT ATATTTTCCC TCTTTAACAA

701   GCTCACTATG TGACAGTTTC TGGGACGTCT TAACTTTTAT TGCAGAGGAC
      CGAGTGATAC ACTGTCAAAG ACCCTGCAGA ATTGAAAATA ACGTCTCCTG

751   TATCAAATCA TACAGATATT GTCAAAAAAA AAAAAGACTA ATAATAAAAA
      ATAGTTTAGT ATGTCTATAA CAGTTTTTTT TTTTTCTGAT TATTATTTTT
                                               ⤶ YMR-R     G A
801   ATGAAGTTAT CTCAAGTTGT TGTTTCCGCC GTCGCCTTCA CTGGTTTAGT
      TACTTCAATA GAGTTCAACA ACAAAGGCGG CAGCGGAAGT GACCAAATCA
                 C
```

YMR251W ORF = Underline
YMR251WA ORF = Bold
YMR-F = SEQ ID NO:7
YMR-R = SEQ ID NO:8

Figure 15 YMR107W PROMOTER REGION (SEQ ID NO:31)

Sequence shown: CHR XIII 482463 TO 483063

```
          1  AAAGAATCCA TCACTATTTG AAAAAAAGTC ATCTGGCACG TTTAATTATC
YMR107-F
AGCTAAGCTTCGCGGCCGC
         51  AGAGCAGAAA TGATGAAGGG TGTTAGCGCC GTCCACTGAT GTGCCTGGTA

101  GTCATGATTT ACGTATAACT AACACATCAT GAGGACGGCG GCGTCACCCC

151  AACGCAAAAG AGTGACTTCC CTGCGCTTTG CCAAACCCC ATACATCGCC

201  ATCTGGCTCC TGGCAGGGCG GTTGATGGAC ATCGCCGCC TCCCTTAATT

251  GCTAAAGCCT CCACAAGGCA CAATTAAGCA ATATTTCGGG AAAGTACACC

301  AGTCAGTTTG CGCTTTTATG ACTGGGTTCT AAGGTACTAG ATGTGAAGTA

351  GTGGTGACAG AATCAGGGAG ATAAGAGGGA GCAGGGTGGG GTAATGATGT

401  GCGATAACAA TCTTGCTTGG CTAATCACCC CCATATCTTG TAGTGAGTAT

451  ATAAATAGGA GCCTCCCTTC CTATTGCAAC TCCATAAAAT TTTTTTTGT
                                                       MODIFICATION AT
        501  AGCCACTTCT GTAACAAGAT AAATAAAACC AACTAATCGA GATATCAAAT
                                                       GATTAGCT CTATAGTGTA

551  ATGGGTAGTT TTTGGGACGC ATTCGCAGTA TACGACAAGA AAAAGCACGC
             TACCCTACCTA YMR107-R
```

YMR107W ORF = Bold
YMR107-F = SEQ ID NO:9
YMR107-R = SEQ ID NO:10

Figure 16 ZEO1 PROMOTER REGION (SEQ ID NO:32)

Sequence shown: CHR XV 109746 TO 110346

```
          1   TTCAGGAGTC TCTCGCGTTA GAGCAGTACG TGGCGCAGCT AAACTCGCCG
ZEO1-F
AGCTAAGCTTCGCGGCCGC
         51   GGAGGTCTGC TTCACGAGCG CGGTGTGCGC CTAGTATTGC CCCGACGGTC

101   CGGGTGCCTA TCCCTAGATT TCGTCGTGCC CCGACCCAAA TAGTTAAACG

151   TGTGGTTTAT GGGTGCACCA GGGCTTTATC GTGTTTTATA TCGATGGCGA

201   TTTGTGCCTC CAGTGTATTT TTGTATATCC AATTAAGGTT TCTTACCTAA

251   TTTTATTTTT ATCATCTTTA GTTAATGCTG GTTTGCTCTG TTTCTGCTGC

301   TTTCTGTGCG GTTCTCCTCT TCTCTTGTTT CTTCGTGTTG TCCCCCATCG

351   CCGATGGGCT TATATGGCGT ATATATATAG AGCGAGTTTT TACGTCGAAG

401   ATCATCTCAG TTTGCTTGAT AGCCTTTCTA CTTTATTACT TTCGTTTTTA

451   ACCTCATTAT ACTTTAGTTT TCTTTGATCG GTTTTTTTCT CTGTATACTT

501   AAAAGTTCAA ATCAAAGAAA CATACAAAAC TACGTTTATA TCAATTAATA
                                                  GCAAATAT AGTTAATGTA

551   ATGTCTGAAA TTCAAAACAA AGCTGAAACT GCCGCCCAAG ATGTCCAACA
              TACGCTAGCAT ZEO1-R
```

YOL110W ORF = Underline
ZEO1 (YOL109W) ORF = Bold
ZEO1-F = SEQ ID NO:11
ZEO1-R = SEQ ID NO:12

SEQUENCE LISTING

```
<160> NUMBER OF SEQ ID NOS: 32

<210> SEQ ID NO 1
<211> LENGTH: 494
<212> TYPE: DNA
<213> ORGANISM: Saccharomyces cerevisiae

<400> SEQUENCE: 1
cgtctgattt ccgttttggg aatcctttgc cgcgcgcccc tctcaaaact ccgcacaagt      60
cccagaaagc gggaaagaaa taaaacgcca ccaaaaaaaa aaaaataaaa gccaatcctc     120
gaagcgtggg tggtaggccc tggattatcc cgtacaagta tttctcagga gtaaaaaaac     180
cgtttgtttt ggaattcccc atttcgcggc cacctacgcc gctatctttg caacaactat     240
ctgcgataac tcagcaaatt ttgcatattc gtgttgcagt attgcgataa tgggagtctt     300
actcccaaca taacggcaga aagaaatgtg agaaaatttt gcatcctttg cctccgttca     360
agtatataaa gtcggcatgc ttgataatct ttctttccat cctacattgt tctaattatt     420
cttattctcc tttattcttt cctaacatac caagaaatta atcttctgtc attcgcttaa     480
acactatatc acat                                                       494

<210> SEQ ID NO 2
<211> LENGTH: 723
<212> TYPE: DNA
<213> ORGANISM: Saccharomyces cerevisiae

<400> SEQUENCE: 2
ctttcgatta gcacgcacac acatcacata gactgcgtca taaaaataca ctacggaaaa      60
accataaaga gcaaagcgat acctacttgg aaggaaaagg agcacgcttg taaggggggat    120 gggggctaag aagtcattca ctttcttttc ccttcgcggt ccggacccgg gacccctcct     180
ctccccgcac gatttcttcc tttcatatct tccttttatt cctatcccgt tgaagcaacc     240
```

```
gcactatgac taaatggtgc tggacatctc catggctgtg acttgtgtgt atctcacagt    300
ggtaacggca ccgtggctcg gaaacggttc cttcgtgaca attctagaac agggcacta    360 gtctcgataa tagaataata agcgcatttt tgctagcgcc gccgcggcgc ccgtttccca    420 ataggaggc gcagtttatc ggcggagctc tacttcttcc tatttgggta agccccttc     480 tgttttcggc cagtggttgc tgcaggctgc gccggagaac atagtgataa gggatgtaac    540
tttcgatgag agaattagca agcggaaaaa actatggct agctgggagt tgttttcaa     600 tcatataaaa gggagaaatt gttgctcact atgtgacagt ttctgggacg tcttaacttt    660
tattgcagag gactatcaaa tcatacagat attgtcaaaa aaaaaaaga ctaataataa    720 cat                                                                  723

<210> SEQ ID NO 3
<211> LENGTH: 497
<212> TYPE: DNA
<213> ORGANISM: Saccharomyces cerevisiae

<400> SEQUENCE: 3
gcagaaatga tgaagggtgt tagcgccgtc cactgatgtg cctggtagtc atgatttacg     60
tataactaac acatcatgag gacggcggcg tcaccccaac gcaaaagagt gacttccctg    120
cgctttgcca aaaccccata catcgccatc tggctcctgg cagggcggtt gatggacatc    180
agccgcctcc cttaattgct aaagcctcca caaggcacaa ttaagcaata tttcgggaaa    240
gtacaccagt cagtttgcgc ttttatgact gggttctaag gtactagatg tgaagtagtg    300
gtgacagaat cagggagata agaggggagca gggtggggta atgatgtgcg ataacaatct    360
tgcttggcta atcaccccca tatcttgtag tgagtatata aataggagcc tcccttccta    420
ttgcaactcc ataaaatttt tttttgtagc cacttctgta acaagataaa taaaaccaac    480
taatcgagat atcacat                                                   497

<210> SEQ ID NO 4
<211> LENGTH: 500
<212> TYPE: DNA
<213> ORGANISM: Saccharomyces cerevisiae

<400> SEQUENCE: 4
ggaggtctgc ttcacgagcg cggtgtgcgc ctagtattgc cccgacggtc cgggtgccta     60
tccctagatt tcgtcgtgcc ccgacccaaa tagttaaacg tgtggtttat gggtgcacca    120
gggctttatc gtgttttata tcgatggcga tttgtgcctc cagtgtattt ttgtatatcc    180
aattaaggtt tcttacctaa tttattttt atcatcttta gttaatgctg gtttgctctg    240
tttctgctgc tttctgtgcg gttctcctct tctcttgttt cttcgtgttg tccccccatcg    300 ccgatgggct tatatggcgt atatatatag agcgagtttt tacgtcgaag atcatctcag    360
tttgcttgat agccttccta ctttattact ttcgttttta acctcattat actttagttt    420
tctttgatcg gttttttttct ctgtatactt aaaagttcaa atcaaagaaa catacaaaac    480
tacgtttata tcaattacat                                                500

<210> SEQ ID NO 5
<211> LENGTH: 35
<212> TYPE: DNA
<213> ORGANISM: Saccharomyces cerevisiae

<400> SEQUENCE: 5
atgcaagctt cgcggccgcc gtctgatttc cgttt                                35
```

<210> SEQ ID NO 6
<211> LENGTH: 30
<212> TYPE: DNA
<213> ORGANISM: Saccharomyces cerevisiae

<400> SEQUENCE: 6
ccaggccgca tatgtcatat agtgtttaag                                              30

<210> SEQ ID NO 7
<211> LENGTH: 37
<212> TYPE: DNA
<213> ORGANISM: Saccharomyces cerevisiae

<400> SEQUENCE: 7
agctaagctt cgcggccgcc tttcgattag cacgcac                                      37

<210> SEQ ID NO 8
<211> LENGTH: 27
<212> TYPE: DNA
<213> ORGANISM: Saccharomyces cerevisiae

<400> SEQUENCE: 8
agataccttc atatgttatt attagtc                                                 27

<210> SEQ ID NO 9
<211> LENGTH: 35
<212> TYPE: DNA
<213> ORGANISM: Saccharomyces cerevisiae

<400> SEQUENCE: 9
agctaagctt cgcggccgcg cagaaatgat gaagg                                        35

<210> SEQ ID NO 10
<211> LENGTH: 29
<212> TYPE: DNA
<213> ORGANISM: Saccharomyces cerevisiae

<400> SEQUENCE: 10
atccatccca tatgtgatat ctcgattag                                               29

<210> SEQ ID NO 11
<211> LENGTH: 35
<212> TYPE: DNA
<213> ORGANISM: Saccharomyces cerevisiae

<400> SEQUENCE: 11
agctaagctt cgcggccgcg gaggtctgct tcacg                                        35

<210> SEQ ID NO 12
<211> LENGTH: 29
<212> TYPE: DNA
<213> ORGANISM: Saccharomyces cerevisiae

<400> SEQUENCE: 12
tacgatcgca tatgtaattg atataaacg                                               29

<210> SEQ ID NO 13
<211> LENGTH: 20
<212> TYPE: DNA
<213> ORGANISM: Saccharomyces cerevisiae

<400> SEQUENCE: 13

```
cctcaattgg attagtctca                                              20

<210> SEQ ID NO 14
<211> LENGTH: 20
<212> TYPE: DNA
<213> ORGANISM: Saccharomyces cerevisiae

<400> SEQUENCE: 14
cacctcgata tgtgcatctg                                              20

<210> SEQ ID NO 15
<211> LENGTH: 63
<212> TYPE: DNA
<213> ORGANISM: Saccharomyces cerevisiae

<400> SEQUENCE: 15
ggccagtgaa ttgtaatacg actcactata gggaggcggt tttttttttt tttttttttt  60
ttt                                                                63

<210> SEQ ID NO 16
<211> LENGTH: 20
<212> TYPE: DNA
<213> ORGANISM: Saccharomyces cerevisiae

<400> SEQUENCE: 16
gtcaagatgc taccgttcag                                              20

<210> SEQ ID NO 17
<211> LENGTH: 23
<212> TYPE: DNA
<213> ORGANISM: Saccharomyces cerevisiae
<220> FEATURE:
<221> NAME/KEY: unsure
<222> LOCATION: (17)..(23)
<223> OTHER INFORMATION: The symbol "n" at positions 17 to 23 represents
      any nucleotide.

<400> SEQUENCE: 17
aagcttcgcg gccgcgnnnn nnn                                          23

<210> SEQ ID NO 18
<211> LENGTH: 33
<212> TYPE: DNA
<213> ORGANISM: Saccharomyces cerevisiae
<220> FEATURE:
<221> NAME/KEY: unsure
<222> LOCATION: (27)..(33)
<223> OTHER INFORMATION: The symbol "n" at positions 27 to 33 represents
      any nucleotide.

<400> SEQUENCE: 18
aagcttagct aagcttcgcg gccgcgnnnn nnn                               33

<210> SEQ ID NO 19
<211> LENGTH: 12844
<212> TYPE: DNA
<213> ORGANISM: Saccharomyces cerevisiae

<400> SEQUENCE: 19
aagcttcgcg gccgcgtct gatttccgtt ttgggaatcc tttgccgcgc gcccctctca    60
aaactccgca caagtcccag aaagcgggaa agaaataaaa cgccaccaaa aaaaaaaaa   120 taaaagccaa tcctcgaagc gtgggtggta ggccctggat tatcccgtac aagtatttct   180
caggagtaaa aaaaccgttt gttttggaat tccccatttc gcggccacct acgccgctat   240
```

```
ctttgcaaca actatctgcg ataactcagc aaattttgca tattcgtgtt gcagtattgc      300
gataatggga gtcttacttc aacataacg gcagaaagaa atgtgagaaa attttgcatc       360
ctttgcctcc gttcaagtat ataaagtcgg catgcttgat aatctttctt tccatcctac     420
attgttctaa ttattcttat tctcctttat tctttcctaa cataccaaga aattaatctt     480
ctgtcattcg cttaaacact atatcacata tggaagacgc caaaaacata agaaaggcc      540 cggcgccatt ctatccgctg aagatggaa ccgctggaga gcaactgcat aaggctatga      600
agagatacgc cctggttcct ggaacaattg cttttacaga tgcacatatc gaggtggaca     660
tcacttacgc tgagtacttc gaaatgtccg ttcggttggc agaagctatg aaacgatatg     720
ggctgaatac aaatcacaga atcgtcgtat gcagtgaaaa ctctcttcaa ttctttatgc     780
cggtgttggg cgcgttattt atcggagttg cagttgcgcc cgcgaacgac atttataatg     840
aacgtgaatt gctcaacagt atgggcattt cgcagcctac cgtggtgttc gtttccaaaa    900
aggggttgca aaaattttg aacgtgcaaa aaaagctccc aatcatccaa aaaattatta     960
tcatggattc taaaacggat taccagggat ttcagtcgat gtacacgttc gtcacatctc    1020
atctacctcc cggtttttaat gaatacgatt ttgtgccaga gtccttcgat agggacaaga   1080
caattgcact gatcatgaac tcctctggat ctactggtct gcctaaaggt gtcgctctgc    1140
ctcatagaac tgcctgcgtg agattctcgc atgccagaga tcctattttt ggcaatcaaa    1200
tcattccgga tactgcgatt ttaagtgttg ttccattcca tcacggtttt ggaatgttta    1260
ctacactcgg atatttgata tgtggatttc gagtcgtctt aatgtataga tttgaagaag    1320
agctgtttct gaggagcctt caggattaca agattcaaag tgcgctgctg gtgccaaccc    1380
tattctcctt cttcgccaaa agcactctga ttgacaaata cgatttatct aatttacacg    1440
aaattgcttc tggtggcgct cccctctcta aggaagtcgg ggaagcggtt gccaagaggt    1500
tccatctgcc aggtatcagg caaggatatg gctcactga gactcatca gctattctga     1560 ttacacccga gggggatgat aaaccgggcg cggtcggtaa agttgttcca ttttttgaag    1620
cgaaggttgt ggatctggat accgggaaaa cgctgggcgt taatcaaaga ggcgaactgt    1680
gtgtgagagg tcctatgatt atgtccggtt atgtaaacaa tccggaagcg accaacgcct    1740
tgattgacaa ggatggatgg ctacattctg gagacatagc ttactgggac gaagacgaac    1800
acttcttcat cgttgaccgc ctgaagtctc tgattaagta caaaggctat caggtggctc    1860
ccgctgaatt ggaatccatc ttgctccaac accccaacat cttcgacgca ggtgtcgcag    1920
gtcttcccga cgatgacgcc ggtgaacttc ccgccgccgt tgttgttttg gagcacggaa    1980
agacgatgac ggaaaaagag atcgtggatt acgtcgccag tcaagtaaca accgcgaaaa    2040
agttgcgcgg aggagttgtg tttgtggacg aagtaccgaa aggtcttacc ggaaaactcg    2100
acgcaagaaa aatcagagag atcctcataa aggccaagaa gggcggaaag atcgccgtgt    2160
aattggatcc agtttaaaca gtagctttgg acttcttcgc cagagggtttg gtcaagtctc    2220 caatcaaggt tgtcggcttg tctaccttgc cagaaattta cgaaaagatg gaaaagggtc    2280
aaatcgttgg tagatacgtt gttgacactt ctaaataagc gaattcttta tgatttatga    2340
tttttattat taaataagtt ataaaaaaaa taagtgtata caaattttaa agtgactctt    2400
aggttttaaa acgaaaattc ttgttcttga gtaactcttt cctgtaggtc aggttgcttt    2460
ctcaggtata gcatgaggtc gctcttattg accacacctc taccggcatg ccgagcaaat    2520
gcctgcaaat cgctccccat ttcacccaat tgtagatatg ctaactccag caatgagttg    2580
```

-continued

```
atgaatctcg gtgtgtattt tatgtcctca gaagacaaca cctgttgtaa tcgttcttcc    2640
acacggatcg cggccgcttg atcctctacg ccggacgcat cgtggccggc atcaccggcg    2700
ccacaggtgc ggttgctggc gcctatatcg ccgacatcac cgatggggaa gatcgggctc    2760
gccacttcgg gctcatgagc gcttgtttcg gcgtgggtat ggtggcaggc cccgtggccg    2820
ggggactgtt gggcgccatc tccttgcatg caccattcct tgcggcggcg gtgctcaacg    2880
gcctcaacct actactgggc tgcttcctaa tgcaggagtc gcataaggga gagcgtcgac    2940
cgatgccctt gagagccttc aacccagtca gctccttccg gtgggcgcgg ggcatgacta    3000
tcgtcgccgc acttatgact gtcttcttta tcatgcaact cgtaggacag gtgccggcag    3060
cgctctgggt cattttcggc gaggaccgct ttcgctggag cgcgacgatg atcggcctgt    3120
cgcttgcggt attcggaatc ttgcacgccc tcgctcaagc cttcgtcact ggtcccgcca    3180
ccaaacgttt cggcgagaag caggccatta tcgccggcat ggcggccgac gcgctgggct    3240
acgtcttgct ggcgttcgcg acgcgaggct ggatggcctt ccccattatg attcttctcg    3300
cttccggcgg catcgggatg cccgcgttgc aggccatgct gtccaggcag gtagatgacg    3360
accatcaggg acagcttcaa ggatcgctcg cggctcttac cagcctaact tcgatcactg    3420
gaccgctgat cgtcacggcg atttatgccg cctcggcgag cacatggaac gggttggcat    3480
ggattgtagg cgccgcccta taccttgtct gcctccccgc gttgcgtcgc ggtgcatgga    3540
gccgggccac ctcgacctga atggaagccg gcggcacctc gctaacggat tcaccactcc    3600
aagaattgga gccaatcaat tcttgcggag aactgtgaat gcgcaaacca acccttggca    3660
gaacatatcc atcgcgtccg ccatctccag cagccgcacg cggcgcatct cgggcagcgt    3720
tgggtcctgg ccacgggtgc gcatgatcgt gctcctgtcg ttgaggaccc ggctaggctg    3780
gcggggttgc cttactggtt agcagaatga atcaccgata cgcgagcgaa cgtgaagcga    3840
ctgctgctgc aaaacgtctg cgacctgagc aacaacatga atggtcttcg gtttccgtgt    3900
ttcgtaaagt ctggaaacgc ggaagtcagc gccctgcacc attatgttcc ggatctgcat    3960
cgcaggatgc tgctggctac cctgtggaac acctacatct gtattaacga agcgctggca    4020
ttgaccctga gtgatttttc tctggtcccg ccgcatccat accgccagtt gtttaccctc    4080
acaacgttcc agtaaccggg catgttcatc atcagtaacc cgtatcgtga gcatcctctc    4140
tcgtttcatc ggtatcatta cccccatgaa cagaaattcc cccttacacg gaggcatcaa    4200
gtgaccaaac aggaaaaaac cgcccttaac atggcccgct ttatcagaag ccagacatta    4260
acgcttctgg agaaactcaa cgagctggac gcggatgaac aggcagacat ctgtgaatcg    4320
cttcacgacc acgctgatga gctttaccgc agctgcctcg cgcgtttcgg tgatgacggt    4380
gaaaacctct gacacatgca gctcccggag acggtcacag cttgtctgta agcggatgcc    4440
gggagcagac aagcccgtca gggcgcgtca gcgggtgttg gcgggtgtcg ggcgcagcc    4500 atgacccagt cacgtagcga tagcggagtg tatactggct taactatgcg gcatcagagc    4560
agattgtact gagagtgcac gatatccggt gtgaaatacc gcacagatgc gtaaggagaa    4620
aataccgcat caggcgctct tccgcttcct cgctcactga ctcgctgcgc tcggtcgttc    4680
ggctgcggcg agcggtatca gctcactcaa aggcggtaat acggttatcc acagaatcag    4740
gggataacgc aggaaagaac atgtgagcaa aaggccagca aaaggccagg aaccgtaaaa    4800
aggccgcgtt gctggcgttt ttccataggc tccgcccccc tgacgagcat cacaaaaatc    4860
gacgctcaag tcagaggtgg cgaaacccga caggactata aagataccag gcgtttcccc    4920
ctggaagctc cctcgtgcgc tctcctgttc cgaccctgcc gcttaccgga tacctgtccg    4980
```

```
cctttctccc ttcgggaagc gtggcgcttt ctcaatgctc acgctgtagg tatctcagtt    5040
cggtgtaggt cgttcgctcc aagctgggct gtgtgcacga accccccgtt cagcccgacc    5100
gctgcgcctt atccggtaac tatcgtcttg agtccaaccc ggtaagacac gacttatcgc    5160
cactggcagc agccactggt aacaggatta gcagagcgag gtatgtaggc ggtgctacag    5220
agttcttgaa gtggtggcct aactacggct acactagaag gacagtattt ggtatctgcg    5280
ctctgctgaa gccagttacc ttcggaaaaa gagttggtag ctcttgatcc ggcaaacaaa    5340
ccaccgctgg tagcggtggt ttttttgttt gcaagcagca gattacgcgc agaaaaaaag    5400
gatctcaaga agatcctttg atcttttcta cggggtctga cgctcagtgg aacgaaaact    5460
cacgttaagg gattttggtc atgagattat caaaaaggat cttcacctag atccttttaa    5520
attaaaaatg aagttttaaa tcaatctaaa gtatatatga gtaaacttgg tctgacagtt    5580
accaatgctt aatcagtgag gcacctatct cagcgatctg tctatttcgt tcatccatag    5640
ttgcctgact ccccgtcgtg tagataacta cgatacggga gggcttacca tctggcccca    5700
gtgctgcaat gataccgcga gacccacgct caccggctcc agatttatca gcaataaacc    5760
agccagccgg aagggccgag cgcagaagtg gtcctgcaac tttatccgcc tccatccagt    5820
ctattaattg ttgccgggaa gctagagtaa gtagttcgcc agttaatagt ttgcgcaacg    5880
ttgttgccat tgctgcaggc atcgtggtgt cacgctcgtc gtttggtatg gcttcattca    5940
gctccggttc ccaacgatca aggcgagtta catgatcccc catgttgtgc aaaaaagcgg    6000
ttagctcctt cggtcctccg atcgttgtca gaagtaagtt ggccgcagtg ttatcactca    6060
tggttatggc agcactgcat aattctctta ctgtcatgcc atccgtaaga tgcttttctg    6120
tgactggtga gtactcaacc aagtcattct gagaatagtg tatgcggcga ccgagttgct    6180
cttgcccggc gtcaacacgg gataataccg cgccacatag cagaacttta aaagtgctca    6240
tcattggaaa acgttcttcg gggcgaaaac tctcaaggat cttaccgctg ttgagatcca    6300
gttcgatgta acccactcgt gcacccaact gatcttcagc atcttttact ttcaccagcg    6360
tttctgggtg agcaaaaaca ggaaggcaaa atgccgcaaa aaagggaata agggcgacac    6420
ggaaatgttg aatactcata ctcttccttt ttcaatatta ttgaagcatt tatcagggtt    6480
attgtctcat gagcggatac atatttgaat gtatttagaa aaataaacaa ataggggttc    6540
cgcgcacatt tccccgaaaa gtgccacctg acgtctaaga aaccattatt atcatgacat    6600
taacctataa aaataggcgt atcacgaggc cctttcgtct tcaagaattc cacggactat    6660
agactatact agtatactcc gtctactgta cgatacactt ccgctcaggt ccttgtcctt    6720
taacgaggcc ttaccactct tttgttactc tattgatcca gctcagcaaa ggcagtgtga    6780
tctaagattc tatcttcgcg atgtagtaaa actagctaga ccgagaaaga gactagaaat    6840
gcaaaaggca cttctacaat ggctgccatc attattatcc gatgtgacgc tgcagaagca    6900
gaaatacacg cggtcagtga agctattccg ctattgaata acctcagtca ccttgtgcaa    6960
gaacttaaca agaaaccaat tattaaaggc ttacttactg atagtagatc aacgatcagt    7020
ataattaagt ctacaaatga agagaaattt agaaacagat ttttttggcac aaaggcaatg    7080
agacttagag atgaagtatc aggtaataat ttatacgtat actacatcga gaccaagaag    7140
aacattgctg atgtgatgac aaaacctctt ccgataaaaa catttaaact attaactaac    7200
aaatggattc attagatcta ttacattatg ggtggtatgt tggaataaaa atcaactatc    7260
atctactaac tagtatttac gttactagta tattatcata tacggtgtta agagatgacg    7320
```

-continued

```
caaatgatga gaaatagtca tctaaattag tggaagctga aacgcaagga ttgataatgt      7380
aataggatca atgaatatta acatataaaa tgatgataat aatatttata gaattgtgta      7440
gaattgcaga ttcccttta tggattccta atcctcgag gagaacttct agtatatcta       7500 cataccaat attattgcct tattaaaaat ggaatcccaa caattacatc aaaatccaca      7560
ttctcttcaa aatcaattgt cctgtacttc cttgttcatg tgtgttcaaa acgttatat      7620 ttataggata attatactct atttctcaac aagtaattgg ttgtttggcc gagcggtcta     7680
aggcgcctga ttcaagaaat atcttgaccg cagttaactg tgggaatact caggtatcgt    7740
aagatgcaag agttcgaatc tcttagcaac cattattttt ttcctcaaca taacgagaac    7800 acacagggc gctatcgcac agaatcaat tcgatgactg gaatttttt gttaatttca       7860 gaggtcgcct gacgcatata cctttttcaa ctgaaaaatt gggagaaaaa ggaaaggtga    7920
gagccgcgga accggctttt catatagaat agagaagcgt tcatgactaa atgcttgcat    7980
cacaatactt gaagttgaca atattattta aggacctatt gtttttttcca ataggtggtt   8040 agcaatcgtc ttactttcta actttttctta ccttttacat ttcagcaata tatatatata   8100
tatttcaagg atataccatt ctaatgtctg ccctaagaa gatcgtcgtt ttgccaggtg     8160
accacgttgg tcaagaaatc acagccgaag ccattaaggt tcttaaagct atttctgatg   8220
ttcgttccaa tgtcaagttc gatttcgaaa atcatttaat tggtggtgct gctatcgatg   8280
ctacaggtgt cccacttcca gatgaggcgc tggaagcctc caagaaggtt gatgccgttt   8340
tgttaggtgc tgtgggtggt cctaaatggg gtaccggtag tgttagacct gaacaaggtt   8400 tactaaaat ccgtaaagaa cttcaattgt acgccaactt aagaccatgt aactttgcat    8460
ccgactctct tttagactta tctccaatca agccacaatt tgctaaaggt actgacttcg   8520
ttgttgtcag agaattagtg ggaggtattt actttggtaa gagaaaggaa gacgatggtg   8580
atggtgtcgc ttgggatagt gaacaataca ccgttccaga agtgcaaaga atcacaagaa  8640
tggccgcttt catggcccta caacatgagc caccattgcc tatttggtcc ttggataaag   8700
ctaatgtttt ggcctcttca agattatgga gaaaaactgt ggaggaaacc atcaagaacg   8760
aattccctac attgaaggtt caacatcaat tgattgattc tgccgccatg atcctagtta    8820
agaacccaac ccacctaaat ggtattataa tcaccagcaa catgtttggt gatatcatct   8880
ccgatgaagc ctccgttatc ccaggttcct tgggtttgtt gccatctgcg tccttggcct   8940
ctttgccaga caagaacacc gcatttggtt tgtacgaacc atgccacggt tctgctccag   9000
atttgccaaa gaataaggtc aaccctatcg ccactatctt gtctgctgca atgatgttga   9060
aattgtcatt gaacttgcct gaagaaggta aggccattga agatgcagtt aaaaaggttt   9120
tggatgcagg tatcagaact ggtgatttag gtggttccaa cagtaccacg gaagtcggtg   9180
atgctgtcgc cgaagaagtt aagaaaatcc ttgcttaaaa agattctctt tttttatgat   9240
atttgtacat aaactttata aatgaaattc ataatagaaa cgacacgaaa ttacaaaatg   9300
gaatatgttc atagggtaga cgaaactata tacgcaatct acatacattt atcaagaagg   9360
agaaaaagga ggatgtaaag gaatacaggt aagcaaattg atactaatgg ctcaacgtga   9420
taaggaaaaa gaattgcact ttaacattaa tattgacaag gaggagggca ccacacaaaa   9480
agttaggtgt aacagaaaat catgaaacta tgattcctaa tttatatatt ggaggatttt    9540
ctctaaaaaa aaaaaaatac aacaaataaa aaacactcaa tgacctgacc atttgatgga   9600
gtttaagtca ataccttctt gaaccatttc ccataatggt gaaagttccc tcaagaattt   9660
tactctgtca gaaacggcct taacgacgta gtcgacctcc tcttcagtac taaatctacc   9720
```

-continued

```
aataccaaat ctgatggaag aatgggctaa tgcatcatcc ttacccagcg catgtaaaac    9780
ataagaaggt tctagggaag cagatgtaca ggctgaaccc gaggataatg cgatatccct    9840
tagtgccatc aataaagatt ctccttccac gtaggcgaaa gaaacgttaa cacaccctgg    9900
ataacgatga tctggagatc cgttcaacgt ggtatgttca gcggataata gacctttgac    9960
taatttatcg gatagtcttt tgatgtgagc ttggtcgttg tcaaattctt tcttcatcaa   10020
tctcgcagct tcaccaaatc ccgctaccaa tgggggggcc aaagtaccag atctcaatcc   10080
tctctcttgg ccaccaccgg atagtaaagg ttctaatcta actcttggtc tccttcttac   10140
atagatggca cctattccct ttggaccgta aatcttgtga aagaaattg atagtaaatc    10200 aatgttcatt tcattgacat caatgtgaat cttaccatag gcttgtgcgg cgtcagtatg   10260
aaagtagatc ttattctttc tacaaattgc accaatttct ttaataggtt gaatgacacc   10320
gatttcatta ttgacagcca tcacagagac gagacaggta tctggtctaa tggcatcttc   10380
caattccttc aaatcgataa gaccttgatc gtccacattt aggaaagtga cttcaaatcc   10440
ctccttcatc atggcccgtg cggcttccaa gacacacttg tgttccgttc tagtggtgat   10500
gatgtgtttc ttagtcttct tataaaatct tgggacaccc ttaagaacca tattattaga   10560
ttcggtcgct cccgaagtga atattatttc cttggggtcg gcattgatca tctttgctac   10620
gtaagctcta gcattttcca cagcagtatt tgtttcccaa ccgtaagagt gagtgttgga   10680
atgaggatta cctaaaagtc ccgtataaaa cttcaacatc gtatccaaaa ccctagggtc   10740
tgttggtgta gtggcttgca tgtcaagata tatgggacga gtaccaaaac ctgtgttttc   10800
ttgataagca tggctcattg cagtgctacc agaagctact acagcatctg gggtggtacc   10860
ggatgcactc gcacgggcac tagcctgtgc ctttgcagca gcctgaatat cggtatgcgt   10920
ttccagagag aagttgtcgt ctaacttcac gcctgctgca gtctcaatga tattcgaata   10980
cgctttgagg agatacagcc taatatccga caaactgttt tacagattta cgatcgtact   11040
tgttacccat cattgaattt tgaacatccg aacctgggag ttttccctga aacagatagt   11100
atatttgaac ctgtataata atatatagtc tagcgcttta cggaagacaa tgtatgtatt   11160
tcggttcctg gagaaactat tgcatctatt gcataggtaa tcttgcacgt cgcatccccg   11220 gttcatttc tgcgtttcca tcttgcactt caatagcata tctttgttaa cgaagcatct    11280
gtgcttcatt ttgtagaaca aaaatgcaac gcgagagcgc taattttttca aacaaagaat   11340 ctgagctgca ttttttacaga acagaaatgc aacgcgaaag cgctatttta ccaacgaaga   11400
atctgtgctt cattttttgta aaacaaaaat gcaacgcgag agcgctaatt tttcaaacaa   11460
agaatctgag ctgcattttt acagaacaga atgcaacgc gagagcgcta ttttaccaac    11520
aaagaatcta tacttctttt ttgttctaca aaaatgcatc ccgagagcgc tattttttcta   11580 acaaagcatc ttagattact ttttttctcc tttgtgcgct ctataatgca gtctcttgat   11640 aacttttttgc actgtaggtc cgttaaggtt agaagaaggc tactttggtg tctatttttct  11700 cttccataaa aaaagcctga ctccacttcc cgcgtttact gattactagc gaagctgcgg   11760
gtgcattttt tcaagataaa ggcatccccg attatattct ataccgatgt ggattgcgca   11820
tactttgtga acagaaagtg atagcgttga tgattcttca ttggtcagaa aattatgaac   11880
ggtttcttct attttgtctc tatatactac gtataggaaa tgtttacatt ttcgtattgt   11940
tttcgattca ctctatgaat agttcttact acaattttt tgtctaaaga gtaatactag    12000
agataaacat aaaaaatgta gaggtcgagt ttagatgcaa gttcaaggag cgaaaggtgg   12060
```

-continued

| | | | | |
|---|---|---|---|---|
| atgggtaggt | tatataggga | tatagcacag | agatatatag | caaagagata cttttgagca | 12120 |
| atgtttgtgg | aagcggtatt | cgcaatattt | tagtagctcg | ttacagtccg gtgcgttttt | 12180 |
| ggttttttga | aagtgcgtct | tcagagcgct | tttggttttc | aaaagcgctc tgaagttcct | 12240 |
| atactttcta | gagaatagga | acttcggaat | aggaacttca | aagcgtttcc gaaaacgagc | 12300 |
| gcttccgaaa | atgcaacgcg | agctgcgcac | atacagctca | ctgttcacgt cgcacctata | 12360 |
| tctgcgtgtt | gcctgtatat | atatatacat | gagaagaacg | gcatagtgcg tgtttatgct | 12420 |
| taaatgcgta | cttatatgcg | tctatttatg | taggatgaaa | ggtagtctag tacctcctgt | 12480 |
| gatattatcc | cattccatgc | ggggtatcgt | atgcttcctt | cagcactacc ctttagctgt | 12540 |
| tctatatgct | gccactcctc | aattggatta | gtctcatcct | tcaatgctat catttccttt | 12600 |
| gatattcgat | cctaggcata | gtaccgagaa | actagtgcga | agtagtgatc aggtattgct | 12660 |
| gttatctgat | gagtatacgt | tgtcctggcc | acggcagaag | cacgcttatc gctccaattt | 12720 |
| cccacaacat | tagtcaactc | cgttaggccc | ttcattgaaa | gaaatgaggt catcaaatgt | 12780 |
| cttccaatgt | gagattttgg | gccattttt | atagcaaaga | ttgaataagg cgcatttttc | 12840 |
| ttca | | | | | 12844 |

<210> SEQ ID NO 20
<211> LENGTH: 13073
<212> TYPE: DNA
<213> ORGANISM: Saccharomyces cerevisiae

<400> SEQUENCE: 20

| | | | | |
|---|---|---|---|---|
| aagcttcgcg | gccgcctttc | gattagcacg | cacacacatc | acatagactg cgtcataaaa | 60 |
| atacactacg | gaaaaaccat | aaagagcaaa | gcgatacccta | cttggaagga aaaggagcac | 120 |
| gcttgtaagg | gggatggggg | ctaagaagtc | attcactttc | ttttcccttc gcggtccgga | 180 |
| cccgggaccc | ctcctctccc | cgcacgattt | cttcctttca | tatcttcctt ttattcctat | 240 |
| cccgttgaag | caaccgcact | atgactaaat | ggtgctggac | atctccatgg ctgtgacttg | 300 |
| tgtgtatctc | acagtggtaa | cggcaccgtg | gctcggaaac | ggttccttcg tgacaattct | 360 |
| agaacagggg | ctacagtctc | gataatagaa | taataagcgc | attttttgcta gcgccgccgc | 420 |
| ggcgcccgtt | tcccaatagg | gaggcgcagt | ttatcggcgg | agctctactt cttcctattt | 480 |
| gggtaagccc | ctttctgttt | tcggccagtg | gttgctgcag | gctgcgccgg agaacatagt | 540 |
| gataagggat | gtaactttcg | atgagagaat | tagcaagcgg | aaaaaaacta tggctagctg | 600 |
| ggagttgttt | ttcaatcata | taaaagggag | aaattgttgc | tcactatgtg acagtttctg | 660 |
| ggacgtctta | acttttattg | cagaggacta | tcaaatcata | cagatattgt caaaaaaaaa | 720 |
| aaagactaat | aataacatat | ggaagacgcc | aaaaacataa | agaaaggccc ggcgccattc | 780 |
| tatccgctgg | aagatggaac | cgctggagag | caactgcata | aggctatgaa gagatacgcc | 840 |
| ctggttcctg | gaacaattgc | ttttacagat | gcacatatcg | aggtggacat cacttacgct | 900 |
| gagtacttcg | aaatgtccgt | tcggttggca | gaagctatga | acgatatggc tgaataca | 960 |
| aatcacagaa | tcgtcgtatg | cagtgaaaac | tctcttcaat | tctttatgcc ggtgttgggc | 1020 |
| gcgttattta | tcggagttgc | agttgcgccc | gcgaacgaca | tttataatga acgtgaattg | 1080 |
| ctcaacagta | tgggcatttc | gcagcctacc | gtggtgttca | tttccaaaaa ggggttgcaa | 1140 |
| aaaattttga | acgtgcaaaa | aaagctccca | atcatccaaa | aaattattat catggattct | 1200 |
| aaaacggatt | accagggatt | tcagtcgatg | tacacgttcg | tcacatctca tctacctccc | 1260 |
| ggttttaatg | aatacgattt | tgtgccagag | tccttcgata | gggacaagac aattgcactg | 1320 |

-continued

```
atcatgaact cctctggatc tactggtctg cctaaaggtg tcgctctgcc tcatagaact      1380
gcctgcgtga gattctcgca tgccagagat cctattttg gcaatcaaat cattccggat       1440
actgcgattt taagtgttgt tccattccat cacggttttg gaatgtttac tacactcgga      1500
tatttgatat gtggatttcg agtcgtctta atgtatagat ttgaagaaga gctgtttctg      1560
aggagccttc aggattacaa gattcaaagt gcgctgctgg tgccaaccct attctccttc      1620
ttcgccaaaa gcactctgat tgacaaatac gatttatcta atttacacga aattgcttct      1680
ggtgcgctc ccctctctaa ggaagtcggg aagcggttg ccaagaggtt ccatctgcca        1740
ggtatcaggc aaggatatgg gctcactgag actacatcag ctattctgat tacacccgag      1800
ggggatgata aaccgggcgc ggtcggtaaa gttgttccat tttttgaagc gaaggttgtg      1860
gatctggata ccgggaaaac gctgggcgtt aatcaaagag gcgaactgtg tgtgagaggt      1920
cctatgatta tgtccggtta tgtaaacaat ccggaagcga ccaacgcctt gattgacaag      1980
gatggatggc tacattctgg agacatagct tactgggacg aagacgaaca cttcttcatc      2040
gttgaccgcc tgaagtctct gattaagtac aaaggctatc aggtggctcc cgctgaattg      2100
gaatccatct tgctccaaca ccccaacatc ttcgacgcag gtgtcgcagg tcttcccgac      2160
gatgacgccg gtgaacttcc cgccgccgtt gttgttttgg agcacggaaa gacgatgacg      2220
gaaaaagaga tcgtggatta cgtcgccagt caagtaacaa ccgcgaaaaa gttgcgcgga      2280
ggagttgtgt ttgtggacga agtaccgaaa ggtcttaccg gaaaactcga cgcaagaaaa      2340
atcagagaga tcctcataaa ggccaagaag ggcggaaaga tcgccgtgta attggatcca      2400
gtttaaacag tagctttgga cttcttcgcc agaggtttgg tcaagtctcc aatcaaggtt      2460
gtcggcttgt ctaccttgcc agaaatttac gaaaagatgg aaaagggtca aatcgttggt      2520
agatacgttg ttgacacttc taaataagcg aatttcttat gatttatgat ttttattatt      2580
aaataagtta taaaaaaaat aagtgtatac aaattttaaa gtgactctta ggttttaaaa      2640
cgaaaattct tgttcttgag taactctttc ctgtaggtca ggttgctttc tcaggtatag      2700
catgaggtcg ctcttattga ccacacctct accggcatgc cgagcaaatg cctgcaaatc      2760
gctcccatt tcacccaatt gtagatatgc taactccagc aatgagttga tgaatctcgg      2820
tgtgtatttt atgtcctcag aagacaacac ctgttgtaat cgttcttcca cacgatcgc      2880
ggccgcttga tcctctacgc cggacgcatc gtggccggca tcaccggcgc cacaggtgcg      2940
gttgctggcg cctatatcgc cgacatcacc gatggggaag atcgggctcg ccacttcggg      3000
ctcatgagcg cttgtttcgg cgtgggtatg gtggcaggcc ccgtggccgg gggactgttg      3060
ggcgccatct ccttgcatgc accattcctt gcggcggcgg tgctcaacgg cctcaaccta      3120
ctactgggct gcttcctaat gcaggagtcg cataagggag agcgtcgacc gatgcccttg      3180
agagccttca acccagtcag ctccttccgg tgggcgcggg gcatgactat cgtcgccgca      3240
cttatgactg tcttctttat catgcaactc gtaggacagg tgccggcagc gctctgggtc      3300
attttcggcg aggaccgctt tcgctggagc gcgacgatga tcggcctgtc gcttgcggta      3360
ttcggaatct tgcacgccct cgctcaagcc ttcgtcactg gtcccgccac caaacgtttc      3420
ggcgagaagc aggccattat cgccggcatg gcggccgacg cgctgggcta cgtcttgctg      3480
gcgttcgcga cgcgaggctg gatggccttc cccattatga ttcttctcgc ttccggcggc      3540
atcgggatgc ccgcgttgca ggccatgctg tccaggcagg tagatgacga ccatcaggga      3600
cagcttcaag gatcgctcgc ggctcttacc agcctaactt cgatcactgg accgctgatc      3660
```

-continued

```
gtcacggcga tttatgccgc ctcggcgagc acatggaacg ggttggcatg gattgtaggc    3720
gccgccctat accttgtctg cctccccgcg ttgcgtcgcg gtgcatggag ccggccacc     3780
tcgacctgaa tggaagccgg cggcacctcg ctaacggatt caccactcca agaattggag    3840
ccaatcaatt cttgcggaga actgtgaatg cgcaaaccaa cccttggcag aacatatcca    3900
tcgcgtccgc catctccagc agccgcacgg ggcgcatctc gggcagcgtt gggtcctggc    3960
cacgggtgcg catgatcgtg ctcctgtcgt tgaggacccg gctaggctgg cggggttgcc    4020
ttactggtta gcagaatgaa tcaccgatac gcgagcgaac gtgaagcgac tgctgctgca    4080
aaacgtctgc gacctgagca acaacatgaa tggtcttcgg tttccgtgtt tcgtaaagtc    4140
tggaaacgcg gaagtcagcg ccctgcacca ttatgttccg gatctgcatc gcaggatgct    4200
gctggctacc ctgtggaaca cctacatctg tattaacgaa gcgctggcat tgaccctgag    4260
tgattttct ctggtcccgc cgcatccata ccgccagttg tttaccctca caacgttcca     4320
gtaaccgggc atgttcatca tcagtaaccc gtatcgtgag catcctctct cgtttcatcg    4380
gtatcattac ccccatgaac agaaattccc ccttacacgg aggcatcaag tgaccaaaca    4440
ggaaaaaacc gcccttaaca tggcccgctt tatcagaagc cagacattaa cgcttctgga    4500
gaaactcaac gagctggacg cggatgaaca ggcagacatc tgtgaatcgc ttcacgacca    4560
cgctgatgag ctttaccgca gctgcctcgc gcgtttcggt gatgacgtg aaaacctctg     4620
acacatgcag ctcccggaga cggtcacagc ttgtctgtaa gcggatgccg ggagcagaca    4680
agcccgtcag ggcgcgtcag cgggtgttgg cgggtgtcgg ggcgcagcca tgacccagtc    4740
acgtagcgat agcggagtgt atactggctt aactatgcgg catcagagca gattgtactg    4800
agagtgcacg atatccggtg tgaaataccg cacagatgcg taaggagaaa ataccgcatc    4860
aggcgctctt ccgcttcctc gctcactgac tcgctgcgct cggtcgttcg gctgcggcga    4920
gcggtatcag ctcactcaaa ggcggtaata cggttatcca cagaatcagg gataacgca     4980
ggaaagaaca tgtgagcaaa aggccagcaa aaggccagga accgtaaaaa ggccgcgttg    5040
ctggcgtttt tccataggct ccgcccccct gacgagcatc acaaaaatcg acgctcaagt    5100
cagaggtggc gaaacccgac aggactataa agataccagg cgtttccccc tggaagctcc    5160
ctcgtgcgct ctcctgttcc gaccctgccg cttaccggat acctgtccgc ctttctccct    5220
tcgggaagcg tggcgctttc tcaatgctca cgctgtaggt atctcagttc ggtgtaggtc    5280
gttcgctcca agctgggctg tgtgcacgaa ccccccgttc agcccgaccg ctgcgcctta    5340
tccggtaact atcgtcttga gtccaacccg gtaagacacg acttatcgcc actggcagca    5400
gccactggta acaggattag cagagcgagg tatgtaggcg gtgctacaga gttcttgaag    5460
tggtggccta actacggcta cactagaagg acagtatttg gtatctgcgc tctgctgaag    5520
ccagttacct tcggaaaaag agttggtagc tcttgatccg gcaaacaaac caccgctggt    5580
agcggtggtt tttttgtttg caagcagcag attacgcgca gaaaaaaagg atctcaagaa    5640
gatcctttga tcttttctac ggggtctgac gctcagtgga acgaaaactc acgttaaggg    5700
attttggtca tgagattatc aaaaaggatc ttcacctaga tccttttaaa ttaaaaatga    5760
agttttaaat caatctaaag tatatatgag taaacttggt ctgacagtta ccaatgctta    5820
atcagtgagg cacctatctc agcgatctgt ctatttcgtt catccatagt tgcctgactc    5880
cccgtcgtgt agataactac gatacgggag ggcttaccat ctggccccag tgctgcaatg    5940
ataccgcgag acccacgctc accggctcca gatttatcag caataaacca gccagccgga    6000
agggccgagc gcagaagtgg tcctgcaact ttatccgcct ccatccagtc tattaattgt    6060
```

-continued

```
tgccgggaag ctagagtaag tagttcgcca gttaatagtt tgcgcaacgt tgttgccatt      6120
gctgcaggca tcgtggtgtc acgctcgtcg tttggtatgg cttcattcag ctccggttcc      6180
caacgatcaa ggcgagttac atgatccccc atgttgtgca aaaagcggt tagctccttc       6240 ggtcctccga tcgttgtcag aagtaagttg gccgcagtgt tatcactcat ggttatggca      6300
gcactgcata attctcttac tgtcatgcca tccgtaagat gcttttctgt gactggtgag      6360
tactcaacca agtcattctg agaatagtgt atgcggcgac cgagttgctc ttgcccggcg      6420
tcaacacggg ataataccgc gccacatagc agaactttaa agtgctcat cattggaaaa       6480 cgttcttcgg ggcgaaaact ctcaaggatc ttaccgctgt tgagatccag ttcgatgtaa      6540
cccactcgtg cacccaactg atcttcagca tctttactt tcaccagcgt ttctgggtga       6600
gcaaaaacag gaaggcaaaa tgccgcaaaa aagggaataa gggcgacacg gaaatgttga     6660
atactcatac tcttccttt tcaatattat tgaagcattt atcagggtta ttgtctcatg       6720
agcggataca tatttgaatg tatttagaaa aataaacaaa taggggttcc gcgcacattt      6780
ccccgaaaag tgccacctga cgtctaagaa accattatta tcatgacatt aacctataaa      6840
aataggcgta tcacgaggcc ctttcgtctt caagaattcc acggactata gactatacta     6900
gtatactccg tctactgtac gatacacttc cgctcaggtc cttgtccttt aacgaggcct     6960
taccactctt ttgttactct attgatccag ctcagcaaag gcagtgtgat ctaagattct     7020
atcttcgcga tgtagtaaaa ctagctagac cgagaaagag actagaaatg caaaaggcac   7080
ttctacaatg gctgccatca ttattatccg atgtgacgct gcagaagcag aaatacacgc    7140
ggtcagtgaa gctattccgc tattgaataa cctcagtcac cttgtgcaag aacttaacaa    7200
gaaaccaatt attaaaggct tacttactga tagtagatca acgatcagta taattaagtc    7260
tacaaatgaa gagaaattta gaaacagatt ttttggcaca aaggcaatga gacttagaga   7320
tgaagtatca ggtaataatt tatacgtata ctacatcgag accaagaaga acattgctga   7380
tgtgatgaca aaacctcttc cgataaaaac atttaaacta ttaactaaca aatggattca   7440
ttagatctat tacattatgg gtggtatgtt ggaataaaaa tcaactatca tctactaact    7500
agtatttacg ttactagtat attatcatat acggtgttag aagatgacgc aaatgatgag   7560
aaatagtcat ctaaattagt ggaagctgaa acgcaaggat tgataatgta ataggatcaa    7620
tgaatattaa catataaaat gatgataata atatttatag aattgtgtag aattgcagat   7680 tccctttat ggattcctaa atcctcgagg agaacttcta gtatatctac atacctaata    7740
ttattgcctt attaaaaatg gaatcccaac aattacatca aaatccacat tctcttcaaa   7800
atcaattgtc ctgtacttcc ttgttcatgt gtgttcaaaa acgttatatt tataggataa   7860
ttatactcta tttctcaaca agtaattggt tgtttggccg agcggtctaa ggcgcctgat   7920
tcaagaaata tcttgaccgc agttaactgt gggaatactc aggtatcgta agatgcaaga   7980
gttcgaatct cttagcaacc attattttt tcctcaacat aacgagaaca cacagggggcg   8040 ctatcgcaca gaatcaaatt cgatgactgg aaatttttg ttaatttcag aggtcgcctg    8100
acgcatatac cttttcaac tgaaaaattg ggagaaaaag gaaaggtgag agccgcggaa    8160
ccggcttttc atatagaata gagaagcgtt catgactaaa tgcttgcatc acaatacttg   8220
aagttgacaa tattatttaa ggacctattg tttttccaa taggtggtta gcaatcgtct    8280
tactttctaa cttttcttac cttttacatt tcagcaatat atatatat atttcaagga     8340 tataccattc taatgtctgc ccctaagaag atcgtcgttt tgccaggtga ccacgttggt   8400
```

```
caagaaatca cagccgaagc cattaaggtt cttaaagcta tttctgatgt tcgttccaat    8460
gtcaagttcg atttcgaaaa tcatttaatt ggtggtgctg ctatcgatgc tacaggtgtc    8520
ccacttccag atgaggcgct ggaagcctcc aagaaggttg atgccgtttt gttaggtgct    8580
gtgggtggtc ctaaatgggg taccggtagt gttagacctg aacaaggttt actaaaaatc    8640
cgtaaagaac ttcaattgta cgccaactta agaccatgta actttgcatc cgactctctt    8700
ttagacttat ctccaatcaa gccacaattt gctaaaggta ctgacttcgt tgttgtcaga    8760
gaattagtgg gaggtatttta ctttggtaag agaaaggaag acgatggtga tggtgtcgct    8820
tgggatagtg aacaatacac cgttccagaa gtgcaaagaa tcacaagaat ggccgctttc    8880
atggccctac aacatgagcc accattgcct atttggtcct tggataaagc taatgttttg    8940
gcctcttcaa gattatggag aaaaactgtg gaggaaacca tcaagaacga attccctaca    9000
ttgaaggttc aacatcaatt gattgattct gccgccatga tcctagttaa gaacccaacc    9060
cacctaaatg gtattataat caccagcaac atgtttggtg atatcatctc cgatgaagcc    9120
tccgttatcc caggttcctt gggtttgttg ccatctgcgt ccttggcctc tttgccagac    9180
aagaacaccg catttggttt gtacgaacca tgccacggtt ctgctccaga tttgccaaag    9240
aataaggtca accctatcgc cactatcttg tctgctgcaa tgatgttgaa attgtcattg    9300
aacttgcctg aagaaggtaa ggccattgaa gatgcagtta aaaaggtttt ggatgcaggt    9360
atcagaactg gtgatttagg tggttccaac agtaccacgg aagtcggtga tgctgtcgcc    9420
gaagaagtta agaaaatcct tgcttaaaaa gattctcttt ttttatgata tttgtacata    9480
aactttataa atgaaattca taatagaaac gacacgaaat tacaaaatgg aatatgttca    9540
tagggtagac gaaactatat acgcaatcta catacattta tcaagaagga gaaaaggag    9600
gatgtaaagg aatacaggta agcaaattga tactaatggc tcaacgtgat aaggaaaaag    9660
aattgcactt taacattaat attgacaagg aggagggcac cacacaaaaa gttaggtgta    9720
acagaaaatc atgaaactat gattcctaat ttatatattg gaggattttc tctaaaaaaa    9780
aaaaaataca acaaataaaa aacactcaat gacctgacca tttgatggag tttaagtcaa    9840
taccttcttg aaccatttcc cataatggtg aaagttccct caagaatttt actctgtcag    9900
aaacggcctt aacgacgtag tcgacctcct cttcagtact aaatctacca ataccaaatc    9960
tgatggaaga atgggctaat gcatcatcct tacccagcgc atgtaaaaca taagaaggtt   10020
ctagggaagc agatgtacag gctgaacccg aggataatgc gatatccctt agtgccatca   10080
ataaagattc tccttccacg taggcgaaag aaacgttaac acaccctgga taacgatgat   10140
ctggagatcc gttcaacgtg gtatgttcag cggataatag acctttgact aatttatcgg   10200
atagtctttt gatgtgagct tggtcgttgt caaattcttt cttcatcaat ctcgcagctt   10260
caccaaatcc cgctaccaat gggggggcca agtaccaga tctcaatcct ctctcttggc   10320
caccaccgga tagtaaaggt tctaatctaa ctcttggtct ccttcttaca tagatggcac   10380
ctattccctt tggaccgtaa atcttgtgag aagaaattga tagtaaatca atgttcattt   10440
cattgacatc aatgtgaatc ttaccatagg cttgtgcggc gtcagtatga aagtagatct   10500
tattctttct acaaattgca ccaatttctt taataggttg aatgacaccg atttcattat   10560
tgacagccat cacagagacg agacaggtat ctggtctaat gcatcttcc aattccttca   10620
aatcgataag accttgatcg tccacattta ggaaagtgac ttcaaatccc tccttcatca   10680
tggcccgtgc ggcttccaag acacacttgt gttccgttct agtggtgatg atgtgttcct   10740
tagtcttctt ataaaatctt gggacaccct taagaaccat attattagat tcggtcgctc   10800
```

```
ccgaagtgaa tattatttcc ttggggtcgg cattgatcat ctttgctacg taagctctag    10860
cattttccac agcagtattt gtttcccaac cgtaagagtg agtgttggaa tgaggattac    10920
cataaagtcc cgtataaaac ttcaacatcg tatccaaaac cctagggtct gttggtgtag    10980
tggcttgcat gtcaagatat atgggacgag taccaaaacc tgtgttttct tgataagcat    11040
ggctcattgc agtgctacca gaagctacta cagcatctgg ggtggtaccg gatgcactcg    11100
cacgggcact agcctgtgcc tttgcagcag cctgaatatc ggtatgcgtt tccagagaga    11160
agttgtcgtc taacttcacg cctgctgcag tctcaatgat attcgaatac gctttgagga    11220
gatacagcct aatatccgac aaactgtttt acagatttac gatcgtactt gttacccatc    11280
attgaatttt gaacatccga acctgggagt tttccctgaa acagatagta tatttgaacc    11340
tgtataataa tatatagtct agcgctttac ggaagacaat gtatgtattt cggttcctgg    11400
agaaactatt gcatctattg cataggtaat cttgcacgtc gcatcccgg ttcattttct     11460 gcgtttccat cttgcacttc aatagcatat ctttgttaac gaagcatctg tgcttcattt    11520
tgtagaacaa aaatgcaacg cgagagcgct aattttcaa acaaagaatc tgagctgcat     11580
ttttacagaa cagaaatgca acgcgaaagc gctattttac caacgaagaa tctgtgcttc    11640 attttttgtaa aacaaaaatg caacgcgaga gcgctaattt ttcaaacaaa gaatctgagc    11700
tgcattttta cagaacagaa atgcaacgcg agagcgctat tttaccaaca agaatctat     11760 acttcttttt tgttctacaa aaatgcatcc cgagagcgct attttctaa caaagcatct     11820 tagattactt tttttctcct ttgtgcgctc tataatgcag tctcttgata acttttttgca   11880 ctgtaggtcc gttaaggtta gaagaaggct actttggtgt ctattttctc ttccataaaa    11940
aaagcctgac tccacttccc gcgtttactg attactagcg aagctgcggg tgcatttttt    12000
caagataaag gcatccccga ttatattcta taccgatgtg gattgcgcat actttgtgaa    12060
cagaaagtga tagcgttgat gattcttcat tggtcagaaa attatgaacg gtttcttcta    12120
ttttgtctct atatactacg tataggaaat gtttacattt tcgtattgtt ttcgattcac    12180
tctatgaata gttcttacta caattttttt gtctaaagag taatactaga gataaacata    12240
aaaaatgtag aggtcgagtt tagatgcaag ttcaaggagc gaaaggtgga tgggtaggtt    12300
atatagggat atagcacaga gatatatagc aaagagatac ttttgagcaa tgtttgtgga    12360
agcggtattc gcaatatttt agtagctcgt tacagtccgg tgcgtttttg gttttttgaa    12420
agtgcgtctt cagagcgctt ttggttttca aaagcgctct gaagttccta ctttctag     12480 agaataggaa cttcggaata ggaacttcaa agcgtttccg aaaacgagcg cttccgaaaa    12540
tgcaacgcga gctgcgcaca tacagctcac tgttcacgtc gcacctatat ctgcgtgttg    12600
cctgtatata tatatacatg agaagaacgg catagtgcgt gtttatgctt aaatgcgtac    12660
ttatatgcgt ctatttatgt aggatgaaag gtagtctagt acctcctgtg atattatccc    12720
attccatgcg gggtatcgta tgcttccttc agcactaccc tttagctgtt ctatatgctg    12780
ccactcctca attggattag tctcatcctt caatgctatc atttcctttg atattcgatc    12840
ctaggcatag taccgagaaa ctagtgcgaa gtagtgatca ggtattgctg ttatctgatg    12900
agtatacgtt gtcctggcca cggcagaagc acgcttatcg ctccaatttc ccacaacatt    12960
agtcaactcc gttaggccct tcattgaaag aaatgaggtc atcaaatgtc ttccaatgtg    13020
agatttgggg ccatttttta tagcaaagat tgaataaggc gcatttttct tca           13073
```

<210> SEQ ID NO 21

-continued

```
<211> LENGTH: 12851
<212> TYPE: DNA
<213> ORGANISM: Saccharomyces cerevisiae

<400> SEQUENCE: 21
aagcttagct aagcttcgcg gccgcgcaga aatgatgaag ggtgttagcg ccgtccactg      60
atgtgcctgg tagtcatgat ttacgtataa ctaacacatc atgaggacgg cggcgtcacc     120
ccaacgcaaa agagtgactt ccctgcgctt tgccaaaacc ccatacatcg ccatctggct     180
cctggcaggg cggttgatgg acatcagccg cctcccttaa ttgctaaagc ctccacaagg     240
cacaattaag caatatttcg ggaaagtaca ccagtcagtt tgcgctttta tgactgggtt     300
ctaaggtact agatgtgaag tagtggtgac agaatcaggg agataagagg gagcagggtg     360
gggtaatgat gtgcgataac aatcttgctt ggctaatcac ccccatatct tgtagtgagt     420
atataaatag gagcctccct tcctattgca actccataaa attttttttt gtagccactt     480
ctgtaacaag ataaataaaa ccaactaatc gagatatcac atatggaaga cgccaaaaac     540
ataaagaaag gcccggcgcc attctatccg ctggaagatg gaaccgctgg agagcaactg     600
cataaggcta tgaagagata cgccctggtt cctggaacaa ttgcttttac agatgcacat     660
atcgaggtgg acatcactta cgctgagtac ttcgaaatgt ccgttcggtt ggcagaagct     720
atgaaacgat atgggctgaa tacaaatcac agaatcgtcg tatgcagtga aaactctctt     780
caattcttta tgccggtgtt gggcgcgtta tttatcggag ttgcagttgc gcccgcgaac     840
gacatttata atgaacgtga attgctcaac agtatgggca tttcgcagcc taccgtggtg     900
ttcgtttcca aaaggggtt gcaaaaaatt ttgaacgtgc aaaaaaagct cccaatcatc     960
caaaaaatta ttatcatgga ttctaaaacg gattaccagg gatttcagtc gatgtacacg    1020
ttcgtcacat ctcatctacc tcccggtttt aatgaatacg attttgtgcc agagtccttc    1080
gatagggaca agacaattgc actgatcatg aactcctctg gatctactgg tctgcctaaa    1140
ggtgtcgctc tgcctcatag aactgcctgc gtgagattct cgcatgccag agatcctatt    1200
tttggcaatc aaatcattcc ggatactgcg attttaagtg ttgttccatt ccatcacggt    1260
tttggaatgt ttactacact cggatatttg atatgtggat ttcgagtcgt cttaatgtat    1320
agatttgaag aagagctgtt tctgaggagc cttcaggatt acaagattca aagtgcgctg    1380
ctggtgccaa ccctattctc cttcttcgcc aaaagcactc tgattgacaa atacgattta    1440
tctaatttac acgaaattgc ttctggtggc gctcccctct ctaaggaagt cggggaagcg    1500
gttgccaaga ggttccatct gccaggtatc aggcaaggat atgggctcac tgagactaca    1560
tcagctattc tgattacacc cgagggggat gataaaccgg gcgcggtcgg taaagttgtt    1620
ccattttttg aagcgaaggt tgtggatctg gataccggga aaacgctggg cgttaatcaa    1680
agaggcgaac tgtgtgtgag aggtcctatg attatgtccg gttatgtaaa caatccggaa    1740
gcgaccaacg ccttgattga caaggatgga tggctacatt ctggagacat agcttactgg    1800
gacgaagacg aacacttctt catcgttgac cgcctgaagt ctctgattaa gtacaaaggc    1860
tatcaggtgg ctcccgctga attggaatcc atcttgctcc aacaccccaa catcttcgac    1920
gcaggtgtcg caggtcttcc cgacgatgac gccggtgaac ttcccgccgc cgttgttgtt    1980
ttggagcacg gaaagacgat gacggaaaaa gagatcgtgg attacgtcgc cagtcaagta    2040
acaaccgcaa aagttgcgc ggaggagttg tgtttgtgga cgaagtaccg aaaggtctta    2100
ccggaaaact cgacgcaaga aaaatcagag agatcctcat aaaggccaag aagggcggaa    2160
agatcgccgt gtaattggat ccagtttaaa cagtagcttt ggacttcttc gccagaggtt    2220
```

-continued

```
tggtcaagtc tccaatcaag gttgtcggct tgtctacctt gccagaaatt tacgaaaaga      2280
tggaaaaggg tcaaatcgtt ggtagatacg ttgttgacac ttctaaataa gcgaatttct      2340
tatgatttat gatttttatt attaaataag ttataaaaaa aataagtgta tacaaatttt      2400
aaagtgactc ttaggtttta aaacgaaaat tcttgttctt gagtaactct ttcctgtagg      2460
tcaggttgct ttctcaggta tagcatgagg tcgctcttat tgaccacacc tctaccggca      2520
tgccgagcaa atgcctgcaa atcgctcccc atttcaccca attgtagata tgctaactcc      2580
agcaatgagt tgatgaatct cggtgtgtat tttatgtcct cagaagacaa cacctgttgt      2640
aatcgttctt ccacacggat cgcggccgct tgatcctcta cgccggacgc atcgtggccg      2700
gcatcaccgg cgccacaggt gcggttgctg gcgcctatat cgccgacatc accgatgggg      2760
aagatcgggc tcgccacttc gggctcatga gcgcttgttt cggcgtgggt atggtggcag      2820
gccccgtggc cggggactg ttgggcgcca tctccttgca tgcaccattc cttgcggcgg       2880
cggtgctcaa cggcctcaac ctactactgg gctgcttcct aatgcaggag tcgcataagg      2940
gagagcgtcg accgatgccc ttgagagcct tcaacccagt cagctccttc cggtgggcgc      3000
ggggcatgac tatcgtcgcc gcacttatga ctgtcttctt tatcatgcaa ctcgtaggac      3060
aggtgccggc agcgctctgg gtcattttcg gcgaggaccg cttttcgctgg agcgcgacga      3120 tgatcggcct gtcgcttgcg gtattcggaa tcttgcacgc cctcgctcaa gccttcgtca      3180
ctggtcccgc caccaaacgt tcggcgaga agcaggccat tatcgccggc atggcggccg      3240
acgcgctggg ctacgtcttg ctggcgttcg cgacgcgagg ctggatggcc ttccccatta      3300
tgattcttct cgcttccggc ggcatcggga tgcccgcgtt gcaggccatg ctgtccaggc      3360
aggtagatga cgaccatcag ggacagcttc aaggatcgct cgcggctctt accagcctaa      3420
cttcgatcac tggaccgctg atcgtcacgg cgatttatgc cgcctcggcg agcacatgga      3480
acgggttggc atggattgta ggcgccgccc tataccttgt ctgcctcccc gcgttgcgtc      3540
gcggtgcatg gagccgggcc acctcgacct gaatggaagc cggcggcacc tcgctaacgg      3600
attcaccact ccaagaattg gagccaatca attcttgcgg agaactgtga atgcgcaaac      3660
caacccttgg cagaacatat ccatcgcgtc cgccatctcc agcagccgca cgcggcgcat      3720
ctcgggcagc gttgggtcct ggccacgggt gcgcatgatc gtgctcctgt cgttgaggac      3780
ccggctaggc tggcggggtt gccttactgg ttagcagaat gaatcaccga tacgcgagcg      3840
aacgtgaagc gactgctgct gcaaaacgtc tgcgacctga gcaacaacat gaatggtctt      3900
cggtttccgt gtttcgtaaa gtctggaaac gcggaagtca gcgccctgca ccattatgtt      3960
ccggatctgc atcgcaggat gctgctggct accctgtgga acacctacat ctgtattaac      4020
gaagcgctgg cattgaccct gagtgatttt tctctggtcc cgccgcatcc ataccgccag      4080
ttgtttaccc tcacaagttc cagtaaccgg gcatgttcat catcagtaac ccgtatcgtg      4140
agcatcctct ctcgtttcat cggtatcatt accccccatga acagaaattc ccccttacac      4200
ggaggcatca gtgaccaaa caggaaaaaa ccgcccttaa catggcccgc tttatcagaa      4260
gccagacatt aacgcttctg gagaaactca acgagctgga cgcggatgaa caggcagaca      4320
tctgtgaatc gcttcacgac cacgctgatg agctttaccg cagctgcctc gcgcgtttcg      4380
gtgatgacgg tgaaaacctc tgacacatgc agctcccgga cggtcaca gcttgtctgt      4440 aagcggatgc cgggagcaga caagcccgtc agggcgcgtc agcgggtgtt ggcgggtgtc      4500
ggggcgcagc catgacccag tcacgtagcg atagcggagt gtatactggc ttaactatgc      4560
```

-continued

```
ggcatcagag cagattgtac tgagagtgca cgatatccgg tgtgaaatac cgcacagatg    4620
cgtaaggaga aaataccgca tcaggcgctc ttccgcttcc tcgctcactg actcgctgcg    4680
ctcggtcgtt cggctgcggc gagcggtatc agctcactca aaggcggtaa tacggttatc    4740
cacagaatca ggggataacg caggaaagaa catgtgagca aaaggccagc aaaaggccag    4800
gaaccgtaaa aaggccgcgt tgctggcgtt tttccatagg ctccgccccc ctgacgagca    4860
tcacaaaaat cgacgctcaa gtcagaggtg gcgaaacccg acaggactat aaagatacca    4920
ggcgtttccc cctggaagct ccctcgtgcg ctctcctgtt ccgaccctgc cgcttaccgg    4980 ataccgtgtcc gcctttctcc cttcgggaag cgtggcgctt tctcaatgct cacgctgtag    5040
gtatctcagt tcggtgtagg tcgttcgctc caagctgggc tgtgtgcacg aaccccccgt    5100
tcagcccgac cgctgcgcct tatccggtaa ctatcgtctt gagtccaacc cggtaagaca    5160
cgacttatcg ccactggcag cagccactgg taacaggatt agcagagcga ggtatgtagg    5220
cggtgctaca gagttcttga agtggtggcc taactacggc tacactagaa ggacagtatt    5280
tggtatctgc gctctgctga agccagttac cttcggaaaa agagttggta gctcttgatc    5340
cggcaaacaa accaccgctg gtagcggtgg tttttttgtt tgcaagcagc agattacgcg    5400
cagaaaaaaa ggatctcaag aagatccttt gatcttttct acggggtctg acgctcagtg    5460
gaacgaaaac tcacgttaag ggattttggt catgagatta tcaaaaagga tcttcaccta    5520 gatccttta aattaaaaat gaagttttaa atcaatctaa agtatatatg agtaaacttg    5580
gtctgacagt taccaatgct taatcagtga ggcacctatc tcagcgatct gtctatttcg    5640
ttcatccata gttgcctgac tccccgtcgt gtagataact acgatacggg agggcttacc    5700
atctggcccc agtgctgcaa tgataccgcg agacccacgc tcaccggctc cagatttatc    5760
agcaataaac cagccagccg gaagggccga gcgcagaagt ggtcctgcaa ctttatccgc    5820
ctccatccag tctattaatt gttgccggga agctagagta agtagttcgc cagttaatag    5880
tttgcgcaac gttgttgcca ttgctgcagg catcgtggtg tcacgctcgt cgtttggtat    5940
ggcttcattc agctccggtt cccaacgatc aaggcgagtt acatgatccc ccatgttgtg    6000
caaaaaagcg gttagctcct tcggtcctcc gatcgttgtc agaagtaagt tggccgcagt    6060
gttatcactc atggttatgg cagcactgca taattctctt actgtcatgc catccgtaag    6120
atgcttttct gtgactggtg agtatcaacc aagtcattct gagaatagtg tatgcggcga    6180
ccgagttgct cttgcccggc gtcaacacgg gataataccg cgccacatag cagaacttta    6240
aaagtgctca tcattggaaa acgttcttcg ggcgaaaac tctcaaggat cttaccgctg    6300
ttgagatcca gttcgatgta acccactcgt gcacccaact gatcttcagc atcttttact    6360
ttcaccagcg tttctgggtg agcaaaaaca ggaaggcaaa atgccgcaaa aaagggaata    6420
agggcgacac ggaaatgttg aatactcata ctcttccttt ttcaatatta ttgaagcatt    6480
tatcagggtt attgtctcat gagcggatac atatttgaat gtatttagaa aaataaacaa    6540
ataggggttc cgcgcacatt tccccgaaaa gtgccacctg acgtctaaga aaccattatt    6600
atcatgacat taacctataa aaataggcgt atcacgaggc cctttcgtct tcaagaattc    6660
cacggactat agactatact agtatactcc gtctactgta cgatacactt ccgctcaggt    6720
ccttgtcctt taacgaggcc ttaccactct ttgttactc tattgatcca gctcagcaaa    6780
ggcagtgtga tctaagattc tatcttcgcg atgtagtaaa actagctaga ccgagaaaga    6840
gactagaaat gcaaaggca cttctacaat ggctgccatc attattatcc gatgtgacgc    6900
tgcagaagca gaaatacacg cggtcagtga agctattccg ctattgaata acctcagtca    6960
```

-continued

```
ccttgtgcaa gaacttaaca agaaaccaat tattaaaggc ttacttactg atagtagatc    7020
aacgatcagt ataattaagt ctacaaatga agagaaattt agaaacagat tttttggcac    7080
aaaggcaatg agacttagag atgaagtatc aggtaataat ttatacgtat actacatcga    7140
gaccaagaag aacattgctg atgtgatgac aaaacctctt ccgataaaaa catttaaact    7200
attaactaac aaatggattc attagatcta ttacattatg ggtggtatgt tggaataaaa    7260
atcaactatc atctactaac tagtatttac gttactagta tattatcata tacggtgtta    7320
gaagatgacg caaatgatga gaaatagtca tctaaattag tggaagctga aacgcaagga    7380
ttgataatgt aataggatca atgaatatta acatataaaa tgatgataat aatatttata    7440
gaattgtgta gaattgcaga ttccctttta tggattccta aatcctcgag gagaacttct    7500
agtatatcta catacctaat attattgcct tattaaaaat ggaatcccaa caattacatc    7560
aaaatccaca ttctcttcaa aatcaattgt cctgtacttc cttgttcatg tgtgttcaaa    7620
aacgttatat ttataggata attatactct atttctcaac aagtaattgg ttgtttggcc    7680
gagcggtcta aggcgcctga ttcaagaaat atcttgaccg cagttaactg tgggaatact    7740
caggtatcgt aagatgcaag agttcgaatc tcttagcaac cattattttt ttcctcaaca    7800
taacgagaac acacagggc gctatcgcac agaatcaaat tcgatgactg gaattttttt     7860
gttaatttca gaggtcgcct gacgcatata cctttttcaa ctgaaaaatt gggagaaaaa    7920
ggaaaggtga gagccgcgga accggctttt catatagaat agagaagcgt tcatgactaa    7980
atgcttgcat cacaatactt gaagttgaca atattattta aggacctatt gttttttcca    8040
ataggtggtt agcaatcgtc ttactttcta acttttctta cctttacat ttcagcaata    8100 tatatatata tatttcaagg atataccatt ctaatgtctg cccctaagaa gatcgtcgtt    8160
ttgccaggtg accacgttgg tcaagaaatc acgccgaagc cattaaggtt cttaaagcta    8220
tttctgatgt tcgttccaat gtcaagttcg atttcgaaaa tcatttaatt ggtggtgctg    8280
ctatcgatgc tacaggtgtc ccacttccag atgaggcgct ggaagcctcc aagaaggttg    8340
atgccgtttt gttaggtgct gtgggtggtc taaatgggg taccggtagt gttagacctg     8400
aacaaggttt actaaaaatc cgtaaagaac ttcaattgta cgccaactta agaccatgta    8460
actttgcatc cgactctctt ttagacttat ctccaatcaa gccacaattt gctaaagta     8520 ctgacttcgt tgttgtcaga gaattagtgg gaggtattta ctttggtaag agaaaggaag    8580
acgatggtga tggtgtcgct tgggatagtg aacaatacac cgttccagaa gtgcaaagaa    8640
tcacaagaat ggccgctttc atggccctac aacatgagcc accattgcct atttggtcct    8700
tggataaagc taatgttttg gcctcttcaa gattatggag aaaaactgtg gaggaaacca    8760
tcaagaacga attccctaca ttgaaggttc aacatcaatt gattgattct gccgccatga    8820
tcctagttaa gaacccaacc cacctaaatg gtattataat caccagcaac atgtttggtg    8880
atatcatctc cgatgaagcc tccgttatcc caggttcctt gggtttgttg ccatctgcgt    8940
ccttggcctc tttgccagac aagaacaccg catttggttt gtacgaacca tgccacggtt    9000
ctgctccaga tttgccaaag aataaggtca accctatcgc cactatcttg tctgctgcaa    9060
tgatgttgaa attgtcattg aacttgcctg aagaaggtaa ggccattgaa gatgcagtta    9120
aaaaggtttt ggatgcaggt atcagaactg gtgatttagg tggttccaac agtaccacgg    9180
aagtcggtga tgctgtcgcc gaagaagtta agaaaatcct tgcttaaaaa gattctcttt    9240
ttttatgata tttgtacata aactttataa atgaaattca taatagaaac gacacgaaat    9300
```

-continued

```
tacaaaatgg aatatgttca tagggtagac gaaactatat acgcaatcta catacattta   9360
tcaagaagga gaaaaggag gatgtaaagg aatacaggta agcaaattga tactaatggc    9420
tcaacgtgat aaggaaaaag aattgcactt taacattaat attgacaagg aggagggcac   9480
cacacaaaaa gttaggtgta acagaaaatc atgaaactat gattcctaat ttatatattg   9540
gaggattttc tctaaaaaaa aaaaaataca acaaataaaa aacactcaat gacctgacca   9600
tttgatggag tttaagtcaa taccttcttg aaccatttcc cataatggtg aaagttccct   9660
caagaattt actctgtcag aaacggcctt aacgacgtag tcgacctcct cttcagtact    9720
aaatctacca ataccaaatc tgatggaaga atgggctaat gcatcatcct acccagcgc    9780
atgtaaaaca taagaaggtt ctagggaagc agatgtacag gctgaacccg aggataatgc   9840
gatatcccctt agtgccatca ataaagattc tccttccacg taggcgaaag aaacgttaac  9900
acaccctgga taacgatgat ctggagatcc gttcaacgtg gtatgttcag cggataatag   9960
acctttgact aatttatcgg atagtctttt gatgtgagct tggtcgttgt caaattcttt  10020
cttcatcaat ctcgcagctt caccaaatcc cgctaccaat gggggggcca agtaccaga   10080
tctcaatcct ctctcttggc caccaccgga tagtaaaggt tctaatctaa ctcttggtct  10140
ccttcttaca tagatggcac ctattcccctt tggaccgtaa atcttgtgag aagaaattga  10200
tagtaaatca atgttcattt cattgacatc aatgtgaatc taccataggc ttgtgcggcg  10260
tcagtatgaa agtagatctt attctttcta caaattgcac caatttcttt aataggttga  10320
atgacaccga tttcattatt gacagccatc acagagacga gacaggtatc tggtctaatg  10380
gcatcttcca attccttcaa atcgataaga ccttgatcgt ccacatttag gaaagtgact  10440
tcaaatccct ccttcatcat ggcccgtgcg gcttccaaga cacacttgtg ttccgttcta  10500
gtggtgatga tgtgtttctt agtcttctta taaaatcttg ggacaccctt aagaaccata  10560
ttattagatt cggtcgctcc cgaagtgaat attatttcct tggggtcggc attgatcatc  10620
tttgctacgt aagctctagc attttccaca gcagtatttg tttcccaacc gtaagagtga  10680
gtgttggaat gaggattacc ataaagtccc gtataaaact tcaacatcgt atccaaaacc  10740
ctagggtctg ttggtgtagt ggcttgcatg tcaagatata tgggacgagt accaaaacct  10800
gtgttttctt gataagcatg gctcattgca gtgctaccag aagctactac agcatctggg  10860
gtggtaccgg atgcactcgc acgggcacta gcctgtgcct ttgcagcagc ctgaatatcg  10920
gtatgcgttt ccagagagaa gttgtcgtct aacttcacgc ctgctgcagt ctcaatgata  10980
ttcgaatacg ctttgaggag atacagccta atatccgaca aactgttta cagatttacg   11040
atcgtacttg ttaccatcat ttgaattttg aacatccgaa cctgggagtt tccctgaaa   11100
cagatagtat atttgaacct gtataataat atatagtcta gcgctttacg gaagacaatg  11160
tatgtatttc ggttcctgga gaaactattg catctattgc ataggtaatc ttgcacgtcg  11220
catcccccggt tcattttctg cgtttccatc ttgcacttca atagcatatc tttgttaacg  11280
aagcatctgt gcttcatttt gtagaacaaa aatgcaacgc gagagcgcta attttcaaa   11340
caaagaatct gagctgcatt tttacagaac agaaatgcaa cgcgaaagcg ctattttacc  11400
aacgaagaat ctgtgcttca tttttgtaaa acaaaaatgc aacgcgagag cgctaatttt  11460
tcaaacaaag aatctgagct gcattttttac agaaacagaaa tgcaacgcga gagcgctatt  11520
ttaccaacaa agaatctata cttcttttt gttctacaaa aatgcatccc gagagcgcta  11580
tttttctaac aaagcatctt agattacttt ttttctcctt tgtgcgctct ataatgcagt  11640
ctcttgataa cttttttgcac tgtaggtccg ttaaggttag aagaaggcta ctttggtgtc  11700
```

```
tattttctct tccataaaaa aagcctgact ccacttcccg cgtttactga ttactagcga  11760
agctgcgggt gcatttttc aagataaagg catccccgat tatattctat accgatgtgg  11820
attgcgcata ctttgtgaac agaaagtgat agcgttgatg attcttcatt ggtcagaaaa  11880
ttatgaacgg tttcttctat tttgtctcta tatactacgt ataggaaatg tttacatttt  11940
cgtattgttt tcgattcact ctatgaatag ttcttactac aattttttg tctaaagagt  12000 aatactagag ataaacataa aaaatgtaga ggtcgagttt agatgcaagt tcaaggagcg  12060
aaaggtggga gggtaggtta tagggata tagcacagag atatatagca aagagatact  12120
tttgagcaat gtttgtggaa gcggtattcg caatatttta gtagctcgtt acagtccggt  12180 gcgttttgg ttttttgaaa gtgcgtcttc agagcgcttt tggttttcaa aagcgctctg  12240
aagttcctat actttctaga gaataggaac ttcggaatag gaacttcaag cgtttccgaa  12300
aacgagcgct tccgaaaatg caacgcgagc tgcgcacata cagctcactg ttcacgtcgc  12360
acctatatct gcgtgttgcc tgtatatata tatacatgag aagaacggca tagtgcgtgt  12420
ttatgcttaa atgcgtactt atatgcgtct atttatgtag gatgaaaggt agtctagtac  12480
ctcctgtgat attatcccat tccatgcggg gtatcgtatg cttccttcag cactacccct  12540
tagctgttct atatgctgcc actcctcaat tggattagtc tcatccttca atgctatcat  12600
ttcctttgat attcgatcct aggcatagta ccgagaaact agtgcgaagt agtgatcagg  12660
tattgctgtt atctgatgag tatacgttgt cctggccacg gcagaagcac gcttatcgct  12720
ccaatttccc acaacattag tcaactccgt taggccctttc attgaaagaa atgaggtcat  12780
caaatgtctt ccaatgtgag attttgggcc atttttata gcaaagattg ataaggcgc   12840 attttttcttc a                                                     12851
```

<210> SEQ ID NO 22
<211> LENGTH: 12850
<212> TYPE: DNA
<213> ORGANISM: Saccharomyces cerevisiae

<400> SEQUENCE: 22

```
aagcttcgcg gccgcggagg tctgcttcac gagcgcggtg tgcgcctagt attgccccga   60
cggtccgggt gcctatccct agatttcgtc gtgccccgac ccaaatagtt aaacgtgtgg  120
tttatgggtg caccagggct ttatcgtgtt ttatatcgat ggcgatttgt gcctccagtg  180
tattttttgta tatccaatta aggtttctta cctaatttta ttttttatcat ctttagttaa  240
tgctggttg ctctgttttct gctgcttct gtgcggttct cctcttctcg tgtttcttcg   300
tgttgtcccc catcgccgat gggcttatat ggcgtatata tatagagcga gttttttacgt  360
cgaagatcat ctcagtttgc ttgatagcct ttctacttta ttactttcgt ttttaacctc  420
attatacttt agttttcttt gatcggtttt tttctctgta tacttaaaag ttcaaatcaa  480
agaaacatac aaaactacgt ttatatcaat tacatatgaa agacgccaaa aacataaaga  540
aaggcccggc gccattctat ccgctggaag atgaaccgc tggagagcaa ctgcataagg  600
ctatgaagag atacgccctg gttcctggaa caattgcttt tacagatgca catatcgagg  660
tggacatcac ttacgctgag tacttcgaaa tgtccgttcg gttggcagaa gctatgaaac  720
gatatgggct gaatacaaat cacagaatcg tcgtatgcag tgaaaactct cttcaattct  780
ttatgccggt gttgggcgcg ttatttatcg gagttgcagt tgcgcccgcg aacgacattt  840
ataatgaacg tgaattgctc aacagtatgg gcatttcgca gcctaccgtg gtgttcgttt  900
ccaaaaaggg gttgcaaaaa attttgaacg tgcaaaaaaa gctcccaatc atccaaaaaa  960
ttattatcat ggattctaaa acggattacc agggatttca gtcgatgtac acgttcgtca 1020
catctcatct acctcccggt tttaatgaat acgatttgt gccagagtcc ttcgataggg 1080
acaagacaat tgcactgatc atgaactcct ctggatctac tggtctgcct aaaggtgtcg 1140
ctctgcctca tagaactgcc tgcgtgagat tctcgcatgc cagagatcct attttttggca 1200
atcaaatcat tccggatact gcgattttaa gtgttgttcc attccatcac ggttttggaa 1260
tgtttactac actcggatat ttgatatgtg gatttcgagt cgtcttaatg tatagatttg 1320
aagaagagct gtttctgagg agccttcagg attacaagat tcaaagtgcg ctgctggtgc 1380
caacccctat ctccttcttc gccaaaagca ctctgattga caaatacgat ttatctaatt 1440
tacacgaaat tgcttctggt ggcgctcccc tctctaagga agtcggggaa gcggttgcca 1500
agaggttcca tctgccaggt atcaggcaag atatggggct cactgagact acatcagcta 1560
ttctgattac acccgagggg gatgataaac cgggcgcggt cggtaaagtt gttccatttt 1620
tgaagcgaag gttgtggat ctggataccg gaaaacgct gggcgttaat caaagaggcg 1680
aactgtgtgt gagaggtcct atgattatgt ccggttatgt aaacaatccg gaagcgacca 1740
acgccttgat tgacaaggat ggatggctac attctggaga catagcttac tgggacgaag 1800
```

```
acgaacactt cttcatcgtt gaccgcctga agtctctgat taagtacaaa ggctatcagg 1860
tggctcccgc tgaattggaa tccatcttgc tccaacaccc caacatcttc gacgcaggtg 1920
tcgcaggtct tcccgacgat gacgccgtga aacttcccgc cgccgttgtt gttttggagc 1980
acggaaagac gatgacggaa aaagaaatcg tggattacgt cgccagtcaa gtaacaaccg 2040
cgaaaaagtt gcgcggagga gttgtgtttg tggacgaagt accgaaaggt cttaccggaa 2100
aactcgacgc aagaaaaatc agagagatcc tcataaaggc caagaagggc ggaaagatcg 2160
ccgtgtaatt ggatccagtt taaacagtag cttttggactt cttcgccaga ggtttggtca 2220
agtctccaat caaggttgtc ggcttgtcta ccttgccaga aatttacgaa aagatggaaa 2280
agggtcaaat cgttggtaga tacgttgttg acacttctaa ataagcgaat ttcttatgat 2340
ttatgatttt tattattaaa taagttataa aaaaaataag tgtatacaaa ttttaaagtg 2400
actcttaggt ttaaaacga aaattcttgt tcttgagtaa ctctttcctg taggtcaggt 2460
tgctttctca ggtatagcat gaggtcgctc ttattgacca cacctctacc ggcatgccga 2520
gcaaatgcct gcaaatcgct ccccatttca cccaattgta gatatgctaa ctccagcaat 2580
gagttgatga atctcggtgt gtattttatg tcctcagaag acaacacctg ttgtaatcgt 2640
tcttccacac ggatcgcggc cgcttgatcc tctacgccgg acgcatcgtg gccggcatca 2700
ccggcgccac aggtgcggtt gctggcgcct atatcgccga catcaccgat ggggaagatc 2760
gggctcgcca cttcgggctc atgagcgctt gtttcggcgt gggtatggtg gcaggccccg 2820
tggccggggg actgttgggc gccatctcct tgcatgcacc attccttgcg gcggcggtgc 2880
tcaacggcct caacctacta ctgggctgct tcctaatgca ggagtcgcat aagggagagc 2940
gtcgaccgat gcccttgaga gccttcaacc cagtcagctc cttccggtgg gcgcggggca 3000
tgactatcgt cgccgcactt atgactgtct tcttttatcat gcaactcgta ggacaggtgc 3060
cggcagcgct ctgggtcatt ttcggcgagg accgctttcg ctggagcgcg acgatgatcg 3120
gcctgtcgct tgcggtattc ggaatcttgc acgccctcgc tcaagccttc gtcactggtc 3180
ccgccaccaa acgtttcggc gagaagcagg ccattatccg cggcatggcg gccgacgcgc 3240
tgggctacgt cttgctggcg ttcgcgacgt gaggctgcct gccttcccc attatgattc 3300
ttctcgcttc cggcggcatc gggatgcccg cgttgcaggc catgctgtcc aggcaggtag 3360
atgacgacca tcaggacag cttcaaggat cgctcgcggc tcttaccagc ctaacttcga 3420
tcactggacc gctgatcgtc acggcgattt atgccgcctc ggcgagcaca tggaacgggt 3480
tggcatggat tgtaggcgcc gccctatacc ttgtctgcct cccgcgttg cgtcgcggtg 3540
catggagccg ggccacctcg acctgaatgg aagccggcgg cacctcgcta acggattcac 3600
cactccaaga attggagcca atcaattctt gcggagaact gtgaatgcgc aaaccaaccc 3660
ttggcagaac atatccatcg cgtccgccat ctccagcagc gcacgcggc gcatctcggg 3720
cagcgttggg tcctggccac gggtgcgcat gatcgtcctc ctgtcgttga ggacccggtt 3780
aggctggcgg ggttgcctta ctggttagca gaatgaatca ccgatacgcg acgaacgtga 3840
aagcgactgc tgctgcaaaa cgtctgcgac ctgagcaaca acatgaatgg tcttcggttt 3900
ccgtgtttcg taaagtctgg aaacgcggaa gtcagcgccc tgcaccatta tgttccggat 3960
ctgcatcgca ggatgctgct ggctaccctg tggaacacct acatctgtat taacgaagcg 4020
ctggcattga ccctgagtga ttttttctctg gtcccgccgc atccataccg ccagttgttt 4080
accctcacaa cgttccagta accgggcatg ttcatcatca gtaacccgta tcgtgagcat 4140
cctctctcgt ttcatcggta tcattacccc catgaacaga aattcccct tacacggagg 4200
catcaagtga ccaaacagga aaaaaccgcc cttaacatgg cccgctttat cagaagccag 4260
acattaacgc ttctggagaa actcaacgag ctggacgcgg atgaacaggc agacatctgt 4320
gaatcgcttc acgaccacgc tgatgagctt taccgcagct gcctcgcgcg tttcggtgat 4380
gacggtgaaa acctctgaca catgcagctc ccggagacgg tcacagcttg tctgtaagcg 4440
gatgccggga gcagacaagc ccgtcagggc gcgtcagcgg gtgttggcgg gtgtcgggc 4500
gcagccatga cccagtacg tagcgatagc ggagtgtata ctggcttaac tatgcggcat 4560
cagagcagat tgtactgaga gtgcacgata tccggtgtga aataccgcac agatgcgtaa 4620
ggagaaaata ccgcatcagg cgctcttccg cttcctcgct cactgactcg ctgcgctcgg 4680
tcgttcggct gcggcgagcg gtatcagctc actcaaaggc ggtaatacgg ttatccacag 4740
aatcagggga taacgcagga aagaacatgt gagcaaaagg ccagcaaaag gccaggaacc 4800
gtaaaaaggc cgcgttgctg gcgtttttcc ataggctccg ccccctgac gagcatcaca 4860
aaaatcgacg ctcaagtcag aggtggcgaa acccgacagg actataaaga taccaggcgt 4920
ttccccctgg aagctccctc gtgcgctctc ctgttccgac cctgccgctt accggatacc 4980
tgtccgcctt tctcccttcg ggaagcgtgg cgctttctca atgctcacgc tgtaggtatc 5040
tcagttcggt gtaggtcgtt cgctccaagc tgggctgtgt gcacgaaccc cccgttcagc 5100
ccgaccgctg cgccttatcc ggtaactatc gtcttgagtc aacccggta agacacgact 5160
tatcgccact ggcagcagcc actggtaaca ggattagcag agcgaggtat gtaggcggtg 5220
ctacagagtt cttgaagtgg tggcctaact acggctacac tagaaggaca gtatttggta 5280
tctgcgctct gctgaagcca gttaccttcg gaaaaagagt tggtagctct tgatccggca 5340
aacaaaccac cgctggtagc ggtggttttt tgtttgcaa gcagcagatt acgcgcagaa 5400
aaaaaggatc tcaagaagat cctttgatct ttttctacggg gtctgacgct cagtggaacg 5460
aaaactcacg ttaagggatt ttggtcatga gattatcaaa aaggatctta acctagatcc 5520
ttttaaatta aaaatgaagt tttaaatcaa tctaaagtat atatgagtaa acttggtctg 5580
acagttacca atgcttaatc agtgaggcac ctatctcagc gatctgtcta tttcgttcat 5640
ccatagttgc ctgactcccc gtcgtgtaga taactacgat acgggagggc ttaccatctg 5700
gccccagtgc tgcaatgata ccgcgagacc cacgctcacc ggctccagat ttatcagcaa 5760
taaaccagcc agccggaagg gccgagcgca gaagtggtcc tgcaacttta tccgcctcca 5820
tccagtctat taattgttgc cgggaagcta gagtaagtag ttcgcagtt aatagtttgc 5880
gcaacgttgt tgccattgct gcaggcatcg tggtgtcacg ctcgtcgttt ggtatggctt 5940
cattcagctc cggttcccaa cgatcaaggc gagttacatg atcccccatg ttgtgcaaaa 6000
aagcggttag ctccttcggt cctccgatcg ttgtcagaag taagttggcc gcagtgttat 6060
cactcatggt tatggcagca ctgcataatt ctcttactgt catgccatcc gtaagatgct 6120
tttctgtgac tggtgagtac tcaaccaagt cattctgaga atagtgtatg cggcgaccga 6180
gttgctcttg cccggcgtca acacgggata ataccgcgcc acatagcaga actttaaaag 6240
tgctcatcat tggaaaacgt tcttcgggc gaaaactctc aaggatctta ccgctgttga 6300
gatccagttc gatgtaaccc actcgtgcac ccaactgatc ttcagcatct tttactttca 6360
ccagcgtttc tgggtgagca aaaacaggaa ggcaaaatgc cgcaaaaaag ggaataaggg 6420
cgacacggaa atgttgaata ctcatactct tcctttttca atattattga agcatttatc 6480
agggttattg tctcatgagc ggatacatat ttgaatgtat ttagaaaaat aaacaaatag 6540
```

```
gggttccgcg cacatttccc cgaaaagtgc cacctgacgt ctaagaaacc attattatca 6600
tgacattaac ctataaaaat aggcgtatca cgaggcccct tcgtcttcaa gaattccacg 6660
gactatagac tatactagta tactccgtct actgtacgat acacttccgc tcaggtcctt 6720
gtcctttaac gaggccttac cactctttg ttactctatt gatccagctc agcaaaggca 6780
gtgtgatcta agattctatc ttcgcgatgt agtaaaacta gctagaccga gaaagagact 6840
agaaatgcaa aaggcacttc tacaatggct gccatcatta ttatccgatg tgacgctgca 6900
gaagcagaaa tacacgcggt cagtgaagct attccgctat tgaataacct cagtcacctt 6960
gtgcaagaac ttaacaagaa accaattatt aaaggcttac ttactgatag tagatcaacg 7020
atcagtataa ttaagtctac aaatgaagag aaatttagaa acagattttt tggcacaaag 7080
gcaatgagac ttagagatga agtatcaggt aataatttat acgtatacta catcgagacc 7140
aagaagaaca ttgctgatgt gatgacaaaa cctcttccga taaaaacatt taaactatta 7200
actaacaaat ggattcatta gatctattac attatgggtg gtatgttgga ataaaaatca 7260
actatcatct actaactagt atttacgtta ctagtatatt atcatatacg gtgttagaag 7320
atgacgcaaa tgatgagaaa tagtcatcta aattagtgga agctgaaacg caaggattga 7380
taatgtaata ggatcaatga atattaacat ataaaatgat gataataata tttatagaat 7440
tgtgtagaat tgcagattcc cttttatgga ttcctaaatc ctcgaggaga acttctagta 7500
tatctacata cctaatatta ttgccttatt aaaaatggaa tcccaacaat tacatcaaaa 7560
tccacattct cttcaaaatc aattgtcctg tacttccttg ttcatgtgtg ttcaaaaacg 7620
ttatatttat aggataatta tactctattt ctcaacaagt aattggttgt ttggccgagc 7680
ggtctaaggc gcctgattca agaaatatct tgaccgcagt taactgtggg aatactcagg 7740
tatcgtaaga tgcaagagtt cgaatctctt agcaaccatt atttttttcc tcaacataac 7800
gagaacacac aggggcgcta tcgcacagaa tcaaattcga tgactggaaa ttttttgtta 7860
atttcagagg tcgcctgacg catataccct ttcaactga aaaattggga gaaaaggaa 7920
aggtgagagc cgcggaaccg gcttttcata tagaatagag aagcgttcat gactaaatgt 7980
ttgcatcaca atacttgaag ttgacaatat tatttaagga cctattgtt tttccaatag 8040
gtggttagca atcgtcttac tttctaactt ttcttaccctt ttacatttca gcaatatata 8100
tatatatatt tcaaggatat accattctaa tgtctgcccc taagaagatc gtcgttttgc 8160
caggtgacca cgttggtcaa gaaatcacag ccgaagccat taaggttctt aaagctattt 8220
ctgatgttcg ttccaatgtc aagttcgatt tcgaaaatca tttaattggt ggtgctgcta 8280
tcgatgctac agtgtcccca cttccagatg aggcgctgga agcctccaag aaggttgatg 8340
ccgttttgtt aggtgctgtg ggtggtccta atggggtac cggtagtgtt agacctgaac 8400
aaggtttact aaaaatccgt aaagaacttc aattgtacgc caacttaaga ccatgtaact 8460
ttgcatccga ctctctttta gacttatctc caatcaagcc acaatttgct aaaggtactg 8520
acttcgttgt tgtcagagaa ttagtgggag gtatttactt tggtaagaga aaggaagacg 8580
atggtgatgg tgtcgcttgg gatagtgaac aatacaccgt tccagaagtg caaagaatca 8640
caagaatggc cgctttcatg gccctacaac atgagccacc attgcctatt tggtccttgg 8700
ataaagctaa tgttttggcc tcttcaagat tatggagaaa aactgtggag gaaaccatca 8760
agaacgaatt ccctacattg aaggttcaac atcaattgat tgattctgcc gccatgatcc 8820
tagttaagaa cccaacccac ctaaatggta ttataatcac cagcaacatg tttggtgata 8880
tcatctccga tgaagcctcc gttatcccag gttccttggg tttgttgcca tctgcgtcct 8940
tggcctcttt gccagacaag aacaccgcat ttggtttgta cgaaccatgc acggttctg 9000
ctccagattt gccaaagaat aaggtcaacc ctatcgccac tatcttgtct gctgcaatga 9060
tgttgaaatt gtcattgaac ttgcctgaag aggtaaggc cattgaagat gcagttaaaa 9120
aggttttgga tgcaggtatc agaactggtg atttaggtgg ttccaacagt accacggaag 9180
tcggtgatgc tgtcgccgaa gaagttaaga aattccttgc ttaaaaagat tctctttttt 9240
tatgatattt gtacataaac tttataaatg aaattcataa tagaaacgac acgaaattac 9300
aaaatggaat atgttcatag ggtagacgaa actatatacg caatctacat acatttatca 9360
agaaggagaa aaaggaggat gtaaaggaat acaggtaagc aaattgatac taatggctca 9420
acgtgataag gaaaaagaat tgcactttaa cattaatatt gacaaggagg agggcaccac 9480
acaaaaagtt aggtgtaaca gaaaatcatg aaactatgat tcctaattta tatattggag 9540
gattttctct aaaaaaaaaa aaatacaaca aataaaaaac actcaatgac ctgaccatttt 9600
gatggagttt aagtcaatac cttcttgaac catttcccat aatggtgaaa gttccctcaa 9660
gaatttact ctgtcagaaa cggccttaac gacgtagtcg acctcctctt cagtactaaa 9720
tctaccaata ccaaatctga tggaagaatg ggctaatgca tcatccttac ccagcgcatg 9780
taaaacataa gaaggttcta gggaagcaga tgtacaggct gaacccgagg ataatgcgat 9840
atcccttagt gccatcaata aagattctcc ttccacgtag gcgaaagaaa cgttaacaca 9900
ccctggataa cgatgatctg gagatccgtt caacgtggta tgttcagcgg ataatagacc 9960
tttgactaat ttatcggata gtcttttgat gtgagcttgg tcgttgtcaa attcttttctt 10020
catcaatctc gcagcttcac caaatcccgc taccaatggg ggggccaaag taccagatct 10080
caatcctctc tcttggccac caccggatag taaaggttct aatctaactc ttggtctcct 10140
tcttacatag atgcaccta ttccctttgg accgtaaatc ttgtgagaag aaattgatag 10200
taaatcaata ttcattcat tgacatcaat gtgaatctta ccataggctt gtgcggcgtc 10260
agtatgaaag tagatcttat tctttctaca aattgcacca attctcttaa taggttgaat 10320
gacaccgatt tcattattga cagccatcac agagacgaga caggtatctg gtctaatggc 10380
atcttccaat tccttcaaat cgataagacc ttgatcgtcc acatttagga aagtgacttc 10440
aaatccctcc ttcatcatgg cccgtgcggc ttccaagaca cacttgtgtt ccgttctagt 10500
ggtgatgatg tgtttcttag tcttcttata aaatcttggg acaccccttaa gaaccatatt 10560
attagattcg gtcgctcccg aagtgaatat tatttccttg gggtcggcat tgatcatctt 10620
tgctacgtaa gctctagcat tttccacagc agtatttgtt tcccaaccgt aagagtgagt 10680
gttggaatga ggattaccat aaagtcccgt ataaaacttc aacatcgtat ccaaaaccct 10740
agggtctgtt ggtgtagtgg cttgcatgtc aagatatatg ggacagtac caaaacctgt 10800
gttttcttga taagcatggc tcattgcagt gctaccagaa gctactacag catctggggt 10860
ggtaccggat gcactcgcac gggcactagc ctgtgccttt gcagcagcct gaatatcggt 10920
atgcgtttcc agagagaagt tgtcgtctaa cttcacgcct gctgcagtct caatgatatt 10980
cgaatacgct ttgaggagat acagcctaat atccgacaaa ctgttttaca gatttacgat 11040
cgtacttgtt acccatcatt gaattttgaa catccgaacc tgggagtttt ccctgaaaca 11100
gatagtatat ttgaacctgt ataataatat atagtctagc gctttacgga agacaatgta 11160
tgtatttcgg ttcctggaga aactattgca tctattgcat aggtaatctt gcacgtcgca 11220
tccccggttc attttctgcg tttccatctt gcacttcaat agcatatctt tgttaacgaa 11280
```

-continued

```
gcatctgtgc ttcattttgt agaacaaaaa tgcaacgcga gagcgctaat ttttcaaaca  11340
aagaatctga gctgcatttt tacagaacag aaatgcaacg cgaaagcgct attttaccaa  11400
cgaagaatct gtgcttcatt tttgtaaaac aaaaatgcaa cgcgagagcg ctaattttc   11460
aaacaaagaa tctgagctgc attttacag aacagaaatg cacgcgaga gcgctatttt   11520
accaacaaag aatctatact tcttttttgt tctacaaaaa tgcatcccga gagcgctatt  11580
tttctaacaa agcatcttag attactttt ttctcctttg tgcgctctat aatgcagtct   11640
cttgataact ttttgcactg taggtccgtt aaggttagaa aaggctact ttggtgtcta   11700
ttttctcttc cataaaaaaa gcctgactcc acttcccgcg tttactgatt actagcgaag  11760
ctgcgggtgc attttttcaa gataaaggca tccccgatta tattctatac cgatgtggat  11820
tgcgcatact ttgtgaacag aaagtgatag cgttgatgat tcttcattgg tcagaaaatt  11880
atgaacggtt tcttctattt tgtctctata tactacgtat aggaaatgtt tacattttcg  11940
tattgttttc gattcactct atgaatagtt cttactacaa ttttttttgtc taaagagtaa  12000
tactagagat aaacataaaa aatgtagagg tcgagtttag atgcaagttc aaggagcgaa  12060
aggtggatgg gtaggttata tagggatata gcacagagat atatagcaaa gagatacttt  12120
tgagcaatgt ttgtggaagc ggtattcgca atattttagt agctcgttac agtccggtgc  12180
gttttttggtt ttttgaaagt gcgtcttcag agcgcttttg gttttcaaaa gcgctctgaa  12240
gttcctatac tttctagaga ataggaactt cggaatagga acttcaaagc gtttccgaaa  12300
acgagcgctt ccgaaaatgc aacgcgagct gcgcacatac agctcactgt tcacgtcgca  12360
cctatatctg cgtgttgcct gtatatatat atacatgaga agaacggcat agtgcgtgtt  12420
tatgcttaaa tgcgtactta tatgcgtcta tttatgatg atgaaaggta gtctagtacc   12480
tcctgtgata ttatcccatt ccatgcgggg tatcgtatgc ttccttcagc actacccttt  12540
agctgttcta tatgctgcca ctcctcaatt ggattagtct catccttcaa tgctatcatt  12600
tcctttgata ttcgatccta ggcatagtac cgagaaacta gtgcgaagta gtgatcaggt  12660
attgctgtta tctgatgagt atacgttgtc ctggccacgg cagaagcacg cttatcgctc  12720
caatttccca caacattagt caactccgtt aggcccttca ttgaaagaaa tgaggtcatc  12780
aaatgtcttc caatgtgaga ttttgggcca ttttttatag caaagattga ataaggcgca  12840
tttttcttca                                                          12850
```

<210> SEQ ID NO 23
<211> LENGTH: 11198
<212> TYPE: DNA
<213> ORGANISM: Saccharomyces cerevisiae

<400> SEQUENCE: 23

```
agcttcgcgg ccgccgtctg atttccgttt tgggaatcct ttgccgcgcg cccctctcaa    60
aactccgcac aagtcccaga aagcgggaaa gaaataaaac gccaccaaaa aaaaaaaaat  120
aaaagccaat cctcgaagcg tgggtggtag gccctggatt atcccgtaca agtatttctc   180
aggagtaaaa aaaccgtttg ttttggaatt ccccatttcg cggccaccta cgccgctatc   240
tttgcaacaa ctatctgcga taactcagca aattttgcat attcgtgttg cagtattgcg   300
ataatgggag tcttactccc aacataacgg cagaaagaaa tgtgagaaaa ttttgcatcc   360
tttgcctccg ttcaagtata taagtcggc atgcttgata atctttcttt ccatcctaca   420
ttgttctaat tattcttatt ctcctttatt ctttcctaac ataccaagaa attaatcttc   480
tgtcattcgc ttaaacacta tatcacatat gcggtccgga tccagtttaa acagtagctt   540
tggacttctt cgccagaggt ttggtcaagt ctccaatcaa ggttgtcggc ttgtctacct   600
tgccagaaat ttacgaaaag atggaaaagg gtcaaatcgt tggtagatac gttgttgaca   660
cttctaaata agcgaatttc ttatgatta tgatttttat tattaaataa gttataaaaa   720
aaataagtgt atacaaattt taaagtgact cttaggtttt aaaacgaaaa ttcttgttct   780
tgagtaactc tttcctgtag gtcaggttgc tttctcaggt atagcatgag gtcgctctta   840
ttgaccacac ctctaccggc atgccagca aatgcctgca aatcgctccc catttcaccc   900
aattgtagat atgctaactc cagcaatgag ttgatgaatc tcggtgtgta ttttatgtcc   960
tcagaagaca acacctgttg taatcgttct tccacacgga tcgcggccgc ttgatcctct  1020
acgccggacg catcgtggcc ggcatcaccg gcgccacagg tgcggttgct ggcgcctata  1080
tcgccgacat caccgatggg gaagatcggg ctcgccactt cgggctcatg agcgcttgtt  1140
tcggcgtggg tatggtggca ggccccgtgg ccgggggact gttgggcgcc atctccttgc  1200
atgcaccatt ccttgcggcg gcggtgctca acggcctcaa cctactactg ggctgcttcc  1260
taatgcagga gtcgcataag ggagagcgtc gaccgatgcc cttgagagcc ttcaacccag  1320
```

-continued

```
tcagctcctt ccggtgggcg cggggcatga ctatcgtcgc cgcacttatg actgtcttct   1380
ttatcatgca actcgtagga caggtgccgg cagcgctctg ggtcatttc ggcgaggacc    1440
gctttcgctg gagcgcgacg atgatcggcc tgtcgcttgc ggtattcgga atcttgcacg   1500
ccctcgctca agccttcgtc actggtcccg ccaccaaacg tttcggcgag aagcaggcca   1560
ttatcgccgg catggcggcc gacgcgctgg gctacgtctt gctggcgttc gcgacgcgag   1620
gctggatggc cttccccatt atgattcttc tcgcttccgg cggcatcggg atgcccgcgt   1680
tgcaggccat gctgtccagg caggtagatg acgaccatca gggacagctt caaggatcgc   1740
tcgcggctct taccagccta acttcgatca ctggaccgct gatcgtcacg gcgatttatg   1800
ccgcctcggc gagcacatgg aacgggttgg catggattgt aggcgccgcc ctataccttg   1860
tctgcctccc cgcgttgcgt cgcggtgcat ggagccgggc cacctcgacc tgaatggaag   1920
ccggcggcac ctcgctaacg gattcaccac tccaagaatt ggagccaatc aattcttgcg   1980
gagaactgtg aatgcgcaaa ccaacccttg gcagaacata tccatcgcgt ccgccatctc   2040
cagcagccgc acgcggcgca tctcgggcag cgttgggtcc tggccacggg tgcgcatgat   2100
cgtgctcctg tcgttgagga cccggctagg ctggcggggt tgccttactg gttagcagaa   2160
tgaatcaccg atacgcgagc gaacgtgaag cgactgctgc tgcaaaacgt ctgcgacctg   2220
agcaacaaca tgaatggtct tcggtttccg tgtttcgtaa agtctggaaa cgcggaagtc   2280
agcgccctgc accattatgt tccggatctg catcgcagga tgctgctggc taccctgtgg   2340
aacacctaca tctgtattaa cgaagcgctg gcattgaccc tgagtgattt ttctctggtc   2400
ccgccgcatc cataccgcca gttgtttacc ctcacaacgt tccagtaacc gggcatgttc   2460
atcatcagta cccgtatcg tgagcatcct ctctcgtttc atcggtatca ttaccccat    2520
gaacagaaat tcccccttac acggaggcat caagtgacca aacaggaaaa aaccgccctt   2580
aacatggccc gctttatcag aagccagaca ttaacgcttc tggagaaact caacgagctg   2640
gacgcggatg aacaggcaga catctgtgaa tcgcttcacg accacgctga tgagctttac   2700
cgcagctgcc tcgcgcgttt cggtgatgac ggtgaaaacc tctgacacat gcagctcccg   2760
gagacggtca cagcttgtct gtaagcggat gccgggagca gacaagcccg tcagggcgcg   2820
tcagcgggtg ttggcgggtg tcggggcgca gccatgaccc agtcacgtag cgatagcgga   2880
gtgtatactg gcttaactat gcggcatcag agcagattgt actgagagtg cacgatatcc   2940
ggtgtgaaat accgcacaga tgcgtaagga gaaaataccg catcaggcgc tcttccgctt   3000
cctcgctcac tgactcgctg cgctcggtcg ttcggctgcg gcgagcggta tcagctcact   3060
caaaggcggt aatacggtta ccacagaat cagggggataa gcaggaaag aacatgtgag   3120
caaaaggcca gcaaaaggcc aggaaccgta aaaaggccgc gttgctggcg ttttccata   3180
ggctccgccc cctgacgag catcacaaaa atcgacgctc aagtcagagg tggcgaaacc   3240
cgacaggact ataaagatac caggcgtttc ccctggaag ctccctcgtg cgctctcctg   3300
ttccgaccct gccgcttacc ggatacctgt ccgcctttct cccttcggga agcgtggcgc   3360
tttctcaatg ctcacgctgt aggtatctca gttcggtgta ggtcgttcgc tccaagctgg   3420
gctgtgtgca cgaaccccc gttcagccg accgctgcgc cttatccggt aactatcgtc   3480
ttgagtccaa cccggtaaga cacgacttat cgccactggc agcagccact ggtaacagga   3540
ttagcagagc gaggtatgta ggcggtgcta cagagttctt gaagtggtgg cctaactacg   3600
gctacactag aaggacagta tttggtatct gcgctctgct gaagccagtt accttcggaa   3660
```

```
aaagagttgg tagctcttga tccggcaaac aaaccaccgc tggtagcggt ggttttttg    3720 tttgcaagca gcagattacg cgcagaaaaa aaggatctca agaagatcct ttgatctttt    3780
ctacggggtc tgacgctcag tggaacgaaa actcacgtta agggattttg gtcatgagat    3840
tatcaaaaag gatcttcacc tagatccttt taaattaaaa atgaagtttt aaatcaatct    3900
aaagtatata tgagtaaact tggtctgaca gttaccaatg cttaatcagt gaggcaccta    3960
tctcagcgat ctgtctattt cgttcatcca tagttgcctg actccccgtc gtgtagataa    4020
ctacgatacg ggagggctta ccatctggcc ccagtgctgc aatgataccg cgagacccac    4080
gctcaccggc tccagattta tcagcaataa accagccagc cggaagggcc gagcgcagaa    4140
gtggtcctgc aactttatcc gcctccatcc agtctattaa ttgttgccgg gaagctagag    4200
taagtagttc gccagttaat agtttgcgca acgttgttgc cattgctgca ggcatcgtgg    4260
tgtcacgctc gtcgtttggt atggcttcat tcagctccgg ttcccaacga tcaaggcgag    4320
ttacatgatc ccccatgttg tgcaaaaaag cggttagctc cttcggtcct ccgatcgttg    4380
tcagaagtaa gttggccgca gtgttatcac tcatggttat ggcagcactg cataattctc    4440
ttactgtcat gccatccgta agatgctttt ctgtgactgg tgagtactca accaagtcat    4500
tctgagaata gtgtatgcgg cgaccgagtt gctcttgccc ggcgtcaaca cgggataata    4560
ccgcgccaca tagcagaact ttaaaagtgc tcatcattgg aaaacgttct cggggcgaa     4620 aactctcaag gatcttaccg ctgttgagat ccagttcgat gtaacccact cgtgcaccca    4680
actgatcttc agcatctttt actttcacca gcgtttctgg gtgagcaaaa acaggaaggc    4740
aaaatgccgc aaaaaaggga ataagggcga cacggaaatg ttgaatactc atactcttcc    4800 ttttcaata ttattgaagc atttatcagg gttattgtct catgagcgga tacatatttg      4860
aatgtattta gaaaaataaa caaataggg ttccgcgcac atttccccga aaagtgccac     4920
ctgacgtcta agaaaccatt attatcatga cattaaccta taaaaatagg cgtatcacga    4980
ggccctttcg tcttcaagaa ttccacggac tatagactat actagtatac tccgtctact    5040
gtacgataca cttccgctca ggtccttgtc ctttaacgag gccttaccac tcttttgtta    5100
ctctattgat ccagctcagc aaaggcagtg tgatctaaga ttctatcttc gcgatgtagt    5160
aaaactagct agaccgagaa agagactaga atgcaaaag gcacttctac aatggctgcc    5220
atcattatta tccgatgtga cgctgcagaa gcagaaatac acgcggtcag tgaagctatt    5280
ccgctattga ataacctcag tcaccttgtg caagaactta acaagaaacc aattattaaa    5340
ggcttactta ctgatagtag atcaacgatc agtataatta agtctacaaa tgaagagaaa    5400
tttagaaaca gattttttgg cacaaaggca atgagactta gagatgaagt atcaggtaat    5460
aatttatacg tatactacat cgagaccaag aagaacattg ctgatgtgat gacaaaacct    5520
cttccgataa aaacatttaa actattaact aacaaatgga ttcattagat ctattacatt    5580
atgggtggta tgttggaata aaaatcaact atcatctact aactagtatt tacgttacta    5640
gtatattatc atatacggtg ttagaagatg acgcaaatga tgagaaatag tcatctaaat    5700
tagtggaagc tgaaacgcaa ggattgataa tgtaatagga tcaatgaata ttaacatata    5760
aaatgatgat aataatattt atagaattgt gtagaattgc agattcccctt ttatggattc    5820 ctaaatcctc gaggagaact tctagtatat ctacatacct aatattattg ccttattaaa    5880
aatggaatcc caacaattac atcaaaatcc acattctctt caaaatcaat gtcctgtac    5940 ttccttgttc atgtgtgttc aaaaacgtta tattatagg ataattatac tctatttctc      6000
aacaagtaat tggttgtttg gccgagcggt ctaaggcgcc tgattcaaga aatatcttga    6060
```

```
ccgcagttaa ctgtgggaat actcaggtat cgtaagatgc aagagttcga atctcttagc    6120
aaccattatt ttttcctca acataacgag aacacacagg ggcgctatcg cacagaatca    6180
aattcgatga ctggaaattt tttgttaatt tcagaggtcg cctgacgcat atacctttt    6240 caactgaaaa attgggagaa aaaggaaagg tgagagccgc ggaaccggct tttcatatag   6300
aatagagaag cgttcatgac taaatgcttg catcacaata cttgaagttg acaatattat   6360
ttaaggacct attgtttttt ccaataggtg gttagcaatc gtcttacttt ctaactttc    6420 ttaccttta catttcagca atatatatat atatatttca aggatatacc attctaatgt    6480
ctgcccctaa gaagatcgtc gttttgccag gtgaccacgt tggtcaagaa atcacagccg   6540
aagccattaa ggttcttaaa gctatttctg atgttcgttc caatgtcaag ttcgatttcg   6600
aaaatcattt aattggtggt gctgctatcg atgctacagg tgtcccactt ccagatgagg   6660
cgctggaagc ctccaagaag gttgatgccg ttttgttagg tgctgtgggt ggtcctaaat   6720
ggggtaccgg tagtgttaga cctgaacaag gtttactaaa aatccgtaaa gaacttcaat   6780
tgtacgccaa cttaagacca tgtaactttg catccgactc tcttttagac ttatctccaa   6840
tcaagccaca atttgctaaa ggtactgact tcgttgttgt cagagaatta gtgggaggta   6900
tttactttgg taagagaaag gaagacgatg gtgatggtgt cgcttgggat agtgaacaat   6960
acaccgttcc agaagtgcaa agaatcacaa gaatggccgc tttcatggcc ctacaacatg   7020
agccaccatt gcctatttgg tccttggata aagctaatgt tttggcctct tcaagattat   7080
ggagaaaaac tgtggaggaa accatcaaga acgaattccc tacattgaag gttcaacatc   7140
aattgattga ttctgccgcc atgatcctag ttaagaaccc aacccaccta aatggtatta   7200
taatcaccag caacatgttt ggtgatatca tctccgatga agcctccgtt atcccaggtt   7260
ccttgggttt gttgccatct gcgtccttgg cctctttgcc agacaagaac accgcatttg   7320
gtttgtacga accatgccac ggttctgctc cagatttgcc aaagaataag gtcaaccta   7380 tcgccactat cttgtctgct gcaatgatgt tgaaattgtc attgaacttg cctgaagaag   7440
gtaaggccat tgaagatgca gttaaaaagg ttttggatgc aggtatcaga actggtgatt   7500
taggtggttc caacagtacc acggaagtcg gtgatgctgt cgccgaagaa gttaagaaaa   7560
tccttgctta aaaagattct cttttttat gatatttgta cataaacttt ataaatgaaa    7620
ttcataatag aaacgacacg aaattacaaa atggaatatg ttcatagggt agacgaaact   7680
atatacgcaa tctacataca tttatcaaga aggagaaaaa ggaggatgta aaggaataca   7740
ggtaagcaaa ttgatactaa tggctcaacg tgataaggaa aaagaattgc actttaacat   7800
taatattgac aaggaggagg gcaccacaca aaaagttagg tgtaacagaa atcatgaaa    7860 ctatgattcc taatttatat attggaggat tttctctaaa aaaaaaaaa tacaacaaat    7920 aaaaaacact caatgacctg accatttgat ggagtttaag tcaataccttt cttgaaccat   7980 ttcccataat ggtgaaagtt ccctcaagaa ttttactctg tcagaaacgg ccttaacgac   8040
gtagtcgacc tcctcttcag tactaaatct accaatacca aatctgatgg aagaatgggc   8100
taatgcatca tccttaccca gcgcatgtaa aacataagaa ggttctaggg aagcagatgt   8160
acaggctgaa cccgaggata atgcgatatc ccttagtgcc atcaataaag attctccttc   8220
cacgtaggcg aaagaaacgt taacacaccc tggataacga tgatctggag atccgttcaa   8280
cgtggtatgt tcagcggata atagaccttt gactaattta tcggatagtc ttttgatgtg   8340
agcttggtcg ttgtcaaatt ctttcttcat caatctcgca gcttcaccaa atcccgctac   8400
```

-continued

```
caatgggggg gccaaagtac cagatctcaa tcctctctct tggccaccac cggatagtaa     8460
aggttctaat ctaactcttg gtctccttct tacatagatg gcacctattc cctttggacc     8520
gtaaatcttg tgagaagaaa ttgatagtaa atcaatgttc atttcattga catcaatgtg     8580
aatcttacca taggcttgtg cggcgtcagt atgaaagtag atcttattct ttctacaaat     8640
tgcaccaatt tctttaatag gttgaatgac accgatttca ttattgacag ccatcacaga     8700
gacgagacag gtatctggtc taatggcatc ttccaattcc ttcaaatcga taagaccttg     8760
atcgtccaca tttaggaaag tgacttcaaa tccctccttc atcatggccc gtgcggcttc     8820
caagacacac ttgtgttccg ttctagtggt gatgatgtgt ttcttagtct tcttataaaa     8880
tcttgggaca cccttaagaa ccatattatt agattcggtc gctcccgaag tgaatattat     8940
ttccttgggg tcggcattga tcatctttgc tacgtaagct ctagcatttt ccacagcagt     9000
atttgtttcc caaccgtaag agtgagtgtt ggaatgagga ttaccataaa gtcccgtata     9060
aaacttcaac atcgtatcca aaccctaggt tctgttggt gtagtggctt gcatgtcaag      9120
atatatggga cgagtaccaa aacctgtgtt ttcttgataa gcatggctca ttgcagtgct     9180
accagaagct actacagcat ctgggggtggt accggatgca ctcgcacggg cactagcctg    9240
tgcctttgca gcagcctgaa tatcggtatg cgtttccaga gagaagttgt cgtctaactt     9300
cacgcctgct gcagtctcaa tgatattcga atacgctttg aggagataca gcctaatatc     9360
cgacaaactg ttttacagat ttacgatcgt acttgttacc catcattgaa ttttgaacat     9420
ccgaacctgg gagttttccc tgaaacagat agtatatttg aacctgtata ataatatata    9480
gtctagcgct ttacggaaga caatgtatgt atttcggttc ctggagaaac tattgcatct    9540
attgcatagg taatcttgca cgtcgcatcc ccggttcatt ttctgcgttt ccatcttgca    9600
cttcaatagc atatctttgt taacgaagca tctgtgcttc attttgtaga caaaaatgc     9660
aacgcgagag cgctaatttt tcaaacaaag aatctgagct gcattttac agaacagaaa     9720
tgcaacgcga aagcgctatt ttaccaacga agaatctgtg cttcatttt gtaaaacaaa     9780
aatgcaacgc gagagcgcta atttttcaaa caaagaatct gagctgcatt tttcagaac    9840
agaaatgcaa cgcgagagcg ctattttacc aacaaagaat ctatacttct tttttgttct    9900
acaaaaatgc atcccgagag cgctattttt ctaacaaagc atcttagatt acttttttc    9960
tcctttgtgc gctctataat gcagtctctt gataactttt tgcactgtag gtccgttaag   10020
gttagaagaa ggctactttg gtgtctattt tctcttccat aaaaaaagcc tgactccact   10080
tcccgcgttt actgattact agcgaagctg cgggtgcatt ttttcaagat aaaggcatcc   10140
ccgattatat tctataccga tgtggattgc gcatactttg tgaacagaaa gtgatagcgt   10200
tgatgattct tcattggtca gaaaattatg aacggtttct tctattttgt ctctatatac   10260
tacgtatagg aaatgtttac attttcgtat tgttttcgat tcactctatg aatagttctt   10320
actacaattt ttttgtctaa agagtaatac tagagataaa cataaaaaat gtagaggtcg   10380
agtttagatg caagttcaag gagcgaaagg tggatgggta ggttatatag ggatatagca   10440
cagagatata tagcaaagag atacttttga gcaatgtttg tggaagcggt attcgcaata   10500
ttttagtagc tcgttacagt ccggtgcgtt tttggttttt tgaaagtgcg tcttcagagc   10560
gcttttggtt ttcaaaagcg ctctgaagtt cctatacttt ctagagaata ggaacttcgg   10620
aataggaact tcaaagcgtt tccgaaaacg agcgcttccg aaaatgcaac gcgagctgcg   10680
cacatacagc tcactgttca cgtcgcacct atatctgcgt gttgcctgta tatatatata   10740
catgagaaga acggcatagt gcgtgtttat gcttaaatgc gtacttatat gcgtctattt   10800
```

-continued

```
atgtaggatg aaaggtagtc tagtacctcc tgtgatatta tcccattcca tgcgggtat    10860 cgtatgcttc cttcagcact accctttagc tgttctatat gctgccactc ctcaattgga   10920
ttagtctcat ccttcaatgc tatcatttcc tttgatattc gatcctaggc atagtaccga   10980
gaaactagtg cgaagtagtg atcaggtatt gctgttatct gatgagtata cgttgtcctg   11040
gccacggcag aagcacgctt atcgctccaa tttcccacaa cattagtcaa ctccgttagg   11100
cccttcattg aaagaaatga ggtcatcaaa tgtcttccaa tgtgagattt gggccatt    11160 tttatagcaa agattgaata aggcgcattt ttcttcaa                           11198
```

<210> SEQ ID NO 24
<211> LENGTH: 11427
<212> TYPE: DNA
<213> ORGANISM: Saccharomyces cerevisiae

<400> SEQUENCE: 24

```
agcttcgcgg ccgcctttcg attagcacgc acacacatca catagactgc gtcataaaaa     60
tacactacgg aaaaaccata aagagcaaag cgatacctac ttggaaggaa aaggagcacg    120
cttgtaaggg ggatgggggc taagaagtca ttcactttct tttcccttcg cggtccggac    180
ccgggacccc tcctctcccc gcacgatttc ttcctttcat atcttccttt tattcctatc    240
ccgttgaagc aaccgcacta tgactaaatg gtgctggaca tctccatggc tgtgacttgt    300
gtgtatctca cagtggtaac ggcaccgtgc tcggaaacg gttccttcgt gacaattcta     360
gaacaggggc tacagtctcg ataatagaat aataagcgca ttttgctag cgccgccgcg    420 gcgcccgttt cccaataggg aggcgcagtt tatcggcgga gctctacttc ttcctatttg    480
ggtaagcccc tttctgtttt cggccagtgg ttgctgcagg ctgcgccgga gaacatagtg    540
ataagggatg taactttcga tgagagaatt agcaagcgga aaaaactat ggctagctgg    600 gagttgtttt tcaatcatat aaagggaga aattgttgct cactatgtga cagtttctgg    660
gacgtcttaa cttttattgc agaggactat caaatcatac agatattgtc aaaaaaaaaa    720
aagactaata ataacatatg cggtccggat ccagtttaaa cagtagcttt ggacttcttc    780
gccagaggtt tggtcaagtc tccaatcaag gttgtcggct tgtctacctt gccagaaatt    840
tacgaaaaga tggaaaaggg tcaaatcgtt ggtagatacg ttgttgacac ttctaaataa    900
gcgaatttct tatgatttat gatttttatt attaaataag ttataaaaaa aataagtgta    960
tacaaatttt aaagtgactc ttaggttttta aaacgaaaat tcttgttctt gagtaactct    1020
ttcctgtagg tcaggttgct ttctcaggta tagcatgagg tcgctcttat tgaccacacc   1080
tctaccggca tgccgagcaa atgcctgcaa atcgctcccc atttcaccca attgtagata   1140
tgctaactcc agcaatgagt tgatgaatct cggtgtgtat tttatgtcct cagaagacaa   1200
cacctgttgt aatcgttctt ccacacggat gcggccgct tgatcctcta cgccggacgc   1260
atcgtggccg gcatcaccgg cgccacaggt gcggttgctg gcgcctatat cgccgacatc   1320
accgatgggg aagatcgggc tcgccacttc gggctcatga gcgcttgttt cggcgtgggt   1380
atggtggcag gccccgtggc cggggactg ttgggcgcca tctccttgca tgcaccattc   1440
cttgcggcgg cggtgctcaa cggcctcaac ctactactgg gctgcttcct aatgcaggag   1500
tcgcataagg gagagcgtcg accgatgccc ttgagagcct tcaacccagt cagctccttc   1560
cggtgggcgc ggggcatgac tatcgtcgcc gcacttatga ctgtcttctt tatcatgcaa   1620
ctcgtaggac aggtgccggc agcgctctgg gtcattttcg gcgaggaccg ctttcgctgg   1680
```

```
agcgcgacga tgatcggcct gtcgcttgcg gtattcggaa tcttgcacgc cctcgctcaa    1740
gccttcgtca ctggtcccgc caccaaacgt ttcggcgaga agcaggccat tatcgccggc    1800
atggcggccg acgcgctggg ctacgtcttg ctggcgttcg cgacgcgagg ctggatggcc    1860
ttccccatta tgattcttct cgcttccggc ggcatcggga tgcccgcgtt gcaggccatg    1920
ctgtccaggc aggtagatga cgaccatcag ggacagcttc aaggatcgct cgcggctctt    1980
accagcctaa cttcgatcac tggaccgctg atcgtcacgg cgatttatgc cgcctcggcg    2040
agcacatgga acgggttggc atggattgta ggcgccgccc tataccttgt ctgcctcccc    2100
gcgttgcgtc gcggtgcatg gagccgggcc acctcgacct gaatgaaagc cggcggcacc    2160
tcgctaacgg attcaccact ccaagaattg gagccaatca attcttgcgg agaactgtga    2220
atgcgcaaac caaccttgg cagaacatat ccatcgcgtc cgccatctcc agcagccgca    2280
cgcggcgcat ctcgggcagc gttgggtcct ggccacgggt gcgcatgatc gtgctcctgt    2340
cgttgaggac ccggctaggc tggcggggtt gccttactgg ttagcagaat gaatcaccga    2400
tacgcgagcg aacgtgaagc gactgctgct gcaaaacgtc tgcgacctga gcaacaacat    2460
gaatggtctt cggtttccgt gtttcgtaaa gtctggaaac gcggaagtca gcgccctgca    2520
ccattatgtt ccggatctgc atcgcaggat gctgctggct accctgtgga acacctacat    2580
ctgtattaac gaagcgctgg cattgaccct gagtgatttt tctctggtcc cgccgcatcc    2640
ataccgccag ttgtttaccc tcacaacgtt ccagtaaccg ggcatgttca tcatcagtaa    2700
cccgtatcgt gagcatcctc tctcgtttca tcggtatcat taccccccatg aacagaaatt    2760
cccccttaca cggaggcatc aagtgaccaa acaggaaaaa accgcccta acatggcccg    2820
ctttatcaga agccagacat taacgcttct ggagaaactc aacgagctgg acgcggatga    2880
acaggcagac atctgtgaat cgcttcacga ccacgctgat gagctttacc gcagctgcct    2940
cgcgcgtttc ggtgatgacg gtgaaaacct ctgacacatg cagctcccgg agacggtcac    3000
agcttgtctg taagcggatg ccgggagcag acaagcccgt cagggcgcgt cagcgggtgt    3060
tggcgggtgt cggggcgcag ccatgaccca gtcacgtagc gatagcggag tgtatactgg    3120
cttaactatg cggcatcaga gcagattgta ctgagagtgc acgatatccg gtgtgaaata    3180
ccgcacagat gcgtaaggag aaaataccgc atcaggcgct cttccgcttc ctcgctcact    3240
gactcgctgc gctcggtcgt tcggctgcgg cgagcggtat cagctcactc aaaggcggta    3300
atacggttat ccacagaatc aggggataac gcaggaaaga acatgtgagc aaaaggccag    3360
caaaaggcca ggaaccgtaa aaaggccgcg ttgctggcgt ttttccatag gctccgcccc    3420
cctgacgagc atcacaaaaa tcgacgctca agtcagaggt ggcgaaaccc gacaggacta    3480
taaagatacc aggcgtttcc ccctggaagc tccctcgtgc gctctcctgt tccgaccctg    3540
ccgcttaccg gatacctgtc cgcctttctc ccttcgggaa gcgtggcgct ttctcaatgc    3600
tcacgctgta ggtatctcag ttcggtgtag gtcgttcgct ccaagctggg ctgtgtgcac    3660
gaaccccccg ttcagcccga ccgctgcgcc ttatccggta actatcgtct tgagtccaac    3720
ccggtaagac acgacttatc gccactggca gcagccactg gtaacaggat tagcagagcg    3780
aggtatgtag gcggtgctac agagttcttg aagtggtggc ctaactacgg ctacactaga    3840
aggacagtat ttggtatctg cgctctgctg aagccagtta ccttcggaaa aagagttggt    3900
agctcttgat ccggcaaaca aaccaccgct ggtagcggtg gttttttgt ttgcaagcag    3960
cagattacgc gcagaaaaaa aggatctcaa gaagatcctt tgatctttc tacgggtct    4020
gacgctcagt ggaacgaaaa ctcacgttaa gggattttgg tcatgagatt atcaaaaagg    4080
```

```
atcttcacct agatccttt aaattaaaaa tgaagttta aatcaatcta aagtatatat    4140
gagtaaactt ggtctgacag ttaccaatgc ttaatcagtg aggcacctat ctcagcgatc    4200
tgtctatttc gttcatccat agttgcctga ctccccgtcg tgtagataac tacgatacgg    4260
gagggcttac catctggccc cagtgctgca atgataccgc gagacccacg ctcaccggct    4320
ccagatttat cagcaataaa ccagccagcc ggaagggccg agcgcagaag tggtcctgca    4380
actttatccg cctccatcca gtctattaat tgttgccggg aagctagagt aagtagttcg    4440
ccagttaata gtttgcgcaa cgttgttgcc attgctgcag gcatcgtggt gtcacgctcg    4500
tcgtttggta tggcttcatt cagctccggt tcccaacgat caaggcgagt tacatgatcc    4560
cccatgttgt gcaaaaaagc ggttagctcc ttcggtcctc cgatcgttgt cagaagtaag    4620
ttggccgcag tgttatcact catggttatg gcagcactgc ataattctct tactgtcatg    4680
ccatccgtaa gatgcttttc tgtgactggt gagtactcaa ccaagtcatt ctgagaatag    4740
tgtatgcggc gaccgagttg ctcttgcccg gcgtcaacac gggataatac cgcgccacat    4800
agcagaactt taaaagtgct catcattgga aaacgttctt cggggcgaaa actctcaagg    4860
atcttaccgc tgttgagatc cagttcgatg taacccactc gtgcacccaa ctgatcttca    4920
gcatctttta ctttcaccag cgtttctggg tgagcaaaaa caggaaggca aaatgccgca    4980
aaaagggaa taagggcgac acggaaatgt tgaatactca tactcttcct ttttcaatat    5040
tattgaagca tttatcaggg ttattgtctc atgagcggat acatatttga atgtatttag    5100
aaaaataaac aaatagggt tccgcgcaca tttccccgaa aagtgccacc tgacgtctaa    5160
gaaaccatta ttatcatgac attaacctat aaaaataggc gtatcacgag gccctttcgt    5220
cttcaagaat tccacggact atagactata ctagtatact ccgtctactg tacgatacac    5280
ttccgctcag gtccttgtcc tttaacgagg ccttaccact cttttgttac tctattgatc    5340
cagctcagca aaggcagtgt gatctaagat tctatcttcg cgatgtagta aaactagcta    5400
gaccgagaaa gagactagaa atgcaaaagg cacttctaca atggctgcca tcattattat    5460
ccgatgtgac gctgcagaag cagaaataca cgcggtcagt gaagctattc cgctattgaa    5520
taacctcagt caccttgtgc aagaacttaa caagaaacca attattaaag gcttacttac    5580
tgatagtaga tcaacgatca gtataattaa gtctacaaat gaagagaaat ttagaaacag    5640
attttttggc acaaaggcaa tgagacttag agatgaagta tcaggtaata atttatacgt    5700
atactacatc gagaccaaga agaacattgc tgatgtgatg acaaaacctc ttccgataaa    5760
aacatttaaa ctattaacta acaaatggat tcattagatc tattacatta tgggtggtat    5820
gttggaataa aaatcaacta tcatctacta actagtattt acgttactag tatattatca    5880
tatacggtgt tagaagatga cgcaaatgat gagaaatagt catctaaatt agtggaagct    5940
gaaacgcaag gattgataat gtaataggat caatgaatat taacatataa aatgatgata    6000
ataatattta tagaattgtg tagaattgca gattcccttt tatggattcc taaatcctcg    6060
aggagaactt ctagtatatc tacataccta atattattgc cttattaaaa atggaatccc    6120
aacaattaca tcaaaatcca cattctcttc aaaatcaatt gtcctgtact ccttgttca    6180
tgtgtgttca aaaacgttat atttatagga taattatact ctatttctca acaagtaatt    6240
ggttgtttgg ccgagcggtc taaggcgcct gattcaagaa atatcttgac cgcagttaac    6300
tgtgggaata ctcaggtatc gtaagatgca agagttcgaa tctcttagca accattattt    6360
ttttcctcaa cataacgaga acacacaggg gcgctatcgc acagaatcaa attcgatgac    6420
```

```
tggaaatttt ttgttaattt cagaggtcgc ctgacgcata tacctttttc aactgaaaaa    6480
ttgggagaaa aaggaaaggt gagagccgcg gaaccggctt ttcatataga atagagaagc    6540
gttcatgact aaatgcttgc atcacaatac ttgaagttga caatattatt taaggaccta    6600
ttgttttttc caataggtgg ttagcaatcg tcttactttc taacttttct taccttttac    6660
atttcagcaa tatatatata tatatttcaa ggatatacca ttctaatgtc tgcccctaag    6720
aagatcgtcg ttttgccagg tgaccacgtt ggtcaagaaa tcacagccga agccattaag    6780
gttcttaaag ctatttctga tgttcgttcc aatgtcaagt tcgatttcga aaatcattta    6840
attggtggtg ctgctatcga tgctacaggt gtcccacttc cagatgaggc gctggaagcc    6900
tccaagaagg ttgatgccgt tttgttaggt gctgtgggtg gtcctaaatg gggtaccggt    6960
agtgttagac ctgaacaagg tttactaaaa atccgtaaag aacttcaatt gtacgccaac    7020
ttaagaccat gtaactttgc atccgactct ctttttagact tatctccaat caagccacaa    7080
tttgctaaag gtactgactt cgttgttgtc agagaattag tgggaggtat ttactttggt    7140
aagagaaagg aagacgatgg tgatggtgtc gcttgggata gtgaacaata caccgttcca    7200
gaagtgcaaa gaatcacaag aatggccgct ttcatggccc tacaacatga gccaccattg    7260
cctatttggt ccttggataa agctaatgtt ttggcctctt caagattatg gagaaaaact    7320
gtggaggaaa ccatcaagaa cgaattccct acattgaagg ttcaacatca attgattgat    7380
tctgccgcca tgatcctagt taagaaccca acccacctaa atggtattat aatcaccagc    7440
aacatgtttg gtgatatcat ctccgatgaa gcctccgtta tcccaggttc cttgggtttg    7500
ttgccatctg cgtccttggc ctcttttgcca gacaagaaca ccgcatttgg tttgtacgaa    7560
ccatgccacg ttctgctcc agatttgcca aagaataagg tcaaccctat cgccactatc    7620
ttgtctgctg caatgatgtt gaaattgtca ttgaacttgc ctgaagaagg taaggccatt    7680
gaagatgcag ttaaaaaggt tttggatgca ggtatcagaa ctggtgattt aggtggttcc    7740
aacagtacca cggaagtcgg tgatgctgtc gccgaagaag ttaagaaaat ccttgcttaa    7800
aaagattctc ttttttttatg atatttgtac ataaacttta taaatgaaat tcataataga    7860
aacgacacga aattacaaaa tggaatatgt tcatagggta gacgaaacta tatacgcaat    7920
ctacatacat ttatcaagaa ggagaaaaag gaggatgtaa aggaatacag gtaagcaaat    7980
tgatactaat ggctcaacgt gataaggaaa aagaattgca ctttaacatt aatattgaca    8040
aggaggaggg caccacacaa aaagttaggt gtaacagaaa atcatgaaac tatgattcct    8100
aatttatata ttggaggatt ttctctaaaa aaaaaaaaat acaacaaata aaaacactc    8160 aatgacctga ccatttgatg gagtttaagt caataccttc ttgaaccatt tcccataatg    8220
gtgaaagttc cctcaagaat tttactctgt cagaaacggc cttaacgacg tagtcgacct    8280
cctcttcagt actaaatcta ccaataccaa atctgatgga agaatgggct aatgcatcat    8340
ccttacccag cgcatgtaaa acataagaag gttctaggga agcagatgta caggctgaac    8400
ccgaggataa tgcgatatcc cttagtgcca tcaataaaga ttctccttcc acgtaggcga    8460
aagaaacgtt aacacaccct ggataacgat gatctgcgaga tccgttcaac gtggtatgtt    8520
cagcggataa tagacctttg actaatttat cggatagtct tttgatgtga gcttggtcgt    8580
tgtcaaattc tttcttcatc aatctcgcag cttcaccaaa tcccgctacc aatggggggg    8640
ccaaagtacc agatctcaat cctctctctt ggccaccacc ggatagtaaa ggttctaatc    8700
taactcttgg tctccttctt acatagatgg cacctattcc ctttggaccg taaatcttgt    8760
gagaagaaat tgatagtaaa tcaatgttca tttcattgac atcaatgtga atcttaccat    8820
```

```
aggcttgtgc ggcgtcagta tgaaagtaga tcttattctt tctacaaatt gcaccaattt   8880
ctttaatagg ttgaatgaca ccgatttcat tattgacagc catcacagag acgagacagg   8940
tatctggtct aatggcatct tccaattcct tcaaatcgat aagaccttga tcgtccacat   9000
ttaggaaagt gacttcaaat ccctccttca tcatggcccg tgcggcttcc aagacacact   9060
tgtgttccgt tctagtggtg atgatgtgtt tcttagtctt cttataaaat cttgggacac   9120
ccttaagaac catattatta gattcggtcg ctcccgaagt gaatattatt tccttggggt   9180
cggcattgat catctttgct acgtaagctc tagcattttc cacagcagta tttgtttccc   9240
aaccgtaaga gtgagtgttg gaatgaggat taccataaag tcccgtataa aacttcaaca   9300
tcgtatccaa aaccctaggg tctgttggtg tagtggcttg catgtcaaga tatatgggac   9360
gagtaccaaa acctgtgttt tcttgataag catggctcat tgcagtgcta ccagaagcta   9420
ctacagcatc tggggtggta ccggatgcac tcgcacgggc actagcctgt gcctttgcag   9480
cagcctgaat atcggtatgc gtttccagag agaagttgtc gtctaacttc acgcctgctg   9540
cagtctcaat gatattcgaa tacgctttga ggagatacag cctaatatcc gacaaactgt   9600
tttacagatt tacgatcgta cttgttaccc atcattgaat tttgaacatc cgaacctggg   9660
agttttccct gaaacagata gtatatttga acctgtataa taatatatag tctagcgctt   9720
tacggaagac aatgtatgta tttcggttcc tggagaaact attgcatcta ttgcataggt   9780
aatcttgcac gtcgcatccc cggttcattt tctgcgtttc catcttgcac ttcaatagca   9840
tatctttgtt aacgaagcat ctgtgcttca ttttgtagaa caaaaatgca acgcgagagc   9900
gctaattttt caaacaaaga atctgagctg cattttttaca gaacagaaat gcaacgcgaa   9960
agcgctattt taccaacgaa gaatctgtgc ttcattttg taaaacaaaa atgcaacgcg   10020
agagcgctaa tttttcaaac aaagaatctg agctgcattt ttacagaaca gaaatgcaac   10080
gcgagagcgc tattttacca acaaagaatc tatacttctt ttttgttcta caaaaatgca   10140
tcccgagagc gctatttttc taacaaagca tcttagatta cttttttttct cctttgtgcg   10200 ctctataatg cagtctcttg ataactttt gcactgtagg tccgttaagg ttagaagaag   10260
gctactttgg tgtctatttt ctcttccata aaaaagcct gactccactt cccgcgttta   10320
ctgattacta gcgaagctgc gggtgcattt tttcaagata aaggcatccc cgattatatt   10380
ctataccgat gtggattgcg catactttgt gaacagaaag tgatagcgtt gatgattctt   10440
cattggtcag aaaattatga acggtttctt ctatttttgtc tctatatact acgtatagga   10500
aatgtttaca ttttcgtatt gttttcgatt cactctatga atagttctta ctacaatttt   10560
tttgtctaaa gagtaatact agagataaac ataaaaaatg tagaggtcga gtttagatgc   10620
aagttcaagg agcgaaaggt ggatgggtag gttatatagg gatatagcac agagatatat   10680
agcaaagaga tacttttgag caatgtttgt ggaagcggta ttcgcaatat tttagtagct   10740
cgttacagtc cggtgcgttt ttggtttttt gaaagtgcgt cttcagagcg cttttggttt   10800
tcaaaagcgc tctgaagttc ctatactttc tagagaatag gaacttcgga ataggaactt   10860
caaagcgttt ccgaaaacga gcgcttccga aaatgcaacg cgagctgcgc acatacagct   10920
cactgttcac gtcgcaccta tatctgcgtg ttgcctgtat atatatatac atgagaagaa   10980
cggcatagtg cgtgtttatg cttaaatgcg tacttatatg cgtctatta tgtaggatga   11040 aaggtagtct agtacctcct gtgatattat cccattccat gcgggtatc gtatgcttcc   11100 ttcagcacta ccctttagct gttctatatg ctgccactcc tcaattggat tagtctcatc   11160
```

```
cttcaatgct atcatttcct ttgatattcg atcctaggca tagtaccgag aaactagtgc    11220
gaagtagtga tcaggtattg ctgttatctg atgagtatac gttgtcctgg ccacggcaga    11280
agcacgctta tcgctccaat ttcccacaac attagtcaac tccgttaggc ccttcattga    11340
aagaaatgag gtcatcaaat gtcttccaat gtgagatttt gggccatttt ttatagcaaa    11400
gattgaataa ggcgcatttt tcttcaa                                        11427

<210> SEQ ID NO 25
<211> LENGTH: 11201
<212> TYPE: DNA
<213> ORGANISM: Saccharomyces cerevisiae

<400> SEQUENCE: 25
aagcttcgcg gccgcgcaga aatgatgaag ggtgttagcg ccgtccactg atgtgcctgg      60
tagtcatgat ttacgtataa ctaacacatc atgaggacgg cggcgtcacc ccaacgcaaa     120
agagtgactt ccctgcgctt tgccaaaacc ccatacatcg ccatctggct cctggcaggg     180
cggttgatgg acatcagccg cctcccttaa ttgctaaagc ctccacaagg cacaattaag     240
caatatttcg ggaaagtaca ccagtcagtt tgcgctttta tgactgggtt ctaaggtact     300
agatgtgaag tagtggtgac agaatcaggg agataagagg gagcagggtg gggtaatgat     360
gtgcgataac aatcttgctt ggctaatcac ccccatatct tgtagtgagt atataaatag     420
gagcctccct tcctattgca actccataaa atttttttt gtagccactt ctgtaacaag     480
ataaataaaa ccaactaatc gagatatcac atatgcggtc cggatccagt ttaaacagta     540
gctttggact tcttcgccag aggtttggtc aagtctccaa tcaaggttgt cggcttgtct     600
accttgccag aaatttacga aaagatggaa aagggtcaaa tcgttggtag atacgttgtt     660
gacacttcta ataagcgaa tttcttatga tttatgattt ttattattaa ataagttata     720
aaaaaaataa gtgtatacaa attttaaagt gactcttagg ttttaaaacg aaaattcttg     780
ttcttgagta actctttcct gtaggtcagg ttgctttctc aggtatagca tgaggtcgct     840
cttattgacc acacctctac cggcatgccg agcaaatgcc tgcaaatcgc tccccatttc     900
acccaattgt agatatgcta actccagcaa tgagttgatg aatctcggtg tgtatttat     960 gtcctcagaa acaacacct gttgtaatcg ttcttccaca cggatcgcgg ccgcttgatc    1020
ctctacgccg gacgcatcgt ggccggcatc accggcgcca caggtgcggt tgctggcgcc    1080
tatatcgccg acatcaccga tggggaagat cgggctcgcc acttcgggct catgagcgct    1140
tgtttcggcg tgggtatggt ggcaggcccc gtggccgggg gactgttggg cgccatctcc    1200
ttgcatgcac cattccttgc ggcggcggtg ctcaacggcc tcaacctact actgggctgc    1260
ttcctaatgc aggagtcgca taaggagag cgtcgaccga tgcccttgag agccttcaac    1320
ccagtcagct ccttccggtg ggcgcggggc atgactatcg tcgccgcact tatgactgtc    1380
ttctttatca tgcaactcgt aggacaggtg ccggcagcgc tctgggtcat tttcggcgag    1440
gaccgctttc gctggagcgc gacgatgatc ggcctgtcgc ttgcggtatt cggaatcttg    1500
cacgccctcg ctcaagcctt cgtcactggt cccgccacca acgtttcgg cgagaagcag    1560 gccattatcg ccggcatggc ggccgacgcg ctgggctacg tcttgctggc gttcgcgacg    1620
cgaggctgga tggccttccc cattatgatt cttctcgctt ccggcggcat cgggatgccc    1680
gcgttgcagg ccatgctgtc caggcaggta gatgacgacc atcagggaca gcttcaagga    1740
tcgctcgcgg ctcttaccag cctaacttcg atcactggac cgctgatcgt cacggcgatt    1800
tatgccgcct cggcgagcac atggaacggg ttggcatgga ttgtaggcgc cgccctatac    1860
```

-continued

```
cttgtctgcc tccccgcgtt gcgtcgcggt gcatggagcc gggccacctc gacctgaatg   1920
gaagccggcg gcacctcgct aacggattca ccactccaag aattggagcc aatcaattct   1980
tgcggagaac tgtgaatgcg caaaccaacc cttggcagaa catatccatc gcgtccgcca   2040
tctccagcag ccgcacgcgg cgcatctcgg gcagcgttgg gtcctggcca cgggtgcgca   2100
tgatcgtgct cctgtcgttg aggacccggc taggctggcg gggttgcctt actggttagc   2160
agaatgaatc accgatacgc gagcgaacgt gaagcgactg ctgctgcaaa cgtctgcga    2220
cctgagcaac aacatgaatg gtcttcggtt ccgtgtttc gtaaagtctg gaaacgcgga    2280
agtcagcgcc ctgcaccatt atgttccgga tctgcatcgc aggatgctgc tggctaccct   2340
gtggaacacc tacatctgta ttaacgaagc gctggcattg accctgagtg attttttctct  2400
ggtcccgccg catccatacc gccagttgtt taccctcaca acgttccagt aaccgggcat   2460
gttcatcatc agtaacccgt atcgtgagca tcctctctcg tttcatcggt atcattaccc    2520
ccatgaacag aaattcccccc ttacacggag gcatcaagtg accaaacagg aaaaaaccgc   2580
ccttaacatg gcccgcttta tcagaagcca gacattaacg cttctggaga aactcaacga    2640
gctggacgcg gatgaacagg cagacatctg tgaatcgctt cacgaccacg ctgatgagct   2700
ttaccgcagc tgcctcgcgc gtttcggtga tgacggtgaa aacctctgac acatgcagct   2760
cccggagacg gtcacagctt gtctgtaagc ggatgccggg agcagacaag cccgtcaggg   2820
cgcgtcagcg ggtgttggcg ggtgtcgggg cgcagccatg acccagtcac gtagcgatag   2880
cggagtgtat actggcttaa ctatgcgca tcagagcaga ttgtactgag agtgcacgat     2940
atccggtgtg aaataccgca cagatgcgta aggagaaaat accgcatcag gcgctcttcc    3000
gcttcctcgc tcactgactc gctgcgctcg gtcgttcggc tgcggcgagc ggtatcagct    3060
cactcaaagg cggtaatacg gttatccaca gaatcagggg ataacgcagg aaagaacatg    3120
tgagcaaaag gccagcaaaa ggccaggaac cgtaaaaagg ccgcgttgct ggcgtttttc    3180
cataggctcc gcccccctga cgagcatcac aaaaatcgac gctcaagtca gaggtggcga   3240
aacccgacag gactataaag ataccaggcg tttccccctg gaagctccct cgtgcgctct   3300
cctgttccga ccctgccgct taccggatac ctgtccgcct ttctcccttc gggaagcgtg   3360
gcgctttctc aatgctcacg ctgtaggtat ctcagttcgg tgtaggtcgt tcgctccaag   3420
ctgggctgtg tgcacgaacc ccccgttcag cccgaccgct gcgccttatc cggtaactat   3480
cgtcttgagt ccaacccggt aagacacgac ttatcgccac tggcagcagc cactggtaac   3540
aggattagca gagcgaggta tgtaggcggt gctacagagt tcttgaagtg gtggcctaac   3600
tacggctaca ctagaaggac agtatttggt atctgcgctc tgctgaagcc agttaccttc   3660
ggaaaaagag ttggtagctc ttgatccggc aaacaaacca ccgctggtag cggtggtttt   3720
tttgtttgca agcagcagat tacgcgcaga aaaaaaggat ctcaagaaga tcctttgatc   3780
ttttctacgg ggtctgacgc tcagtggaac gaaaactcac gttaagggat tttggtcatg   3840
agattatcaa aaaggatctt cacctagatc ctttttaaatt aaaaatgaag ttttaaatca   3900
atctaaagta tatatgagta aacttggtct gacagttacc aatgcttaat cagtgaggca   3960
cctatctcag cgatctgtct atttcgttca tccatagttg cctgactccc cgtcgtgtag   4020
ataactacga tacgggaggg cttaccatct ggccccagtg ctgcaatgat accgcgagac   4080
ccacgctcac cggctccaga tttatcagca ataaaccagc cagccggaag ggccgagcgc   4140
agaagtggtc ctgcaacttt atccgcctcc atccagtcta ttaattgttg ccgggaagct   4200
```

```
agagtaagta gttcgccagt taatagtttg cgcaacgttg ttgccattgc tgcaggcatc    4260
gtggtgtcac gctcgtcgtt tggtatggct tcattcagct ccggttccca acgatcaagg    4320
cgagttacat gatcccccat gttgtgcaaa aaagcggtta gctccttcgg tcctccgatc    4380
gttgtcagaa gtaagttggc cgcagtgtta tcactcatgg ttatggcagc actgcataat    4440
tctcttactg tcatgccatc cgtaagatgc ttttctgtga ctggtgagta ctcaaccaag    4500
tcattctgag aatagtgtat gcggcgaccg agttgctctt gcccggcgtc aacacgggat    4560
aataccgcgc cacatagcag aactttaaaa gtgctcatca ttggaaaacg ttcttcgggg    4620
cgaaaactct caaggatctt accgctgttg agatccagtt cgatgtaacc cactcgtgca    4680
cccaactgat cttcagcatc ttttactttc accagcgttt ctgggtgagc aaaaacagga    4740
aggcaaaatg ccgcaaaaaa gggaataagg gcgacacgga aatgttgaat actcatactc    4800
ttccttttc aatattattg aagcatttat cagggttatt gtctcatgag cggatacata    4860
tttgaatgta tttagaaaaa taaacaaata ggggttccgc gcacatttcc ccgaaaagtg    4920
ccacctgacg tctaagaaac cattattatc atgacattaa cctataaaaa taggcgtatc    4980
acgaggccct ttcgtcttca agaattccac ggactataga ctatactagt atactccgtc    5040
tactgtacga tacacttccg ctcaggtcct tgtccttaa cgaggcctta ccactctttt    5100
gttactctat tgatccagct cagcaaaggc agtgtgatct aagattctat cttcgcgatg    5160
tagtaaaact agctagaccg agaaagagac tagaaatgca aaaggcactt ctacaatggc    5220
tgccatcatt attatccgat gtgacgctgc agaagcagaa atacgcgcgg tcagtgaagc    5280
tattccgcta ttgaataacc tcagtcacct tgtgcaagaa cttaacaaga aaccaattat    5340
taaaggctta cttactgata gtagatcaac gatcagtata attaagtcta caaatgaaga    5400
gaaatttaga aacagatttt ttggcacaaa ggcaatgaga cttagagatg aagtatcagg    5460
taataatttta tacgtatact acatcgagac caagaagaac attgctgatg tgatgacaaa    5520
acctcttccg ataaaaacat ttaaactatt aactaacaaa tggattcatt agatctatta    5580
cattatgggt ggtatgttgg aataaaaatc aactatcatc tactaactag tatttacgtt    5640
actagtatat tatcatatac ggtgttagaa gatgacgcaa atgatgagaa atagtcatct    5700
aaattagtgg aagctgaaac gcaaggattg ataatgtaat aggatcaatg aatattaaca    5760
tataaaatga tgataataat attatagaa ttgtgtagaa ttgcagattc ccttttatgg    5820
attcctaaat cctcgaggag aacttctagt atatctacat acctaatatt attgccttat    5880
taaaaatgga atcccaacaa ttacatcaaa atccacattc tcttcaaaat caattgtcct    5940
gtacttcctt gttcatgtgt gttcaaaaac gttatattta taggataatt atactctatt    6000
tctcaacaag taattggttg tttggccgag cggtctaagg cgcctgattc aagaaatatc    6060
ttgaccgcag ttaactgtgg gaatactcag gtatcgtaag atgcaagagt tcgaatctct    6120
tagcaaccat tatttttc ctcaacataa cgagaacaca caggggcgct atcgcacaga    6180
atcaaattcg atgactggaa attttttgtt aatttcagag gtcgcctgac gcatatacct    6240
ttttcaactg aaaattggg agaaaaagga aggtgagag ccgcggaacc ggcttttcat    6300
atagaataga gaagcgttca tgactaaatg cttgcatcac aatacttgaa gttgacaata    6360
ttatttaagg acctattgtt ttttccaata ggtggttagc aatcgtctta ctttctaact    6420
tttcttacct tttacatttc agcaatatat atatatatat ttcaaggata taccattcta    6480
atgtctgccc ctaagaagat cgtcgttttg ccaggtgacc acgttggtca agaaatcaca    6540
gccgaagcca ttaaggttct taaagctatt tctgatgttc gttccaatgt caagttcgat    6600
```

-continued

```
ttcgaaaatc atttaattgg tggtgctgct atcgatgcta caggtgtccc acttccagat       6660
gaggcgctgg aagcctccaa gaaggttgat gccgttttgt taggtgctgt gggtggtcct       6720
aaatggggta ccgtagtgt tagacctgaa caaggtttac taaaaatccg taaagaactt       6780
caattgtacg ccaacttaag accatgtaac tttgcatccg actctctttt agacttatct       6840
ccaatcaagc cacaatttgc taaaggtact gacttcgttg ttgtcagaga attagtggga       6900
ggtatttact ttggtaagag aaaggaagac gatggtgatg gtgtcgcttg ggatagtgaa       6960
caatacaccg ttccagaagt gcaaagaatc acaagaatgg ccgctttcat ggccctacaa       7020
catgagccac cattgcctat ttggtccttg gataaagcta atgttttggc ctcttcaaga       7080
ttatggagaa aaactgtgga ggaaaccatc aagaacgaat tccctacatt gaaggttcaa       7140
catcaattga ttgattctgc cgccatgatc ctagttaaga acccaaccca cctaaatggt       7200
attataatca ccagcaacat gtttggtgat atcatctccg atgaagcctc cgttatccca       7260
ggttccttgg gtttgttgcc atctgcgtcc ttggcctctt gccagacaa gaacaccgca       7320 tttggttttgt acgaaccatg ccacggttct gctccagatt tgccaaagaa taaggtcaac       7380
cctatcgcca ctatcttgtc tgctgcaatg atgttgaaat tgtcattgaa cttgcctgaa       7440
gaaggtaagg ccattgaaga tgcagttaaa aaggttttgg atgcaggtat cagaactggt       7500
gatttaggtg gttccaacag taccacggaa gtcggtgatg ctgtcgccga agaagttaag       7560
aaaatccttg cttaaaaaga ttctcttttt ttatgatatt tgtacataaa ctttataaat       7620
gaaattcata atagaaacga cacgaaatta caaaatggaa tatgttcata gggtagacga       7680
aactatatac gcaatctaca tacatttatc aagaaggaga aaaaggagga tgtaaaggaa       7740
tacaggtaag caaattgata ctaatggctc aacgtgataa ggaaaaagaa ttgcacttta       7800
acattaatat tgacaaggag gagggcacca cacaaaaagt taggtgtaac agaaaatcat       7860 gaaactgatga ttcctaattt atatattgga ggatttctc taaaaaaaaa aaatacaac       7920 aaataaaaaa cactcaatga cctgaccatt tgatggagtt taagtcaata ccttcttgaa       7980
ccatttccca taatggtgaa agttccctca agaattttac tctgtcagaa acggccttaa       8040
cgacgtagtc gacctcctct tcagtactaa atctaccaat accaaatctg atggaagaat       8100
gggctaatgc atcatcctta cccagcgcat gtaaaacata agaaggttct agggaagcag       8160
atgtacaggc tgaacccgag gataatgcga tatcccttag tgccatcaat aaagattctc       8220
cttccacgta ggcgaaagaa acgttaacac accctggata acgatgatct ggagatccgt       8280
tcaacgtggt atgttcagcg gataatagac ctttgactaa tttatcggat agtcttttga       8340
tgtgagcttg tcgttgtca aattctttct tcatcaatct cgcagcttca ccaaatcccg       8400
ctaccaatgg gggggccaaa gtaccagatc tcaatcctct ctcttggcca ccaccggata       8460
gtaaaggttc taatctaact cttggtctcc ttcttacata gatggcacct attccctttg       8520
gaccgtaaat cttgtgagaa gaaattgata gtaaatcaat gttcatttca ttgacatcaa       8580
tgtgaatctt accataggct tgtgcggcgt cagtatgaaa gtagatctta ttctttctac       8640
aaattgcacc aatttcttta ataggttgaa tgacaccgat tcattattg acagccatca       8700 cagagacgag acaggtatct ggtctaatgg catcttccaa ttccttcaaa tcgataagac       8760
cttgatcgtc cacatttagg aaagtgactt caaatccctc cttcatcatg gcccgtgcgg       8820
cttccaagac acacttgtgt tccgttctag tggtgatgat gtgtttctta gtcttcttat       8880
aaaatcttgg gacacccttta agaaccatat tattagattc ggtcgctccc gaagtgaata       8940
```

```
ttatttcctt ggggtcggca ttgatcatct ttgctacgta agctctagca ttttccacag    9000
cagtatttgt ttcccaaccg taagagtgag tgttggaatg aggattacca taaagtcccg    9060
tataaaactt caacatcgta tccaaaaccc tagggtctgt tggtgtagtg gcttgcatgt    9120
caagatatat gggacgagta ccaaaacctg tgttttcttg ataagcatgg ctcattgcag    9180
tgctaccaga agctactaca gcatctgggg tggtaccgga tgcactcgca cgggcactag    9240
cctgtgcctt tgcagcagcc tgaatatcgg tatgcgtttc cagagagaag ttgtcgtcta    9300
acttcacgcc tgctgcagtc tcaatgatat tcgaatacgc tttgaggaga tacagcctaa    9360
tatccgacaa actgttttac agatttacga tcgtacttgt tacccatcat tgaattttga    9420
acatccgaac ctgggagttt tccctgaaac agatagtata tttgaacctg tataataata    9480
tatagtctag cgctttacgg aagacaatgt atgtatttcg gttcctggag aaactattgc    9540
atctattgca taggtaatct tgcacgtcgc atccccggtt cattttctgc gtttccatct    9600
tgcacttcaa tagcatatct ttgttaacga agcatctgtg cttcattttg tagaacaaaa    9660
atgcaacgcg agagcgctaa ttttcaaac aaagaatctg agctgcattt ttacagaaca    9720
gaaatgcaac gcgaaagcgc tattttacca acgaagaatc tgtgcttcat ttttgtaaaa    9780
caaaatgca acgcgagagc gctaattttt caaacaaaga atctgagctg cattttaca    9840
gaacagaaat gcaacgcgag agcgctattt taccaacaaa gaatctatac ttctttttg    9900
ttctacaaaa atgcatcccg agagcgctat ttttctaaca aagcatctta gattactttt    9960
tttctccttt gtgcgctcta taatgcagtc tcttgataac tttttgcact gtaggtccgt   10020
taaggttaga agaaggctac tttggtgtct attttctctt ccataaaaaa agcctgactc   10080
cacttcccgc gtttactgat tactagcgaa gctgcgggtg cattttttca agataaaggc   10140
atccccgatt atattctata ccgatgtgga ttgcgcatac tttgtgaaca gaaagtgata   10200
gcgttgatga ttcttcattg gtcagaaaat tatgaacggt ttcttctatt ttgtctctat   10260
atactacgta taggaaatgt ttacatttc gtattgtttt cgattcactc tatgaatagt   10320
tcttactaca atttttttgt ctaaagagta atactagaga taaacataaa aaatgtagag   10380
gtcgagttta gatgcaagtt caaggagcga aggtggatg ggtaggttat atagggatat   10440
agcacagaga tatatagcaa agagatactt ttgagcaatg tttgtggaag cggtattcgc   10500
aatattttag tagctcgtta cagtccggtg cgttttggt tttttgaaag tgcgtcttca   10560
gagcgctttt ggttttcaaa agcgctctga agttcctata ctttctagag aataggaact   10620
tcggaatagg aacttcaaag cgtttccgaa acgagcgct tccgaaaatg caacgcgagc   10680
tgcgcacata cagctcactg ttcacgtcgc acctatatct gcgtgttgcc tgtatatata   10740
tatacatgag aagaacggca tagtgcgtgt ttatgcttaa atgcgtactt atatgcgtct   10800
atttatgtag gatgaaaggt agtctagtac ctcctgtgat attatcccat tccatgcggg   10860
gtatcgtatg cttccttcag cactaccctt tagctgttct atatgctgcc actcctcaat   10920
tggattagtc tcatccttca atgctatcat ttcctttgat attcgatcct aggcatagta   10980
ccgagaaact agtgcgaagt agtgatcagg tattgctgtt atctgatgag tatacgttgt   11040
cctggccacg gcagaagcac gcttatcgct ccaatttccc acaacattag tcaactccgt   11100
taggcccttc attgaaagaa atgaggtcat caaatgtctt ccaatgtgag attttgggcc   11160
atttttata gcaaagattg aataaggcgc attttctcc a   11201
```

<210> SEQ ID NO 26
<211> LENGTH: 11204

<212> TYPE: DNA
<213> ORGANISM: Saccharomyces cerevisiae

<400> SEQUENCE: 26

| | | | | | |
|---|---|---|---|---|---|
| aagcttcgcg | gccgcggagg | tctgcttcac | gagcgcggtg | tgcgcctagt | attgccccga | 60 |
| cggtccgggt | gcctatccct | agatttcgtc | gtgccccgac | ccaaatagtt | aaacgtgtgg | 120 |
| tttatgggtg | caccagggct | ttatcgtgtt | ttatatcgat | ggcgatttgt | gcctccagtg | 180 |
| tattttgta | tatccaatta | aggtttctta | cctaatttta | ttttatcat | ctttagttaa | 240 |
| tgctggtttg | ctctgtttct | gctgctttct | gtgcggttct | cctcttctct | tgtttcttcg | 300 |
| tgttgtcccc | catcgccgat | gggcttatat | ggcgtatata | tatagagcga | gttttacgt | 360 |
| cgaagatcat | ctcagtttgc | ttgatagcct | ttctactta | ttactttcgt | ttttaacctc | 420 |
| attatacttt | agttttcttt | gatcggtttt | tttctctgta | tacttaaaag | ttcaaatcaa | 480 |
| agaaacatac | aaaactacgt | ttatatcaat | tacatatgcg | gtccggatcc | agtttaaaca | 540 |
| gtagctttgg | acttcttcgc | cagaggtttg | gtcaagtctc | caatcaaggt | tgtcggcttg | 600 |
| tctaccttgc | cagaaattta | cgaaaagatg | gaaaagggtc | aaatcgttgg | tagatacgtt | 660 |
| gttgacactt | ctaaataagc | gaatttctta | tgatttatga | tttttattat | taaataagtt | 720 |
| ataaaaaaaa | taagtgtata | caaattttaa | agtgactctt | aggttttaaa | acgaaaattc | 780 |
| ttgttcttga | gtaactcttt | cctgtaggtc | aggttgcttt | ctcaggtata | gcatgaggtc | 840 |
| gctcttattg | accacacctc | taccggcatg | ccgagcaaat | gcctgcaaat | cgctccccat | 900 |
| ttcacccaat | tgtagatatg | ctaactccag | caatgagttg | atgaatctcg | gtgtgtattt | 960 |
| tatgtcctca | gaagacaaca | cctgttgtaa | tcgttcttcc | acacggatcg | cggccgcttg | 1020 |
| atcctctacg | ccggacgcat | cgtggccggc | atcaccggcg | ccacaggtgc | ggttgctggc | 1080 |
| gcctatatcg | ccgacatcac | cgatgggaa | gatcgggctc | gccacttcgg | gctcatgagc | 1140 |
| gcttgtttcg | gcgtgggtat | ggtggcaggc | cccgtggccg | ggggactgtt | gggcgccatc | 1200 |
| tccttgcatg | caccattcct | tgcggcggcg | gtgctcaacg | gcctcaacct | actactgggc | 1260 |
| tgcttcctaa | tgcaggagtc | gcataaggga | gagcgtcgac | cgatgccctt | gagagccttc | 1320 |
| aacccagtca | gctccttccg | gtgggcgcgg | ggcatgacta | tcgtcgccgc | acttatgact | 1380 |
| gtcttcttta | tcatgcaact | cgtaggacag | gtgccggcag | cgctctgggt | cattttcggc | 1440 |
| gaggaccgct | ttcgctggag | cgcgacgatg | atcggcctgt | cgcttgcggt | attcggaatc | 1500 |
| ttgcacgccc | tcgctcaagc | cttcgtcact | ggtcccgcca | ccaaacgttt | cggcgagaag | 1560 |
| caggccatta | tcgccggcat | ggcggccgac | gcgctgggct | acgtcttgct | ggcgttcgcg | 1620 |
| acgcgaggct | ggatggcctt | ccccattatg | attcttctcg | cttccggcgg | catcgggatg | 1680 |
| cccgcgttgc | aggccatgct | gtccaggcag | gtagatgacg | accatcaggg | acagcttcaa | 1740 |
| ggatcgctcg | cggctcttac | cagcctaact | tcgatcactg | gaccgctgat | cgtcacggcg | 1800 |
| atttatgccg | cctcggcgag | cacatggaac | gggttggcat | ggattgtagg | cgccgcccta | 1860 |
| taccttgtct | gcctccccgc | gttgcgtcgc | ggtgcatgga | gccgggccac | ctcgacctga | 1920 |
| atggaagccg | gcggcacctc | gctaacggat | tcaccactcc | aagaattgga | gccaatcaat | 1980 |
| tcttgcggag | aactgtgaat | gcgcaaacca | acccttggca | gaacatatcc | atcgcgtccg | 2040 |
| ccatctccag | cagccgcacg | cggcgcatct | cgggcagcgt | tgggtcctgg | ccacgggtgc | 2100 |
| gcatgatcgt | gctcctgtcg | ttgaggaccc | ggctaggctg | gcggggttgc | cttactggtt | 2160 |
| agcagaatga | atcaccgata | cgcgagcgaa | cgtgaagcga | ctgctgctgc | aaaacgtctg | 2220 |

-continued

```
cgacctgagc aacaacatga atggtcttcg gtttccgtgt ttcgtaaagt ctggaaacgc   2280
ggaagtcagc gccctgcacc attatgttcc ggatctgcat cgcaggatgc tgctggctac   2340
cctgtggaac acctacatct gtattaacga agcgctggca ttgaccctga gtgattttc    2400 tctggtcccg ccgcatccat accgccagtt gtttaccctc acaacgttcc agtaaccggg   2460
catgttcatc atcagtaacc cgtatcgtga gcatcctctc tcgtttcatc ggtatcatta   2520
cccccatgaa cagaaattcc cccttacacg gaggcatcaa gtgaccaaac aggaaaaaac   2580
cgcccttaac atgggcgct ttatcagaag ccagacatta cgcttctgg agaaactcaa     2640 cgagctggac gcggatgaac aggcagacat ctgtgaatcg cttcacgacc acgctgatga   2700
gctttaccgc agctgcctcg cgcgtttcgg tgatgacggt gaaaacctct gacacatgca   2760
gctcccggag acggtcacag cttgtctgta agcggatgcc gggagcagac aagcccgtca   2820
gggcgcgtca gcgggtgttg gcgggtgtcg gggcgcagcc atgacccagt cacgtagcga   2880
tagcggagtg tatactggct taactatgcg gcatcagagc agattgtact gagagtgcac   2940
gatatccggt gtgaaatacc gcacagatgc gtaaggagaa ataccgcat caggcgctct    3000 tccgcttcct cgctcactga ctcgctgcgc tcggtcgttc ggctgcggcg agcggtatca   3060
gctcactcaa aggcggtaat acggttatcc acagaatcag gggataacgc aggaaagaac   3120
atgtgagcaa aaggccagca aaaggccagg aaccgtaaaa aggccgcgtt gctggcgttt   3180
ttccataggc tccgcccccc tgacgagcat cacaaaaatc gacgctcaag tcagaggtgg   3240
cgaaacccga caggactata agataccag gcgtttcccc ctggaagctc cctcgtgcgc     3300
tctcctgttc cgaccctgcc gcttaccgga tacctgtccg ccttctccc ttcgggaagc    3360 gtggcgcttt ctcaatgctc acgctgtagg tatctcagtt cggtgtaggt cgttcgctcc   3420
aagctgggct gtgtgcacga accccccgtt cagcccgacc gctgcgcctt atccggtaac   3480
tatcgtcttg agtccaaccc ggtaagacac gacttatcgc cactggcagc agccactggt   3540
aacaggatta gcagagcgag gtatgtaggc ggtgctacag agttcttgaa gtggtggcct   3600
aactacggct acactagaag gacagtattt ggtatctgcg ctctgctgaa gccagttacc   3660
ttcggaaaaa gagttggtag ctcttgatcc ggcaaacaaa ccaccgctgg tagcggtggt   3720 tttttgttt gcaagcagca gattacgcgc agaaaaaaag gatctcaaga agatcctttg    3780
atcttttcta cggggtctga cgctcagtgg aacgaaaact cacgttaagg gattttggtc   3840
atgagattat caaaaaggat cttcacctag atccttttaa attaaaaatg aagttttaaa   3900
tcaatctaaa gtatatatga gtaaacttgg tctgacagtt accaatgctt aatcagtgag   3960
gcacctatct cagcgatctg tctatttcgt tcatccatag ttgcctgact ccccgtcgtg   4020
tagataacta cgatacggga gggcttacca tctggcccca gtgctgcaat gataccgcga   4080
gacccacgct caccggctcc agatttatca gcaataaacc agccagccgg aagggccgag   4140
cgcagaagtg gtcctgcaac tttatccgcc tccatccagt ctattaattg ttgccgggaa   4200
gctagagtaa gtagttcgcc agttaatagt ttgcgcaacg ttgttgccat tgctgcaggc   4260
atcgtggtgt cacgctcgtc gtttggtatg gcttcattca gctccggttc caacgatca    4320 aggcgagtta catgatcccc catgttgtgc aaaaaagcgg ttagctcctt cggtcctccg   4380
atcgttgtca gaagtaagtt ggccgcagtg ttatcactca tggttatggc agcactgcat   4440
aattctctta ctgtcatgcc atccgtaaga tgcttttctg tgactggtga gtactcaacc   4500
aagtcattct gagaatagtg tatgcggcga ccgagttgct cttgcccggc gtcaacacgg   4560
gataataccg cgccacatag cagaacttta aaagtgctca tcattggaaa acgttcttcg   4620
```

-continued

```
gggcgaaaac tctcaaggat cttaccgctg ttgagatcca gttcgatgta acccactcgt    4680
gcacccaact gatcttcagc atcttttact ttcaccagcg tttctgggtg agcaaaaaca    4740
ggaaggcaaa atgccgcaaa aaagggaata agggcgacac ggaaatgttg aatactcata    4800
ctcttccttt ttcaatatta ttgaagcatt tatcagggtt attgtctcat gagcggatac    4860
atatttgaat gtatttagaa aaataaacaa ataggggttc cgcgcacatt tccccgaaaa    4920
gtgccacctg acgtctaaga accattatt atcatgacat taacctataa aaataggcgt    4980
atcacgaggc cctttcgtct tcaagaattc cacggactat agactatact agtatactcc    5040
gtctactgta cgatacactt ccgctcaggt ccttgtcctt taacgaggcc ttaccactct    5100
tttgttactc tattgatcca gctcagcaaa ggcagtgtga tctaagattc tatcttcgcg    5160
atgtagtaaa actagctaga ccgagaaaga gactagaaat gcaaaggca cttctacaat    5220 ggctgccatc attattatcc gatgtgacgc tgcagaagca gaaatacacg cggtcagtga    5280
agctattccg ctattgaata acctcagtca ccttgtgcaa gaacttaaca agaaaccaat    5340
tattaaaggc ttacttactg atagtagatc aacgatcagt ataattaagt ctacaaatga    5400
agagaaattt agaaacagat tttttggcac aaaggcaatg agacttagag atgaagtatc    5460
aggtaataat ttatacgtat actacatcga gaccaagaag aacattgctg atgtgatgac    5520
aaaacctctt ccgataaaaa catttaaact attaactaac aaatggattc attagatcta    5580
ttacattatg ggtggtatgt tggaataaaa atcaactatc atctactaac tagtatttac    5640
gttactagta tattatcata tacggtgtta gaagatgacg caaatgatga gaaatagtca    5700
tctaaattag tggaagctga aacgcaagga ttgataatgt aataggatca atgaatatta    5760
acatataaaa tgatgataat aatatttata gaattgtgta gaattgcaga ttccctttta    5820
tggattccta aatcctcgag gagaacttct agtatatcta catacctaat attattgcct    5880
tattaaaaat ggaatcccaa caattacatc aaaatccaca ttctcttcaa aatcaattgt    5940
cctgtacttc cttgttcatg tgtgttcaaa aacgttatat ttataggata attatactct    6000
atttctcaac aagtaattgg ttgtttggcc gagcggtcta aggcgcctga ttcaagaaat    6060
atcttgaccg cagttaactg tgggaatact caggtatcgt aagatgcaag agttcgaatc    6120
tcttagcaac cattattttt ttcctcaaca taacgagaac acacagggc gctatcgcac    6180 agaatcaaat tcgatgactg gaaattttt gttaatttca gaggtcgcct gacgcatata    6240 ccttttcaa ctgaaaaatt gggagaaaaa ggaaaggtga gagccgcgga accggctttt    6300
catatagaat agagaagcgt tcatgactaa atgcttgcat cacaatactt gaagttgaca    6360
atattattta aggacctatt gttttttcca ataggtggtt agcaatcgtc ttactttcta    6420
acttttctta ccttttacat ttcagcaata tatatatata tatttcaagg ataaccatt    6480 ctaatgtctg cccctaagaa gatcgtcgtt ttgccaggtg accacgttgg tcaagaaatc    6540
acagccgaag ccattaaggt tcttaaagct atttctgatg ttcgttccaa tgtcaagttc    6600
gatttcgaaa atcatttaat tggtggtgct gctatcgatg ctacaggtgt cccacttcca    6660
gatgaggcgc tggaagcctc caagaaggtt gatgccgttt tgttaggtgc tgtgggtggt    6720
cctaaatggg gtaccggtag tgttagacct gaacaaggtt tactaaaaat ccgtaaagaa    6780
cttcaattgt acgccaactt aagaccatgt aactttgcat ccgactctct tttagactta    6840
tctccaatca agccacaatt tgctaaaggt actgacttcg ttgttgtcag agaattagtg    6900
ggaggtattt actttggtaa gagaaaggaa gacgatggtg atggtgtcgc ttgggatagt    6960
```

-continued

```
gaacaataca ccgttccaga agtgcaaaga atcacaagaa tggccgcttt catggcccta    7020
caacatgagc caccattgcc tatttggtcc ttggataaag ctaatgtttt ggcctcttca    7080
agattatgga gaaaaactgt ggaggaaacc atcaagaacg aattccctac attgaaggtt    7140
caacatcaat tgattgattc tgccgccatg atcctagtta agaacccaac ccacctaaat    7200
ggtattataa tcaccagcaa catgtttggt gatatcatct ccgatgaagc ctccgttatc    7260
ccaggttcct tgggtttgtt gccatctgcg tccttggcct ctttgccaga caagaacacc    7320
gcatttggtt tgtacgaacc atgccacggt tctgctccag atttgccaaa gaataaggtc    7380
aaccctatcg ccactatctt gtctgctgca atgatgttga aattgtcatt gaacttgcct    7440
gaagaaggta aggccattga agatgcagtt aaaaaggttt tggatgcagg tatcagaact    7500
ggtgatttag gtggttccaa cagtaccacg gaagtcggtg atgctgtcgc cgaagaagtt    7560
aagaaaatcc ttgcttaaaa agattctctt tttttatgat atttgtacat aaactttata    7620
aatgaaattc ataatagaaa cgacacgaaa ttacaaaatg gaatatgttc atagggtaga    7680
cgaaactata tacgcaatct acatacattt atcaagaagg agaaaaagga ggatgtaaag    7740
gaatacaggt aagcaaattg atactaatgg ctcaacgtga taaggaaaaa gaattgcact    7800
ttaacattaa tattgacaag gaggagggca ccacacaaaa agttaggtgt aacagaaaat    7860
catgaaacta tgattcctaa tttatatatt ggaggatttt ctctaaaaaa aaaaaaatac    7920
aacaaataaa aaacactcaa tgacctgacc atttgatgga gtttaagtca ataccttctt    7980
gaaccatttc ccataatggt gaaagttccc tcaagaattt tactctgtca gaaacggcct    8040
taacgacgta gtcgacctcc tcttcagtac taaatctacc aataccaaat ctgatggaag    8100
aatgggctaa tgcatcatcc ttacccagcg catgtaaaac ataagaaggt tctagggaag    8160
cagatgtaca ggctgaaccc gaggataatg cgatatccct tagtgccatc aataaagatt    8220
ctccttccac gtaggcgaaa gaaacgttaa cacaccctgg ataacgatga tctggagatc    8280
cgttcaacgt ggtatgttca gcggataata gacctttgac taatttatcg gatagtcttt    8340
tgatgtgagc ttggtcgttg tcaaattctt tcttcatcaa tctcgcagct tcaccaaatc    8400
ccgctaccaa tgggggggcc aaagtaccag atctcaatcc tctctcttgg ccaccaccgg    8460
atagtaaagg ttctaatcta actcttggtc tccttcttac atagatggca cctattccct    8520
ttggaccgta aatcttgtga gaagaaattg atagtaaatc aatgttcatt tcattgacat    8580
caatgtgaat cttaccatag gcttgtgcgg cgtcagtatg aaagtagatc ttattctttc    8640
tacaaattgc accaatttct ttaataggtt gaatgacacc gatttcatta ttgacagcca    8700
tcacagagac gagacaggta tctggtctaa tggcatcttc caattccttc aaatcgataa    8760
gaccttgatc gtccacattt aggaaagtga cttcaaatcc ctccttcatc atggcccgtg    8820
cggcttccaa gacacacttg tgttccgttc tagtggtgat gatgtgtttc ttagtcttct    8880
tataaaatct tgggacaccc ttaagaacca tattattaga ttcggtcgct cccgaagtga    8940
atattatttc cttggggtcg gcattgatca tctttgctac gtaagctcta gcattttcca    9000
cagcagtatt tgtttcccaa ccgtaagagt gagtgttgga atgaggatta ccataaagtc    9060
ccgtataaaa cttcaacatc gtatccaaaa ccctagggtc tgttggtgta gtggcttgca    9120
tgtcaagata tatgggacga gtaccaaaac ctgtgttttc ttgataagca tggctcattg    9180
cagtgctacc agaagctact acagcatctg gggtggtacc ggatgcactc gcacgggcac    9240
tagcctgtgc ctttgcagca gcctgaatat cggtatgcgt ttccagagag aagttgtcgt    9300
ctaacttcac gcctgctgca gtctcaatga tattcgaata cgctttgagg agatacagcc    9360
```

-continued

```
taatatccga caaactgttt tacagattta cgatcgtact tgttacccat cattgaattt     9420
tgaacatccg aacctgggag ttttccctga aacagatagt atatttgaac ctgtataata     9480
atatatagtc tagcgcttta cggaagacaa tgtatgtatt tcggttcctg gagaaactat     9540
tgcatctatt gcataggtaa tcttgcacgt cgcatccccg gttcattttc tgcgtttcca     9600
tcttgcactt caatagcata tctttgttaa cgaagcatct gtgcttcatt ttgtagaaca     9660
aaaatgcaac gcgagagcgc taattttttca aacaaagaat ctgagctgca tttttacaga     9720
acagaaatgc aacgcgaaag cgctatttta ccaacgaaga atctgtgctt cattttttgta     9780 aaacaaaaat gcaacgcgag agcgctaatt tttcaaacaa agaatctgag ctgcatttttt     9840 acagaacaga aatgcaacgc gagagcgcta ttttaccaac aaagaatcta tacttctttt     9900
ttgttctaca aaaatgcatc ccgagagcgc tattttttcta acaaagcatc ttagattact     9960 tttttttctcc tttgtgcgct ctataatgca gtctcttgat aacttttttgc actgtaggtc    10020 cgttaaggtt agaagaaggc tactttggtg tctatttttct cttccataaa aaaagcctga    10080
ctccacttcc cgcgtttact gattactagc gaagctgcgg gtgcattttt tcaagataaa    10140
ggcatccccg attatattct ataccgatgt ggattgcgca tactttgtga acagaaagtg    10200
atagcgttga tgattcttca ttggtcagaa aattatgaac ggtttcttct attttgtctc    10260
tatatactac gtataggaaa tgtttacatt ttcgtattgt tttcgattca ctctatgaat    10320
agttcttact acaattttttt tgtctaaaga gtaatactag agataaacat aaaaaatgta    10380
gaggtcgagt ttagatgcaa gttcaaggag cgaaaggtgg atgggtaggt tatataggga    10440
tatagcacag agatatatag caaagagata cttttgagca atgtttgtgg aagcggtatt    10500
cgcaatattt tagtagctcg ttacagtccg gtgcgttttt ggttttttga agtgcgtct    10560 tcagagcgct tttggttttc aaaagcgctc tgaagttcct atactttcta gagaatagga    10620
acttcggaat aggaacttca aagcgtttcc gaaaacgagc gcttccgaaa atgcaacgcg    10680
agctgcgcac atacagctca ctgttcacgt cgcacctata tctgcgtgtt gcctgtatat    10740
atatatacat gagaagaacg gcatagtgcg tgtttatgct taaatgcgta cttatatgcg    10800
tctatttatg taggatgaaa ggtagtctag tacctcctgt gatattatcc cattccatgc    10860
ggggtatcgt atgcttcctt cagcactacc ctttagctgt tctatatgct gccactcctc    10920
aattggatta gtctcatcct tcaatgctat catttccttt gatattcgat cctaggcata    10980
gtaccgagaa actagtgcga agtagtgatc aggtattgct gttatctgat gagtatacgt    11040
tgtcctggcc acggcagaag cacgcttatc gctccaattt cccacaacat tagtcaactc    11100
cgttaggccc ttcattgaaa gaatgaggt catcaaatgt cttccaatgt gagattttgg    11160
gccatttttt atagcaaaga ttgaataagg cgcatttttc ttca                     11204
```

<210> SEQ ID NO 27
<211> LENGTH: 12008
<212> TYPE: DNA
<213> ORGANISM: Saccharomyces cerevisiae
<400> SEQUENCE: 27

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
```

-continued

```
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcaagcggcc gcagtacgta atgcggtatc gtgaaagcga    420
aaaaaaaact aacagtagat aagacagata gacagataga gatggacgag aaacagggg    480 ggagaaaagg ggaaaagaga aggaaagaaa gactcatcta tcgcagataa gacaatcaac    540
cctcatggcg cctccaacca ccatccgcac tagggaccaa gcgctcgcac cgttagcaac    600
gcttgactca caaaccaact gccggctgaa agagcttgtg caatgggagt gccaattcaa    660
aggagccgaa tacgtctgct cgcctttta gaggcttttt gaacactgca ttgcacccga    720
caaatcagcc actaactacg aggtcacgga cacatatacc aatagttaaa aattacatat    780
actctatata gcacagtagt gtgataaata aaaattttg ccaagacttt tttaaactgc    840
acccgacaga tcaggtctgt gcctactatg cacttatgcc cggggtcccg ggaggagaaa    900
aaacgagggc tgggaaatgt ccgtggactt taaacgctcc ggttagcag agtagcaggg    960 ctttcggctt tggaaattta ggtgacttgt tgaaaagca aatttgggc tcagtaatgc    1020 cactgcagtg gctatcacg ccaggactgc gggagtggcg ggcaaaca cacccgcgat    1080 aaagagcgcg atgaatataa aaggggccca atgttacgtc ccgttatat ggagttcttc    1140 ccatacaaac ttaagagtcc aattagcttc atcgccaata aaaaaacaag ctaaacctaa    1200
ttctaacaag cacatatgcg gtccggatcc agtttaaaca gtagctttgg acttcttcgc    1260
cagaggtttg gtcaagtctc caatcaaggt tgtcggcttg tctaccttgc cagaaattta    1320
cgaaaagatg gaaaagggtc aaatcgttgg tagatacgtt gttgacactt ctaaataagc    1380
gaatttctta tgattatga ttttattat taaataagtt ataaaaaaa taagtgtata    1440 caaattttaa agtgactctt aggttttaaa acgaaaattc ttgttcttga gtaactcttt    1500
cctgtaggtc aggttgcttt ctcaggtata gcatgaggtc gctcttattg accacacctc    1560
taccggcatg ccgagcaaat gcctgcaaat cgctccccat ttcacccaat tgtagatatg    1620
ctaactccag caatgagttg atgaatctcg gtgtgtattt tatgtcctca gaagacaaca    1680
cctgttgtaa tcgttcttcc acacggatcg cggccgcttg atcctctacg ccggacgcat    1740
cgtggccggc atcaccggcg ccacaggtgc ggttgctggc gcctatatcg ccgacatcac    1800
cgatggggaa gatcgggctc gccacttcgg gctcatgagc gcttgtttcg gcgtgggtat    1860
ggtggcaggc cccgtggccg ggggactgtt gggcgccatc tccttgcatg caccattcct    1920
tgcggcggcg gtgctcaacg gcctcaacct actactgggg tgcttcctaa tgcaggagtc    1980
gcataaggga gagcgtcgac cgatgccctt gagagccttc aacccagtca gctccttccg    2040
gtgggcgcgg ggcatgacta tcgtcgccgc acttatgact gtcttcttta tcatgcaact    2100
cgtaggacag gtgccggcag cgctctgggt cattttcggc gaggaccgct ttcgctggag    2160
cgcgacgatg atcggcctgt cgcttgcggt attcggaatc ttgcacgccc tcgctcaagc    2220
cttcgtcact ggtcccgcca ccaaacgttt cggcgagaag caggccatta tcgccggcat    2280
ggcggccgac gcgctgggct acgtcttgct ggcgttcgcg acgcgaggct ggatggcctt    2340
ccccattatg attcttctcg cttccggcgg catcgggatg cccgcgttgc aggccatgct    2400
gtccaggcag gtagatgacg accatcaggg acagcttcaa ggatcgctcg cggctcttac    2460
cagcctaact tcgatcactg gaccgctgat cgtcacggcg atttatgccg cctcggcgag    2520
cacatggaac gggttggcat ggattgtagg cgccgcccta taccttgtct gcctccccgc    2580
gttgcgtcgc ggtgcatgga gccgggccac ctcgacctga atggaagccg gcggcacctc    2640
```

```
gctaacggat tcaccactcc aagaattgga gccaatcaat tcttgcggag aactgtgaat    2700
gcgcaaacca accetttggca gaacatatcc atcgcgtccg ccatctccag cagccgcacg    2760
cggcgcatct cgggcagcgt tgggtcctgg ccacgggtgc gcatgatcgt gctcctgtcg    2820
ttgaggaccc ggctaggctg gcggggttgc cttactggtt agcagaatga atcaccgata    2880
cgcgagcgaa cgtgaagcga ctgctgctgc aaaacgtctg cgacctgagc aacaacatga    2940
atggtcttcg gtttccgtgt ttcgtaaagt ctggaaacgc ggaagtcagc gccctgcacc    3000
attatgttcc ggatctgcat cgcaggatgc tgctggctac cctgtggaac acctacatct    3060
gtattaacga agcgctggca ttgaccctga gtgattttc tctggtcccg ccgcatccat    3120
accgccagtt gtttaccctc acaacgttcc agtaaccggg catgttcatc atcagtaacc    3180
cgtatcgtga gcatcctctc tcgtttcatc ggtatcatta cccccatgaa cagaaattcc    3240
cccttacacg gaggcatcaa gtgaccaaac aggaaaaaac cgcccttaac atggcccgct    3300
ttatcagaag ccagacatta acgcttctgg agaaactcaa cgagctggac gcggatgaac    3360
aggcagacat ctgtgaatcg cttcacgacc acgctgatga gctttaccgc agctgcctcg    3420
cgcgtttcgg tgatgacggt gaaaacctct gacacatgca gctcccggag acggtcacag    3480
cttgtctgta gcggatgcc gggagcagac aagcccgtca gggcgcgtca gcgggtgttg    3540
gcgggtgtcg gggcgcagcc atgacccagt cacgtagcga tagcggagtg tatactggct    3600
taactatgcg gcatcagagc agattgtact gagagtgcac gatatccggt gtgaaatacc    3660
gcacagatgc gtaaggagaa ataccgcat caggcgctct ccgcttcct cgctcactga    3720 ctcgctgcgc tcggtcgttc ggctgcggcg agcggtatca gctcactcaa aggcggtaat    3780
acggttatcc acagaatcag gggataacgc aggaaagaac atgtgagcaa aaggccagca    3840
aaaggccagg aaccgtaaaa aggccgcgtt gctggcgttt ttccataggc tccgcccccc    3900
tgacgagcat cacaaaaatc gacgctcaag tcagaggtgg cgaaacccga caggactata    3960
aagataccag gcgtttcccc ctggaagctc cctcgtgcgc tctcctgttc cgaccctgcc    4020
gcttaccgga tacctgtccg cctttctccc ttcgggaagc gtggcgcttt ctcaatgctc    4080
acgctgtagg tatctcagtt cggtgtaggt cgttcgctcc aagctgggct gtgtgcacga    4140
accccccgtt cagcccgacc gctgcgcctt atccggtaac tatcgtcttg agtccaaccc    4200
ggtaagacac gacttatcgc cactggcagc agccactggt aacaggatta gcagagcgag    4260
gtatgtaggc ggtgctacag agttcttgaa gtggtggcct aactacggct acactagaag    4320
gacagtattt ggtatctgcg ctctgctgaa gccagttacc ttcggaaaaa gagttggtag    4380
ctcttgatcc ggcaaacaaa ccaccgctgg tagcggtggt ttttttgttt gcaagcagca    4440
gattacgcgc agaaaaaaag gatctcaaga agatcctttg atcttttcta cggggtctga    4500
cgctcagtgg aacgaaaact cacgttaagg gattttggtc atgagattat caaaaaggat    4560
cttcacctag atccttttaa attaaaaatg aagttttaaa tcaatctaaa gtatatatga    4620
gtaaacttgg tctgacagtt accaatgctt aatcagtgag gcacctatct cagcgatctg    4680
tctatttcgt tcatccatag ttgcctgact ccccgtcgtg tagataacta cgatacggga    4740
gggcttacca tctggcccca gtgctgcaat gataccgcga gacccacgct caccggctcc    4800
agatttatca gcaataaacc agccagccgg aagggccgag cgcagaagtg gtcctgcaac    4860
tttatccgcc tccatccagt ctattaattg ttgccgggaa gctagagtaa gtagttcgcc    4920
agttaatagt ttgcgcaacg ttgttgccat tgctgcaggc atcgtggtgt cacgctcgtc    4980
```

```
gtttggtatg gcttcattca gctccggttc ccaacgatca aggcgagtta catgatcccc    5040
catgttgtgc aaaaaagcgg ttagctcctt cggtcctccg atcgttgtca gaagtaagtt    5100
ggccgcagtg ttatcactca tggttatggc agcactgcat aattctctta ctgtcatgcc    5160
atccgtaaga tgcttttctg tgactggtga gtactcaacc aagtcattct gagaatagtg    5220
tatgcggcga ccgagttgct cttgcccggc gtcaacacgg gataataccg cgccacatag    5280
cagaacttta aaagtgctca tcattggaaa acgttcttcg gggcgaaaac tctcaaggat    5340
cttaccgctg ttgagatcca gttcgatgta acccactcgt gcacccaact gatcttcagc    5400
atcttttact ttcaccagcg tttctgggtg agcaaaaaca ggaaggcaaa atgccgcaaa    5460
aaagggaata agggcgacac ggaaatgttg aatactcata ctcttccttt tcaatatta    5520 ttgaagcatt tatcagggtt attgtctcat gagcggatac atatttgaat gtatttagaa    5580
aaataaacaa ataggggttc gcgcacatt tccccgaaaa gtgccacctg acgtctaaga    5640
aaccattatt atcatgacat taacctataa aaataggcgt atcacgaggc cctttcgtct    5700
tcaagaattc cacggactat agactatact agtatactcc gtctactgta cgatacactt    5760
ccgctcaggt ccttgtcctt taacgaggcc ttaccactct tttgttactc tattgatcca    5820
gctcagcaaa ggcagtgtga tctaagattc tatcttcgcg atgtagtaaa actagctaga    5880
ccgagaaaga gactagaaat gcaaaaggca cttctacaat ggctgccatc attattatcc    5940
gatgtgacgc tgcagaagca gaaatacacg cggtcagtga agctattccg ctattgaata    6000
acctcagtca ccttgtgcaa gaacttaaca agaaaccaat tattaaaggc ttacttactg    6060
atagtagatc aacgatcagt ataattaagt ctacaaatga agagaaattt agaaacagat    6120
tttttggcac aaaggcaatg agacttagag atgaagtatc aggtaataat ttatacgtat    6180
actacatcga gaccaagaag aacattgctg atgtgatgac aaaacctctt ccgataaaaa    6240
catttaaact attaactaac aaatggattc attagatcta ttacattatg ggtggtatgt    6300
tggaataaaa atcaactatc atctactaac tagtatttac gttactagta tattatcata    6360
tacggtgtta aagatgacg caaatgatga gaaatagtca tctaaattag tggaagctga    6420
aacgcaagga ttgataatgt aataggatca atgaatatta acatataaaa tgatgataat    6480
aatatttata gaattgtgta gaattgcaga ttcccttttta tggattccta aatcctcgag    6540
gagaacttct agtatatcta catacctaat attattgcct tattaaaaat ggaatcccaa    6600
caattacatc aaaatccaca ttctcttcaa aatcaattgt cctgtacttc cttgttcatg    6660
tgtgttcaaa aacgttatat ttataggata attatactct atttctcaac aagtaattgg    6720
ttgtttggcc gagcggtcta aggcgcctga ttcaagaaat atcttgaccg cagttaactg    6780
tgggaatact caggtatcgt aagatgcaag agttcgaatc tcttagcaac cattattttt    6840
ttcctcaaca taacgagaac acacaggggc gctatcgcac agaatcaaat tcgatgactg    6900 gaaattttt gttaatttca gaggtcgcct gacgcatata ccttttttcaa ctgaaaaatt    6960 gggagaaaaa ggaaaggtga gagccgcgga accggctttt catatagaat agagaagcgt    7020
tcatgactaa atgcttgcat cacaatactt gaagttgaca atattattta aggacctatt    7080
gttttttcca ataggtggtt agcaatcgtc ttactttcta actttttctta ccttttacat    7140 ttcagcaata tatatatata tatttcaagg atataccatt ctaatgtctg cccctaagaa    7200
gatcgtcgtt ttgccaggtg accacgttgg tcaagaaatc acagccgaag ccattaaggt    7260
tcttaaagct atttctgatg ttcgttccaa tgtcaagttc gatttcgaaa atcatttaat    7320
tggtggtgct gctatcgatg ctacaggtgt cccacttcca gatgaggcgc tggaagcctc    7380
```

-continued

```
caagaaggtt gatgccgttt tgttaggtgc tgtgggtggt cctaaatggg gtaccggtag      7440
tgttagacct gaacaaggtt tactaaaaat ccgtaaagaa cttcaattgt acgccaactt      7500
aagaccatgt aactttgcat ccgactctct tttagactta tctccaatca agccacaatt      7560
tgctaaaggt actgacttcg ttgttgtcag agaattagtg ggaggtattt actttggtaa      7620
gagaaaggaa gacgatggtg atggtgtcgc ttgggatagt gaacaataca ccgttccaga      7680
agtgcaaaga atcacaagaa tggccgcttt catggcccta acatgagc caccattgcc       7740 tatttggtcc ttggataaag ctaatgtttt ggcctcttca agattatgga gaaaaactgt      7800
ggaggaaacc atcaagaacg aattccctac attgaaggtt caacatcaat tgattgattc      7860
tgccgccatg atcctagtta agaacccaac ccacctaaat ggtattataa tcaccagcaa      7920
catgtttggt gatatcatct ccgatgaagc ctccgttatc ccaggttcct tgggtttgtt      7980
gccatctgcg tccttggcct ctttgccaga caagaacacc gcatttggtt tgtacgaacc      8040
atgccacggt tctgctccag atttgccaaa gaataaggtc aaccctatcg ccactatctt      8100
gtctgctgca atgatgttga aattgtcatt gaacttgcct gaagaaggta aggccattga      8160
agatgcagtt aaaaaggttt tggatgcagg tatcagaact ggtgatttag gtggttccaa      8220
cagtaccacg gaagtcggtg atgctgtcgc cgaagaagtt aagaaaatcc ttgcttaaaa      8280
agattctctt tttttatgat atttgtacat aaactttata aatgaaattc ataatagaaa      8340
cgacacgaaa ttacaaaatg gaatatgttc atagggtaga cgaaactata tacgcaatct      8400
acatacattt atcaagaagg agaaaaagga ggatgtaaag gaatacaggt aagcaaattg      8460
atactaatgg ctcaacgtga taaggaaaaa gaattgcact ttaacattaa tattgacaag      8520
gaggagggca ccacacaaaa agttaggtgt aacagaaaat catgaaacta tgattcctaa      8580
tttatatatt ggaggatttt ctctaaaaaa aaaaaaatac aacaaataaa aaacactcaa      8640
tgacctgacc atttgatgga gtttaagtca ataccttctt gaaccatttc ccataatggt      8700
gaaagttccc tcaagaattt tactctgtca gaaacggcct taacgacgta gtcgacctcc      8760
tcttcagtac taaatctacc aataccaaat ctgatgaag aatgggctaa tgcatcatcc      8820
ttacccagcg catgtaaaac ataagaaggt tctagggaag cagatgtaca ggctgaaccc      8880
gaggataatg cgatatccct tagtgccatc aataaagatt ctccttccac gtaggcgaaa      8940
gaaacgttaa cacaccctgg ataacgatga tctggagatc cgttcaacgt ggtatgttca      9000
gcggataata gaccttt gac taatttatcg gatagtcttt tgatgtgagc ttggtcgttg      9060
tcaaattctt tcttcatcaa tctcgcagct tcaccaaatc ccgctaccaa tggggggggcc      9120 aaagtaccag atctcaatcc tctctcttgg ccaccaccgg atagtaaagg ttctaatcta      9180
actcttggtc tccttcttac atagatggca cctattccct ttggaccgta aatcttgtga      9240
gaagaaattg atagtaaatc aatgttcatt tcattgacat caatgtgaat cttaccatag      9300
gcttgtgcgg cgtcagtatg aaagtagatc ttattctttc tacaaattgc accaatttct      9360
ttaataggtt gaatgacacc gatttcatta ttgacagcca tcacagagac gagacaggta      9420
tctggtctaa tggcatcttc caattccttc aaatcgataa gaccttgatc gtccacattt      9480
aggaaagtga cttcaaatcc ctccttcatc atggcccgtg cggcttccaa gacacacttg      9540
tgttccgttc tagtggtgat gatgtgtttc ttagtcttct tataaaatct tgggacaccc      9600
ttaagaacca tattattaga ttcggtcgct cccgaagtga atattattc cttgggtcg        9660 gcattgatca tctttgctac gtaagctcta gcattttcca cagcagtatt tgtttcccaa      9720
```

```
ccgtaagagt gagtgttgga atgaggatta ccataaagtc ccgtataaaa cttcaacatc    9780
gtatccaaaa ccctagggtc tgttggtgta gtggcttgca tgtcaagata tatgggacga    9840
gtaccaaaac ctgtgttttc ttgataagca tggctcattg cagtgctacc agaagctact    9900
acagcatctg gggtggtacc ggatgcactc gcacgggcac tagcctgtgc ctttgcagca    9960
gcctgaatat cggtatgcgt ttccagagag aagttgtcgt ctaacttcac gcctgctgca   10020
gtctcaatga tattcgaata cgctttgagg agatacagcc taatatccga caaactgttt   10080
tacagattta cgatcgtact tgttacccat cattgaattt tgaacatccg aacctgggag   10140 tttttccctga aacagatagt atatttgaac ctgtataata atatatagtc tagcgcttta   10200
cggaagacaa tgtatgtatt tcggttcctg gagaaactat tgcatctatt gcataggtaa   10260
tcttgcacgt cgcatccccg gttcattttc tgcgttccca tcttgcactt caatagcata   10320
tctttgttaa cgaagcatct gtgcttcatt ttgtagaaca aaaatgcaac gcgagagcgc   10380 taattttttca aacaaagaat ctgagctgca tttttacaga acagaaatgc aacgcgaaag   10440
cgctatttta ccaacgaaga atctgtgctt catttttgta aaacaaaaat gcaacgcgag   10500
agcgctaatt tttcaaacaa agaatctgag ctgcattttt acagaacaga atgcaacgc   10560 gagagcgcta ttttaccaac aaagaatcta tacttctttt tgttctaca aaaatgcatc   10620 ccgagagcgc tattttcta acaaagcatc ttagattact ttttttctcc tttgtgcgct   10680
ctataatgca gtctcttgat aacttttgc actgtaggtc cgttaaggtt agaagaaggc   10740
tactttggtg tctatttctct cttccataaa aaaagcctga ctccacttcc cgcgtttact   10800
gattactagc gaagctgcgg gtgcattttt tcaagataaa ggcatcccccg attatattct   10860 ataccgatgt ggattgcgca tactttgtga acagaaagtg atagcgttga tgattcttca   10920
ttggtcagaa aattatgaac ggtttcttct attttgtctc tatatactac gtataggaaa   10980
tgtttacatt ttcgtattgt tttcgattca ctctatgaat agttcttact acaatttttt   11040
tgtctaaaga gtaatactag agataaacat aaaaaatgta gaggtcgagt ttagatgcaa   11100
gttcaaggag cgaaaggtgg atgggtaggt tatatagggg atatagcacag agatatatag   11160 caaagagata cttttgagca atgtttgtgg aagcggtatt cgcaatattt tagtagctcg   11220
ttacagtccg gtgcgttttt ggtttttttga aagtgcgtct tcagagcgct tttggttttc   11280
aaaagcgctc tgaagttcct atactttcta gagaatagga acttcggaat aggaacttca   11340
aagcgtttcc gaaaacgagc gcttccgaaa atgcaacgcg agctgcgcac atacagctca   11400
ctgttcacgt cgcacctata tctgcgtgtt gcctgtatat atatatacat gagaagaacg   11460
gcatagtgcg tgtttatgct taaatgcgta cttatatgcg tctatttatg taggatgaaa   11520
ggtagtctag tacctcctgt gatattatcc cattccatgc ggggtatcgt atgcttcctt   11580
cagcactacc ctttagctgt tctatatgct gccactcctc aattggatta gtctcatcct   11640
tcaatgctat catttccttt gatattcgat cctaggcata gtaccgagaa actagtgcga   11700
agtagtgatc aggtattgct gttatctgat gagtatacgt tgtcctggcc acggcagaag   11760
cacgcttatc gctccaattt cccacaacat tagtcaactc cgttaggccc ttcattgaaa   11820
gaaatgaggt catcaaatgt cttccaatgt gagattttgg gccattttt atagcaaaga   11880 ttgaataagg cgcatttttc tttcaaagctt tattgtacga tctgactaag ttatctttta   11940
ataattggta ttcctgttta ttgcttgaag aattgccggt cctatttact cgttttagga   12000
ctggttca                                                            12008
```

<210> SEQ ID NO 28
<211> LENGTH: 13654
<212> TYPE: DNA
<213> ORGANISM: Saccharomyces cerevisiae

<400> SEQUENCE: 28

```
gaattctcat gtttgacagc ttatcatcga taagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtcctgctcg cttcgctact tggagccact atcgactacg cgatcatggc     360
gaccacaccc gtcctgtgga tcaagcggcc gcagtacgta atgcggtatc gtgaaagcga     420
aaaaaaaact aacagtagat aagacagata gacagataga gatggacgag aaacagggggg     480
ggagaaaagg ggaaagaga aggaaagaaa gactcatcta tcgcagataa gacaatcaac     540
cctcatggcg cctccaacca ccatccgcac tagggaccaa gcgctcgcac cgttagcaac     600
gcttgactca caaaccaact gccggctgaa agagcttgtg caatgggagt gccaattcaa     660
aggagccgaa tacgtctgct cgcctttttaa gaggcttttt gaacactgca ttgcacccga     720
caaatcagcc actaactacg aggtcacgga cacatatacc aatagttaaa aattacatat     780
actctatata gcacagtagt gtgataaata aaaaattttg ccaagacttt tttaaactgc     840
acccgacaga tcaggtctgt gcctactatg cacttatgcc cggggtcccg ggaggagaaa     900
aaacgagggc tgggaaatgt ccgtggactt taaacgctcc gggttagcag agtagcaggg     960
ctttcggctt tggaaattta ggtgacttgt tgaaaaagca aaatttgggc tcagtaatgc    1020
cactgcagtg gcttatcacg ccaggactgc gggagtggcg gggcaaaca cacccgcgat    1080
aaagagcgcg atgaatataa aaggggggcca atgttacgtc ccgttatatt ggagttcttc    1140
ccatacaaac ttaagagtcc aattagcttc atcgccaata aaaaaacaag ctaaacctaa    1200
ttctaacaag cacatatgga agacgccaaa aacataaaga aaggcccggc gccattctat    1260
ccgctggaag atggaaccgc tggagagcaa ctgcataagg ctatgaagag atacgccctg    1320
gttcctggaa caattgcttt tacagatgca catatcgagg tggacatcac ttacgctgag    1380
tacttcgaaa tgtccgttcg gttggcagaa gctatgaaac gatatgggct gaatacaaat    1440
cacagaatcg tcgtatgcag tgaaaactct cttcaattct ttatgccggt gttgggcgcg    1500
ttatttatcg gagttgcagt tgcgcccgcg aacgacattt ataatgaacg tgaattgctc    1560
aacagtatgg gcatttcgca gcctaccgtg gtgttcgttt ccaaaaaggg gttgcaaaaa    1620
attttgaacg tgcaaaaaaa gctcccaatc atccaaaaaa ttattatcat ggattctaaa    1680
acggattacc agggatttca gtcgatgtac acgttcgtca catctcatct acctcccggt    1740
tttaatgaat acgattttgt gccagagtcc ttcgataggg acaagacaat tgcactgatc    1800
atgaactcct ctggatctac tggtctgcct aaaggtgtcg ctctgcctca tagaactgcc    1860
tgcgtgagat tctcgcatgc cagagatcct atttttggca atcaaatcat tccggatact    1920
gcgattttaa gtgttgttcc attccatcac ggttttggaa tgtttactac actcggatat    1980
ttgatatgtg gatttcgagt cgtcttaatg tatagatttg aagaagagct gtttctgagg    2040
agccttcagg attacaagat tcaaagtgcg ctgctggtgc caacccctatt ctccttcttc    2100
gccaaaagca ctctgattga caaatacgat ttatctaatt tacacgaaat tgcttctggt    2160
```

```
ggcgctcccc tctctaagga agtcggggaa gcggttgcca agaggttcca tctgccaggt   2220
atcaggcaag gatatgggct cactgagact acatcagcta ttctgattac acccgagggg   2280
gatgataaac cgggcgcggt cggtaaagtt gttccatttt ttgaagcgaa ggttgtggat   2340
ctggataccg ggaaaacgct gggcgttaat caaagaggcg aactgtgtgt gagaggtcct   2400
atgattatgt ccggttatgt aaacaatccg gaagcgacca acgccttgat tgacaaggat   2460
ggatggctac attctggaga catagcttac tgggacgaag acgaacactt cttcatcgtt   2520
gaccgcctga agtctctgat taagtacaaa ggctatcagg tggctcccgc tgaattggaa   2580
tccatcttgc tccaacaccc caacatcttc gacgcaggtg tcgcaggtct tcccgacgat   2640
gacgccggtg aacttcccgc cgccgttgtt gttttggagc acggaaagac gatgacggaa   2700
aaagagatcg tggattacgt cgccagtcaa gtaacaaccg cgaaaaagtt gcgcggagga   2760
gttgtgtttg tggacgaagt accgaaaggt cttaccggaa aactcgacgc aagaaaaatc   2820
agagagatcc tcataaaggc caagaagggc ggaaagatcg ccgtgtaatt ggatccagtt   2880
taaacagtag ctttggactt cttcgccaga ggtttggtca agtctccaat caaggttgtc   2940
ggcttgtcta ccttgccaga aatttacgaa aagatggaaa agggtcaaat cgttggtaga   3000
tacgttgttg acacttctaa ataagcgaat ttcttatgat ttatgatttt tattattaaa   3060
taagttataa aaaaaataag tgtatacaaa ttttaaagtg actcttaggt tttaaaacga   3120
aaattcttgt tcttgagtaa ctctttcctg taggtcaggt tgctttctca ggtatagcat   3180
gaggtcgctc ttattgacca cacctctacc ggcatgccga gcaaatgcct gcaaatcgct   3240
ccccatttca cccaattgta gatatgctaa ctccagcaat gagttgatga atctcggtgt   3300
gtattttatg tcctcagaag acaacacctg ttgtaatcgt tcttccacac ggatcgcggc   3360
cgcttgatcc tctacgccgg acgcatcgtg gccggcatca ccggcgccac aggtgcggtt   3420
gctggcgcct atatcgccga catcaccgat ggggaagatc gggctcgcca cttcgggctc   3480
atgagcgctt gtttcggcgt gggtatggtg gcaggccccg tggccggggg actgttgggc   3540
gccatctcct tgcatgcacc attccttgcg gcggcggtgc tcaacggcct caacctacta   3600
ctgggctgct tcctaatgca ggagtcgcat aagggagagc gtcgaccgat gcccttgaga   3660
gccttcaacc cagtcagctc cttccggtgg gcgcggggca tgactatcgt cgccgcactt   3720
atgactgtct tctttatcat gcaactcgta ggacaggtgc cggcagcgct ctgggtcatt   3780
ttcggcgagg accgctttcg ctggagcgcg acgatgatcg gcctgtcgct tgcggtattc   3840
ggaatcttgc acgccctcgc tcaagccttc gtcactggtc ccgccaccaa acgtttcggc   3900
gagaagcagg ccattatcgc cggcatggcg gccgacgcgc tgggctacgt cttgctggcg   3960
ttcgcgacgc gaggctggat ggccttcccc attatgattc ttctcgcttc cggcggcatc   4020
gggatgcccg cgttgcaggc catgctgtcc aggcaggtag atgacgacca tcagggacag   4080
cttcaaggat cgctcgcggc tcttaccagc ctaacttcga tcactggacc gctgatcgtc   4140
acggcgattt atgccgcctc ggcgagcaca tggaacgggt tggcatggat tgtaggcgcc   4200
gccctatacc ttgtctgcct ccccgcgttg cgtcgcggtg catggagccg gccacctcg    4260
acctgaatgg aagccggcgg cacctcgcta acggattcac cactccaaga attggagcca   4320
atcaattctt gcggagaact gtgaatgcgc aaaccaaccc ttggcagaac atatccatcg   4380
cgtccgccat ctccagcagc cgcacgcggc gcatctcggg cagcgttggg tcctggccac   4440
gggtgcgcat gatcgtgctc ctgtcgttga ggacccggct aggctggcgg ggttgcctta   4500
ctggttagca gaatgaatca ccgatacgcg agcgaacgtg aagcgactgc tgctgcaaaa   4560
```

-continued

```
cgtctgcgac ctgagcaaca acatgaatgg tcttcggttt ccgtgtttcg taaagtctgg    4620
aaacgcggaa gtcagcgccc tgcaccatta tgttccggat ctgcatcgca ggatgctgct    4680
ggctaccctg tggaacacct acatctgtat taacgaagcg ctggcattga ccctgagtga    4740
tttttctctg gtcccgccgc atccataccg ccagttgttt accctcacaa cgttccagta    4800
accgggcatg ttcatcatca gtaacccgta tcgtgagcat cctctctcgt ttcatcggta    4860
tcattacccc catgaacaga aattcccccct tacacggagg catcaagtga ccaaacagga    4920
aaaaaccgcc cttaacatgg cccgctttat cagaagccag acattaacgc ttctggagaa    4980
actcaacgag ctggacgcgg atgaacaggc agacatctgt gaatcgcttc acgaccacgc    5040
tgatgagctt taccgcagct gcctcgcgcg tttcggtgat gacggtgaaa acctctgaca    5100
catgcagctc ccggagacgg tcacagcttg tctgtaagcg gatgccggga gcagacaagc    5160
ccgtcagggc gcgtcagcgg gtgttggcgg gtgtcgggc gcagccatga cccagtcacg    5220
tagcgatagc ggagtgtata ctggcttaac tatgcggcat cagagcagat tgtactgaga    5280
gtgcacgata tccggtgtga ataccgcac agatgcgtaa ggagaaaata ccgcatcagg    5340
cgctcttccg cttcctcgct cactgactcg ctgcgctcgg tcgttcggct gcggcgagcg    5400
gtatcagctc actcaaaggc ggtaatacgg ttatccacag aatcagggga taacgcagga    5460
aagaacatgt gagcaaaagg ccagcaaaag gccaggaacc gtaaaaaggc cgcgttgctg    5520
gcgtttttcc ataggctccg ccccctgac gagcatcaca aaaatcgacg ctcaagtcag    5580
aggtggcgaa acccgacagg actataaaga taccaggcgt ttccccctgg aagctccctc    5640
gtgcgctctc ctgttccgac cctgccgctt accggatacc tgtccgcctt tctcccttcg    5700
ggaagcgtgg cgctttctca atgctcacgc tgtaggtatc tcagttcggt gtaggtcgtt    5760
cgctccaagc tgggctgtgt gcacgaaccc ccgttcagc ccgaccgctg cgccttatcc    5820
ggtaactatc gtcttgagtc aacccggta agacacgact tatcgccact ggcagcagcc    5880
actggtaaca ggattagcag agcgaggtat gtaggcggtg ctacagagtt cttgaagtgg    5940
tggcctaact acggctacac tagaaggaca gtatttggta tctgcgctct gctgaagcca    6000
gttaccttcg gaaaaagagt tggtagctct tgatccggca acaaaccac cgctggtagc    6060 ggtggttttt tgtttgcaa gcagcagatt acgcgcagaa aaaaggatc tcaagaagat    6120 cctttgatct tttctacggg gtctgacgct cagtggaacg aaaactcacg ttaagggatt    6180
ttggtcatga gattatcaaa aaggatcttc acctagatcc ttttaaatta aaaatgaagt    6240
tttaaatcaa tctaaagtat atatgagtaa acttggtctg acagttacca atgcttaatc    6300
agtgaggcac ctatctcagc gatctgtcta tttcgttcat ccatagttgc ctgactcccc    6360
gtcgtgtaga taactacgat acgggagggc ttaccatctg gccccagtgc tgcaatgata    6420
ccgcgagacc cacgctcacc ggctccagat ttatcagcaa taaccagcc agccggaagg    6480 gccgagcgca gaagtggtcc tgcaacttta tccgcctcca tccagtctat taattgttgc    6540
cgggaagcta gagtaagtag ttcgccagtt aatagtttgc gcaacgttgt tgccattgct    6600
gcaggcatcg tggtgtcacg ctcgtcgttt ggtatggctt cattcagctc cggttcccaa    6660
cgatcaaggc gagttacatg atccccccatg ttgtgcaaaa aagcggttag ctccttcggt    6720
cctccgatcg ttgtcagaag taagttggcc gcagtgttat cactcatggt tatggcagca    6780
ctgcataatt ctcttactgt catgccatcc gtaagatgct tttctgtgac tggtgagtac    6840
tcaaccaagt cattctgaga atagtgtatg cggcgaccga gttgctcttg cccggcgtca    6900
```

```
acacgggata ataccgcgcc acatagcaga actttaaaag tgctcatcat tggaaaacgt    6960
tcttcgggc  gaaaactctc aaggatctta ccgctgttga gatccagttc gatgtaaccc    7020
actcgtgcac ccaactgatc ttcagcatct tttactttca ccagcgtttc tgggtgagca    7080
aaaacaggaa ggcaaaatgc cgcaaaaaag ggaataaggg cgacacggaa atgttgaata    7140
ctcatactct tcctttttca atattattga agcatttatc agggttattg tctcatgagc    7200
ggatacatat ttgaatgtat ttagaaaaat aaacaaatag gggttccgcg cacatttccc    7260
cgaaaagtgc cacctgacgt ctaagaaacc attattatca tgacattaac ctataaaaat    7320
aggcgtatca cgaggccctt tcgtcttcaa gaattccacg gactatagac tatactagta    7380
tactccgtct actgtacgat acacttccgc tcaggtcctt gtcctttaac gaggccttac    7440
cactcttttg ttactctatt gatccagctc agcaaaggca gtgtgatcta agattctatc    7500
ttcgcgatgt agtaaaacta gctagaccga gaaagagact agaaatgcaa aaggcacttc    7560
tacaatggct gccatcatta ttatccgatg tgacgctgca gaagcagaaa tacacgcggt    7620
cagtgaagct attccgctat tgaataacct cagtcacctt gtgcaagaac ttaacaagaa    7680
accaattatt aaaggcttac ttactgatag tagatcaacg atcagtataa ttaagtctac    7740
aaatgaagag aaatttagaa acagattttt tggcacaaag gcaatgagac ttagagatga    7800
agtatcaggt aataatttat acgtatacta catcgagacc aagaagaaca ttgctgatgt    7860
gatgacaaaa cctcttccga taaaaacatt taaactatta actaacaaat ggattcatta    7920
gatctattac attatgggtg gtatgttgga ataaaaatca actatcatct actaactagt    7980
atttacgtta ctagtatatt atcatatacg gtgttagaag atgacgcaaa tgatgagaaa    8040
tagtcatcta aattagtgga agctgaaacg caaggattga taatgtaata ggatcaatga    8100
atattaacat ataaaatgat gataataata tttatagaat tgtgtagaat tgcagattcc    8160
cttttatgga ttcctaaatc ctcgaggaga acttctagta tatctacata cctaatatta    8220
ttgccttatt aaaaatggaa tcccaacaat tacatcaaaa tccacattct cttcaaaatc    8280
aattgtcctg tacttccttg ttcatgtgtg ttcaaaaacg ttatatttat aggataatta    8340
tactctattt ctcaacaagt aattggttgt ttggccgagc ggtctaaggc gcctgattca    8400
agaaatatct tgaccgcagt taactgtggg aatactcagg tatcgtaaga tgcaagagtt    8460
cgaatctctt agcaaccatt attttttttcc tcaacataac gagaacacac agggcgcta    8520
tcgcacagaa tcaaattcga tgactggaaa tttttttgtta atttcagagg tcgcctgacg    8580
catataccct tttcaactga aaaattggga gaaaaggaa aggtgagagc cgcggaaccg    8640
gcttttcata tagaatagag aagcgttcat gactaaatgc ttgcatcaca atacttgaag    8700
ttgacaatat tatttaagga cctattgttt tttccaatag gtggttagca atcgtcttac    8760
tttctaactt ttcttacctt ttacatttca gcaatatata tatatatatt tcaaggatat    8820
accattctaa tgtctgcccc taagaagatc gtcgttttgc caggtgacca cgttggtcaa    8880
gaaatcacag ccgaagccat taaggttctt aaagctattt ctgatgttcg ttccaatgtc    8940
aagttcgatt tcgaaaatca tttaattggt ggtgctgcta tcgatgctac aggtgtccca    9000
cttccagatg aggcgctgga agcctccaag aaggttgatg ccgttttgtt aggtgctgtg    9060
ggtggtccta atgggtac   cggtagtgtt agacctgaac aaggtttact aaaaatccgt    9120
aaagaacttc aattgtacgc caacttaaga ccatgtaact ttgcatccga ctctctttta    9180
gacttatctc caatcaagcc acaatttgct aaggtactg  acttcgttgt tgtcagagaa    9240
ttagtgggag gtatttactt tggtaagaga aaggaagacg atggtgatgg tgtcgcttgg    9300
```

-continued

```
gatagtgaac aatacaccgt tccagaagtg caaagaatca caagaatggc cgctttcatg    9360
gccctacaac atgagccacc attgcctatt tggtccttgg ataaagctaa tgttttggcc    9420
tcttcaagat tatggagaaa aactgtggag gaaaccatca agaacgaatt ccctacattg    9480
aaggttcaac atcaattgat tgattctgcc gccatgatcc tagttaagaa cccaacccac    9540
ctaaatggta ttataatcac cagcaacatg tttggtgata tcatctccga tgaagcctcc    9600
gttatcccag gttccttggg tttgttgcca tctgcgtcct tggcctcttt gccagacaag    9660
aacaccgcat ttggtttgta cgaaccatgc cacggttctg ctccagattt gccaaagaat    9720
aaggtcaacc ctatcgccac tatcttgtct gctgcaatga tgttgaaatt gtcattgaac    9780
ttgcctgaag aaggtaaggc cattgaagat gcagttaaaa aggttttgga tgcaggtatc    9840
agaactggtg atttaggtgg ttccaacagt accacggaag tcggtgatgc tgtcgccgaa    9900
gaagttaaga aaatccttgc ttaaaaagat tctctttttt tatgatattt gtacataaac    9960
tttataaatg aaattcataa tagaaacgac acgaaattac aaaatggaat atgttcatag   10020
ggtagacgaa actatatacg caatctacat acatttatca agaaggagaa aaaggaggat   10080
gtaaaggaat acaggtaagc aaattgatac taatggctca acgtgataag gaaaagaat    10140 tgcactttaa cattaatatt gacaaggagg agggcaccac acaaaaagtt aggtgtaaca   10200
gaaaatcatg aaactatgat tcctaattta tatattggag gattttctct aaaaaaaaa    10260 aaatacaaca aataaaaaac actcaatgac ctgaccattt gatggagttt aagtcaatac   10320
cttcttgaac catttcccat aatggtgaaa gttccctcaa gaattttact ctgtcagaaa   10380
cggccttaac gacgtagtcg acctcctctt cagtactaaa tctaccaata ccaaatctga   10440
tggaagaatg ggctaatgca tcatccttac ccagcgcatg taaaacataa gaaggttcta   10500
gggaagcaga tgtacaggct gaacccgagg ataatgcgat atcccttagt gccatcaata   10560
aagattctcc ttccacgtag gcgaaagaaa cgttaacaca ccctggataa cgatgatctg   10620
gagatccgtt caacgtggta tgttcagcgg ataatagacc tttgactaat ttatcggata   10680
gtcttttgat gtgagcttgg tcgttgtcaa attctttctt catcaatctc gcagcttcac   10740
caaatcccgc taccaatggg ggggccaaag taccagatct caatcctctc tcttggccac   10800
caccggatag taaggttcct aatctaactc ttggtctcct tcttacatag atggcaccta   10860 ttcccttttgg accgtaaatc ttgtgagaag aaattgatag taaatcaatg ttcatttcat   10920
tgacatcaat gtgaatctta ccataggctt gtgcggcgtc agtatgaaag tagatcttat   10980
tctttctaca aattgcacca atttctttaa taggttgaat gacaccgatt tcattattga   11040
cagccatcac agagacgaga caggtatctg gtctaatggc atcttccaat tccttcaaat   11100
cgataagacc ttgatcgtcc acatttagga aagtgacttc aaatccctcc ttcatcatgg   11160
cccgtgcggc ttccaagaca cacttgtgtt ccgttctagt ggtgatgatg tgttcttag    11220 tcttcttata aaatcttggg acacccttaa gaaccatatt attagattcg gtcgctcccg   11280
aagtgaatat tatttccttg gggtcggcat tgatcatctt tgctacgtaa gctctagcat   11340
tttccacagc agtatttgtt tcccaaccgt aagagtgagt gttggaatga ggattaccat   11400
aaagtcccgt ataaaacttc aacatcgtat ccaaaaccct agggtctgtt ggtgtagtgg   11460
cttgcatgtc aagatatatg ggacgagtac caaaacctgt gttttcttga taagcatggc   11520
tcattgcagt gctaccagaa gctactacag catctgggt ggtaccggat gcactcgcac   11580
gggcactagc ctgtgccttt gcagcagcct gaatatcggt atgcgtttcc agagagaagt   11640
```

-continued

```
tgtcgtctaa cttcacgcct gctgcagtct caatgatatt cgaatacgct tgaggagat    11700
acagcctaat atccgacaaa ctgttttaca gatttacgat cgtacttgtt acccatcatt   11760
gaattttgaa catccgaacc tgggagtttt ccctgaaaca gatagtatat ttgaacctgt   11820
ataataatat atagtctagc gctttacgga agacaatgta tgtatttcgg ttcctggaga   11880
aactattgca tctattgcat aggtaatctt gcacgtcgca tccccggttc attttctgcg   11940
tttccatctt gcacttcaat agcatatctt tgttaacgaa gcatctgtgc ttcattttgt   12000
agaacaaaaa tgcaacgcga gagcgctaat ttttcaaaca agaatctga gctgcatttt   12060
tacagaacag aaatgcaacg cgaaagcgct atttttaccaa cgaagaatct gtgcttcatt   12120
tttgtaaaac aaaaatgcaa cgcgagagcg ctaattttc aaacaaagaa tctgagctgc    12180
attttttacag aacagaaatg caacgcgaga gcgctatttt accaacaaag aatctatact  12240
tcttttttgt tctacaaaaa tgcatcccga gagcgctatt tttctaacaa agcatcttag   12300
attacttttt ttctcctttg tgcgctctat aatgcagtct cttgataact ttttgcactg   12360
taggtccgtt aaggttagaa aaggctact ttggtgtcta ttttctcttc cataaaaaaa    12420
gcctgactcc acttcccgcg tttactgatt actagcgaag ctgcgggtgc attttttcaa   12480
gataaaggca tccccgatta tattctatac cgatgtggat tgcgcatact ttgtgaacag   12540
aaagtgatag cgttgatgat tcttcattgg tcagaaaatt atgaacggtt tcttctattt   12600
tgtctctata tactacgtat aggaaatgtt tacattttcg tattgttttc gattcactct   12660
atgaatagtt cttactacaa ttttttttgtc taaagagtaa tactagagat aaacataaaa   12720
aatgtagagg tcgagtttag atgcaagttc aaggagcgaa aggtggatgg gtaggttata   12780
tagggatata gcacagagat atatagcaaa gagatacttt tgagcaatgt tgtgggaagc   12840
ggtattcgca atattttagt agctcgttac agtccggtgc gttttttggtt ttttgaaagt   12900
gcgtcttcag agcgcttttg gttttcaaaa gcgctctgaa gttcctatac tttctagaga   12960
ataggaactt cggaatagga acttcaaagc gtttccgaaa acgagcgctt ccgaaaatgc   13020
aacgcgagct gcgcacatac agctcactgt tcacgtcgca cctatatctg cgtgttgcct   13080
gtatatatat atacatgaga agaacggcat agtgcgtgtt tatgcttaaa tgcgtactta   13140
tatgcgtcta tttatgtagg atgaaaggta gtctagtacc tcctgtgata ttatcccatt   13200
ccatgcgggg tatcgtatgc ttccttcagc actaccctt agctgttcta tatgctgcca   13260
ctcctcaatt ggattagtct catccttcaa tgctatcatt tcctttgata ttcgatccta   13320
ggcatagtac cgagaaacta gtgcgaagta gtgatcaggt attgctgtta tctgatgagt   13380
atacgttgtc ctggccacgg cagaagcacg cttatcgctc caatttccca caacattagt   13440
caactccgtt aggcccttca ttgaaagaaa tgaggtcatc aaatgtcttc caatgtgaga   13500
ttttgggcca ttttttatag caaagattga ataaggcgca ttttttcttca aagctttatt   13560
gtacgatctg actaagttat cttttaataa ttggtattcc tgtttattgc ttgaagaatt   13620
gccggtccta tttactcgtt ttaggactgg ttca                                13654
```

<210> SEQ ID NO 29
<211> LENGTH: 600
<212> TYPE: DNA
<213> ORGANISM: Saccharomyces cerevisiae

<400> SEQUENCE: 29

```
agaaccaaat gggaaaatcg gaatgggtcc agaactgctt tgagtgctgg ctattggcgt     60
ctgatttccg ttttgggaat cctttgccgc gcgcccctct caaaactccg cacaagtccc    120
```

-continued

```
agaaagcggg aaagaaataa aacgccacca aaaaaaaaaa aataaaagcc aatcctcgaa      180
gcgtgggtgg taggccctgg attatcccgt acaagtattt ctcaggagta aaaaaaccgt      240
ttgttttgga attccccatt tcgcggccac ctacgccgct atctttgcaa caactatctg      300
cgataactca gcaaattttg catattcgtg ttgcagtatt gcgataatgg gagtcttact      360
tccaacataa cggcagaaag aaatgtgaga aaattttgca tcctttgcct ccgttcaagt      420
atataaagtc ggcatgcttg ataatctttc tttccatcct acattgttct aattattctt      480
attctccttt attctttcct aacataccaa gaaattaatc ttctgtcatt cgcttaaaca      540
ctatatcaat aatgcaattt tctactgtcg cttctatcgc cgctgtcgcc gctgtcgctt      600

<210> SEQ ID NO 30
<211> LENGTH: 850
<212> TYPE: DNA
<213> ORGANISM: Saccharomyces cerevisiae

<400> SEQUENCE: 30
gccacgggtc aacccgattg ggatcacccc actggggccc aagcctgata tccgacctcc       60
atgaaatttt ttttttctt tcgattagca cgcacacaca tcacatagac tgcgtcataa      120
aaatacacta cggaaaaacc ataaagagca aagcgatacc tacttggaag gaaaggagc      180 acgcttgtaa gggggatggg ggctaagaag tcattcactt tcttttccct tcgcggtccg      240
gacccgggac ccctcctctc cccgcacgat ttcttccttt catatcttcc ttttattcct      300
atcccgttga agcaaccgca ctatgactaa atggtgctgg acatctccat ggctgtgact      360
tgtgtgtatc tcacagtggt aacggcaccg tggctcggaa acggttcctt cgtgacaatt      420
ctagaacagg ggctacagtc tcgataatag aataataagc gcattttgc tagcgccgcc      480 gcggcgcccg tttcccaata gggaggcgca gtttatcggc ggagctctac ttcttcctat      540
ttgggtaagc ccctttctgt tttcggccag tggttgctgc aggctgcgcc ggagaacata      600
gtgataaggg atgtaacttt cgatgagaga attagcaagc ggaaaaaaac tatggctagc      660
tgggagttgt ttttcaatca tataaaaggg agaaattgtt gctcactatg tgacagtttc      720
tgggacgtct taacttttat tgcagaggac tatcaaatca tacagatatt gtcaaaaaaa      780
aaaaagacta ataataaaaa atgaagttat ctcaagttgt tgtttccgcc gtcgccttca      840
ctggtttagt                                                            850

<210> SEQ ID NO 31
<211> LENGTH: 600
<212> TYPE: DNA
<213> ORGANISM: Saccharomyces cerevisiae

<400> SEQUENCE: 31
aaagaatcca tcactatttg aaaaaaagtc atctggcacg tttaattatc agagcagaaa       60
tgatgaaggg tgttagcgcc gtccactgat gtgcctggta gtcatgattt acgtataact      120
aacacatcat gaggacggcg gcgtcacccc aacgcaaaag agtgacttcc ctgcgctttg      180
ccaaaacccc atacatcgcc atctggctcc tggcagggcg gttgatggac atcagccgcc      240
tcccttaatt gctaaagcct ccacaaggca caattaagca atatttcggg aaagtacacc      300
agtcagtttg cgcttttatg actgggttct aaggtactag atgtgaagta gtggtgacag      360
aatcagggag ataagaggga gcaggtgggg gtaatgatgt gcgataacaa tcttgcttgg      420
ctaatcaccc ccatatcttg tagtgagtat ataaatagga gcctcccttc ctattgcaac      480
```

-continued

```
tccataaaat ttttttttgt agccacttct gtaacaagat aaataaaacc aactaatcga    540
gatatcaaat atgggtagtt tttgggacgc attcgcagta tacgacaaga aaaagcacgc    600
```

<210> SEQ ID NO 32
<211> LENGTH: 600
<212> TYPE: DNA
<213> ORGANISM: Saccharomyces cerevisiae

<400> SEQUENCE: 32

```
ttcaggagtc tctcgcgtta gagcagtacg tggcgcagct aaactcgccg ggaggtctgc     60
ttcacgagcg cggtgtgcgc ctagtattgc cccgacggtc cgggtgccta tccctagatt    120
tcgtcgtgcc ccgacccaaa tagttaaacg tgtggtttat gggtgcacca gggctttatc    180
gtgttttata tcgatggcga tttgtgcctc cagtgtattt ttgtatatcc aattaaggtt    240
tcttacctaa ttttattttt atcatcttta gttaatgctg gtttgctctg tttctgctgc    300
tttctgtgcg gttctcctct tctcttgttt cttcgtgttg tccccatcg ccgatgggct     360
tatatggcgt atatatatag agcgagtttt tacgtcgaag atcatctcag tttgcttgat    420
agcctttcta ctttattact ttcgttttta acctcattat actttagttt tctttgatcg    480
gttttttct ctgtatactt aaaagttcaa atcaaagaaa catacaaaac tacgtttata    540
tcaattaata atgtctgaaa ttcaaaacaa agctgaaact gccgcccaag atgtccaaca    600
```

COMPOSITIONS AND METHODS USING THE YEAST YMR107W PROMOTER

This application is a continuation of application Ser. No. 11/239,107, filed Sep. 30, 2005, now U.S. Pat. No. 7,067,282 which is a continuation of application No. Ser. 10/776,213, filed Feb. 12, 2004, now U.S. Pat. No. 7,078,190 which is a continuation of application Ser. No. 09/743,194, filed Jan. 8, 2001, now U.S. Pat. No. 6,716,601 the entire content of which is hereby incorporated by reference in this application.

BACKGROUND OF THE INVENTION

The controlled production in yeast of an enormous variety of useful proteins or polypeptides can be achieved using recombinant DNA technology. Yeast cells can be transformed with yeast expression vectors, which contain homologous or heterologous nucleic acid molecules encoding polypeptides (coding sequences). The yeast cells can then produce large quantities of the useful proteins or polypeptides in yeast cell culture.

Expression of the nucleic acid molecule encoding a polypeptide by the yeast expression vector is initiated at a region known as the promoter, which is recognized by and bound by RNA polymerase. The RNA polymerase travels along the DNA, transcribing the information contained in the coding strand from its 5' to 3' end into messenger RNA, which is in turn translated into a polypeptide having the amino acid sequence for which the DNA codes. The present invention provides novel yeast promoters useful for, inter alia, controlling the expression of homologous and heterologous nucleic acid sequences encoding proteins and polypeptides in yeast cells.

SUMMARY OF THE INVENTION

It is an object of the invention to provide novel yeast promoters, yeast expression vectors, and transformed yeast cells. It is a further object of the invention to provide a method for producing proteins and polypeptides in yeast cell culture.

In one embodiment of the invention a yeast promoter which comprises at least 17 contiguous nucleotides of an isolated and purified polynucleotide is provided. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

As used herein, the term "promoter" refers to a nucleic acid sequence which is cable of initiating transcription of a nucleic acid molecule encoding a polypeptide (coding sequence); a "yeast promoter" is capable of initiating transcript of a coding sequence in yeast cells; and "promoter activity" refers to the level or amount of transcription initiation of a coding sequence, and encompasses any level above background (i.e., the level or amount that occurs in the absence of a promoter; a background level, which is normally zero).

Another embodiment of the invention provides a yeast promoter which comprises an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

Yet another embodiment of the invention provides a yeast promoter fragment which comprises at least 17 contiguous nucleotides of a polynucleotide. The polynucleotides are shown in SEQ ID NO:1, SEQ ID NO:2, SEQ ID NO:3, and SEQ ID NO:4. The fragment has promoter activity as determined by cloning the fragment into a yeast expression vector, wherein the fragment is operably linked to a reporter gene, transforming yeast cells with the yeast expression vector, growing the yeast cells in yeast cell culture under conditions favorable for expression of the reporter gene, and assaying the yeast culture for a reporter protein expressed by the reporter gene. The expression of the reporter gene indicates the fragment has promoter activity.

Still another embodiment of the invention provides a yeast expression vector comprising a yeast promoter. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

A further embodiment of the invention provides a yeast expression vector where activity of the promoter is controlled by varying the level of a non-fermentable carbon source, such as ethanol, in a medium of yeast cells in culture. The yeast cells are transformed with said yeast expression vector.

In yet another embodiment of the invention, a yeast expression vector comprising a yeast promoter which comprises at least 17 contiguous nucleotides of an isolated and purified polynucleotide is provided. The promoter sequences are shown in SEQ ID NO:1, SEQ ID NO:2, and SEQ ID NO:4. Promoter activity is controlled by varying the level of a fermentable carbon source in a medium of yeast cells in culture, where the yeast cells are transformed with the yeast expression vector. The fermentable carbon source can be glucose.

Another embodiment of the invention provides a yeast expression vector comprising a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. Promoter activity is controlled by varying the level of a fermentable carbon source and a non-fermentable carbon source, such as ethanol, in a medium of yeast cells in culture, where the yeast cells are transformed with the yeast expression vector. The fermentable carbon source can be glucose. The non-fermentable carbon source can be ethanol.

Still another embodiment of the invention provides a yeast cell transformed with a yeast expression vector. The yeast expression vector comprises a yeast promoter. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

Yet another embodiment of the invention provides a method for producing a polypeptide. A yeast expression vector is constructed where a polynucleotide encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule encoding a polypeptide. A culture of yeast cells is transformed with the yeast expression vector. The yeast cells are maintained in culture so that the polypeptide is expressed. The polypeptide is then recovered.

Still another embodiment of the invention provides a method for producing a polypeptide. A nucleic acid molecule encoding the polypeptide is cloned into an expression vector selected from the group consisting of pYLR110P+ luc, pYMR251AP+luc, pYMR107P+luc, pZEO1P+luc, pYLR110P, pYMR251AP, pYMR107P, and pZEO1P. The nucleotide acid molecule is operably linked to a promoter of the expression vector. A culture of yeast cells is transformed with the yeast expression vector. The yeast cells are maintained in culture so that the polypeptide is expressed and the polypeptide is then recovered.

Another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. Yeast cells are transformed with the yeast expression vector and are maintained in culture medium. The expression of the nucleic acid molecule encoding the polypeptide is controlled by varying the level of a fermentable carbon source, such as glucose, in the culture medium. The polypeptide is then recovered.

Still another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule. A culture of yeast cells is transformed with the yeast expression vector. The yeast cells are maintained in culture medium and the expression of the nucleic acid molecule encoding the polypeptide is controlled by varying the level of a non-fermentable carbons source, such as ethanol, in the culture medium. The polypeptide is then recovered.

Another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. A culture of yeast cells is transformed with the yeast expression vector. The yeast cells are maintained in culture medium and the expression of the nucleic acid encoding the polypeptide is controlled by varying the level of a fermentable carbon source, such as glucose, and a non-fermentable carbon source, such as ethanol, in the culture medium. The polypeptide is then recovered.

Yet another embodiment of the invention provides a method of identifying a promoter fragment with promoter activity by generating a fragment comprising at least 17 contiguous nucleotides of an isolated and purified polynucleotide. The polynucleotides are shown in SEQ ID NO:1, SEQ ID NO:2, SEQ ID NO:3, and SEQ ID NO:4. The fragment is cloned into a yeast expression vector, so that the fragment is operably linked to a reporter gene. Yeast cells are transformed with the yeast expression vector and grown in yeast cell culture under conditions favorable for expression of the reporter gene. The yeast culture is assayed for a reporter protein expressed by the reporter gene. Expression of the reporter gene indicates the fragment has promoter activity.

BRIEF DESCRIPTION OF THE DRAWINGS

FIG. 13 schematically illustrates the YLR110C promoter region.
FIG. 14 schematically illustrates the YMR251WA promoter region.
FIG. 15 schematically illustrates the YMR107W promoter region.
FIG. 16 schematically illustrates the ZEO1 promoter region.

DETAILED DESCRIPTION OF THE INVENTION

Figure 1:
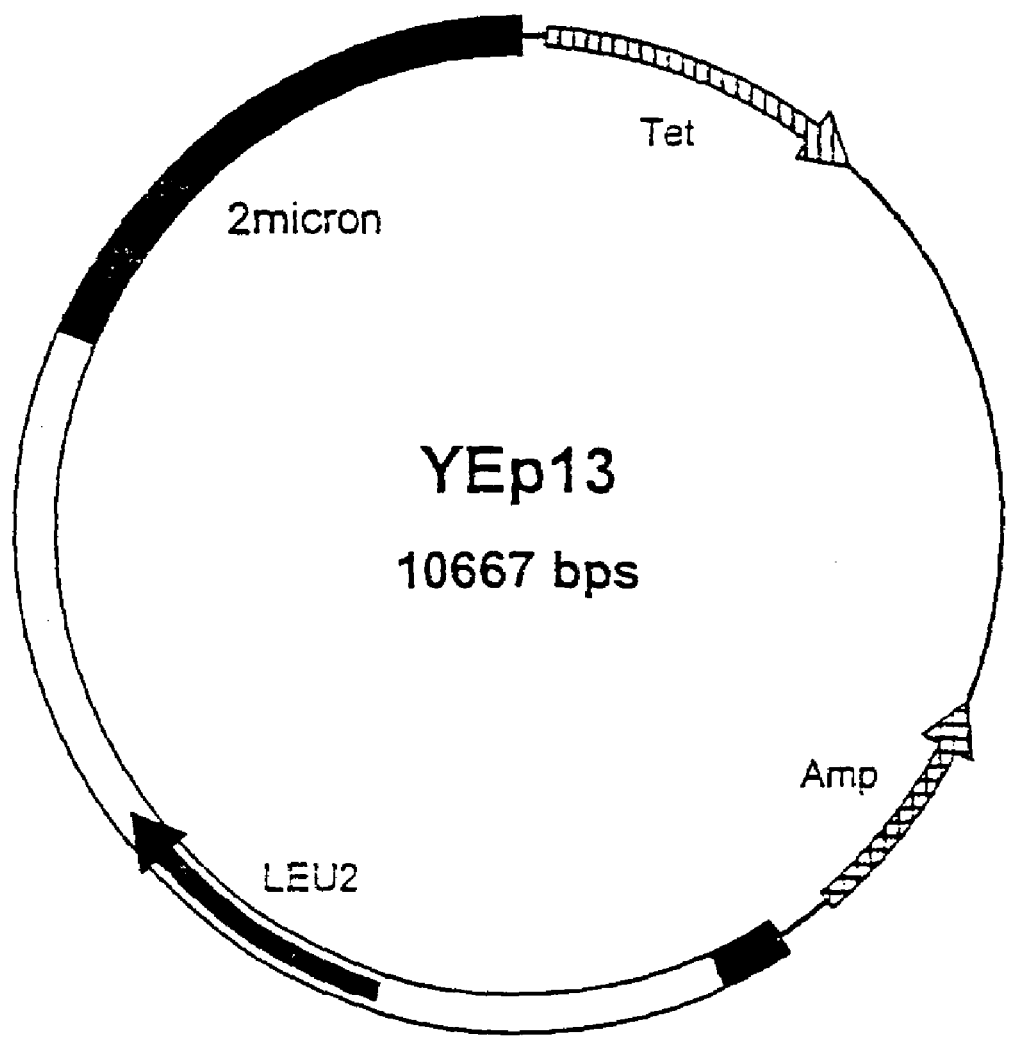
FIG. 1 is a map of YEp13 expression vector.

Novel yeast promoters whose activity can be controlled by a fermentable carbon source, such as glucose, or a non-fermentable carbon source, such as ethanol, or both have been identified. The yeast promoters are useful for, inter alia, the high level production of proteins or polypeptides in yeast cell culture.

Yeast Promoters

The isolated and purified promoter polynucleotides of the invention are shown in SEQ ID NO:1 (the YLR110C promoter), SEQ ID NO:2 (the YMR251WA promoter), SEQ ID NO:3 (the YMR107W promoter), and SEQ ID NO:4 (the ZEO1 promoter). Yeast promoters comprising as little as 17 nucleic acids have been determined to function as promoters. The yeast promoters of the invention comprise at least 17, 25, 50, 75, 100, 150, 200, 250, 300, 350, 400, 450, 500, 600 or 700 contiguous nucleic acids of an isolated and purified polynucleotide up to the maximum length provided in any one of the sequences presented herein, that is, SEQ ID NO:1, SEQ ID NO:2, SEQ ID NO:3, and SEQ ID NO:4.

Preferably, the promoter polynucleotides are isolated free of other components, such as proteins and lipids. The polynucleotides can be made by cell and isolated or can be synthesized in the laboratory, for example, using an automatic synthesizer or an amplification method such as PCR.

Naturally occurring variants and artificial sequence variants (that is, those which do not occur in nature) of the promoters are included in the invention. Variants of the promoters and/or fragments thereof have, along their entire length, sequence identity of at least 90%, and preferably greater than 95% as determined by the Smith-Waterman homology search algorithm as implemented in MPsrch™ program (University of Edinburgh) using an affine gap search with the following search parameters: gap open penalty: 12, gap extension penalty: 1.

Fragments of the full-length promoters are also functional as promoters. A promoter fragment of at least 17 contiguous nucleotides may occur at any position along the full-length promoter as shown in SEQ ID NO:1, SEQ ID NO:2, SEQ ID NO:3 or SEQ ID NO:4. Accordingly, promoter activity of 17 or more continuous nucleotides occurring anywhere along the full-length promoter can be analyzed. Fragments of 17, 25, 50, 75, 100, 150, 200, 250, 300, 350, 400, 450, 500, 550, 600, 650 or 700, nucleotides of the promoters may be constructed by, for example, subjecting an isolated promoter to restriction endonucleases, to 5'- or 3'-deletion mutagenesis, to PCR, or to site specific deletion. A combination of these methods can also be used to generate fragments of a promoter.

The invention further embodies a hybrid promoter, i.e., a promoter that comprises more than one promoter or more than one fragment of a promoter from which it was derived. The promoter fragments can be derived from more than one of the promoter sequences shown in SEQ ID NO:1, SEQ ID NO:2, SEQ ID NO:3 and SEQ ID NO:4. The promoters and fragments can be constructed as described above, ligated together, and cloned into a yeast expression vector. Where a promoter comprises nucleotides from at least two polynucleotides selected from the group consisting of SEQ ID NO:1, SEQ ID NO:2, SEQ ID NO:3 and SEQ ID NO:4, at least 5, 6, 7, 8, 9, 10, 25, 50, 75, 100, 150, 200, 250, 300, 350, 400, 450, 500, 550, 600, or 650 contiguous nucleotides are derived from each of the polynucleotides to form a promoter of at least 17 nucleotides. Alternatively, each of the full-length promoters can be combined with another full-length promoter or with fragments of another promoter.

The yeast promoters, fragments of the promoters, and hybrid promoters are useful for controlling expression of a protein or polypeptide when the yeast promoter is operably linked to a nucleic acid molecule encoding the protein or polypeptide.

Determination of Promoter Activity

Promoters and fragments of promoters can be assayed for promoter activity by cloning a fragment of a promoter, or a full-length promoter, or a hybrid promoter into a yeast expression vector so that is operably linked to a reporter gene, i.e., a coding sequence for a reporter protein. The yeast expression vector is transformed in yeast cells, which are grown in yeast cell culture under conditions favorable for expression of the reporter gene, for example, under conditions providing a fermentable and/or non-fermentable carbon source. Expression of the reporter gene, as determined by an assay for the amount of a reporter protein expressed by the reporter gene, indicates that the promoter has activity.

For example, to determine if a promoter has activity, i.e. is operative, expression of a reporter gene by a promoter of the invention may be compared to expression of the reporter gene by a reference promoter such as PBR1 (Cottingham et al. (1991) Eur J Biochem 196(2):431-8; Sleep et al. (1991) Biotechnology 9(2):183-7; Finnis et al. (1992) Yeast 8(1): 57-60; Meldgaard et al. (1995) Glycoconj J 12(3):380-90; Bach et al. (1996) Receptors and Channels 4(2):129-39. A promoter, a fragment of a promoter, or a hybrid promoter of the invention is operative if it expresses at least 25% of the amount of a reporter protein as the full-length PBR1 promoter in a medium containing a non-fermentable carbon source, or a fermentable carbon source, or both. Preferably, an operative promoter expresses at least 50%, 75%, 100%, 200%, 300%, 400%, or more of the amount of a reporter protein as the full-length PBR1 reference promoter.

Assays for promoter activity are useful for identifying yeast promoters with high activity and the specific nucleotide sequences of the promoters that are necessary for promoter activity.

Yeast Expression Vectors

The yeast promoters of the invention, which comprise isolated and purified polynucleotides selected from the group consisting of SEQ ID NO:1, SEQ ID NO:2, SEQ ID NO:3, and SEQ ID NO:4 or fragments thereof, can be used to construct yeast expression vectors.

Yeast expression vectors are any vectors capable of autonomous replication within a yeast host organism or capable of integrating into the yeast genome. Yeast expression vectors are useful for introducing foreign DNA into yeast cells. Typical yeast expression vectors include yeast integrative plasmids (YIp), yeast replicating plasmids (YRp), yeast expression plasmids (YXp), yeast centromere-containing plasmids (YCp), and yeast episomal plasmids (YEp). Preferably, a yeast expression vector can be selected and maintained in both yeast and E. coli.

Yeast expression vectors, typically plasmids, incorporate the yeast promoters of the invention to control expression of nucleic acid molecules encoding heterologous or homologous proteins or polypeptides. The nucleic acid molecules are operably linked to a promoter in the yeast expression vector. A wide range of heterologous eukaryotic and prokaryotic proteins or peptides may be expressed by the vectors of the invention.

Expression vectors incorporating the promoters can be constructed by inserting into a vector a nucleic acid molecule encoding a protein or polypeptide (coding sequence) which is to be expressed. The coding sequence can be inserted at a restriction site which is provided downstream of a translation start codon controlled by the promoter. The coding sequence must be inserted in the correct translational reading frame.

Alternatively, the polynucleotide can itself be provided with a translational start codon followed directly by a coding sequence. Where the promoter does not contain a translational start codon, a restriction site is provided so that the coding sequence can be inserted in the correct reading fame and so that its translational start codon is correctly positioned in relation to the promoter. The coding sequence can encode heterologous or homologous or eukaryotic or prokaryotic polypeptides or proteins. In a preferred embodiment the coding sequence encodes a fusion protein. The coding sequence may further comprise a signal sequence.

In addition to the promoters of the invention, other components can be added to the expression vectors of the invention. For example, yeast selective markers, such as LEU2 or TRP1, which allow for selection of yeast cells that have been effectively transformed by the vector can be added. A yeast replication origin, such as the replication origin of the 2-micron plasmid or the autonomous ARS replication segment can be added. Upstream activating sequences and transcription terminator sequences may be added. Further, at least a portion of a bacterial plasmid, such as found in YEp13, can be added to enable the yeast expression vector to be manipulated in an intermediate bacterial host system, such as *Escherichia coli*.

The expression vector may also comprise a reporter gene which encodes, for example, β-galactosidase or luciferase. The reporter gene can be under the control of a promoter of the invention. Where the reporter gene, i.e., coding sequence, is linked to a gene encoding a desired protein, assaying the level of expression of the reporter protein can quickly and easily determine the level of expression of the desired protein.

The expression vectors of the invention can be used to direct the fermentable carbon source and/or non-fermentable carbon source-induced high level expression of proteins or polypeptides in yeast. The promoters of the invention can be induced by the presence of a fermentable carbon source, such as glucose, or a non-fermentable carbon source, such as ethanol, or both. That is, the promoters have greater promoter activity in the presence of a fermentable carbon source, or a non-fermentable carbon source, or both than in the absence of a fermentable carbon source, or a non-fermentable carbon source, or both. Promoters YLR110C, as shown in SEQ ID NO:1; YMR251WA, as shown in SEQ ID NO:2; and ZEO1, as shown in SEQ ID NO:4, can be induced by a fermentable carbon source, such as glucose, or by a non-fermentable carbon source, such as ethanol, or by both. Promoter YMR107W, as shown in SEQ D NO:3, can be induced by a non-fermentable carbon source, such as ethanol. Thus, the amount of expression of a homologous or heterologous nucleic acid molecule encoding a protein operably linked to the promoters of the invention can be controlled by varying the amount of an available fermentable carbon source, such as glucose, or a non-fermentable carbon source, such as ethanol, or both.

Transformed Yeast Cells

Yeast cells can be transformed with the yeast expression vectors of the invention. Transformation can be accomplished by well known methods, including, but not limited to electroporation, calcium phosphate precipitation, and microinjection. The yeast expression vectors of the invention can be used to transform yeast cells, including, but not limited to Saccharomyces cerevisiae, S. uvarum, S. carlsbergensis, Saccharomycopsis lipolytica, Schizosaccharomyces pombe, and Kluyveromyces lactis.

Transformed yeast cells containing a yeast expression vector can be grown in an appropriate medium for the yeast. A fermentable or non-fermentable carbon source can be added to the yeast culture medium in order to control the activity of the promoter.

Methods of Production of Proteins

Yeast cells transformed with expression vectors comprising a promoter of the invention can be used to produce proteins and polypeptides. Under proper cell culture conditions, preferably in the presence of a fermentable or non-fermentable carbon source, or both, the promoters of the invention will control expression of a nucleic acid molecule encoding a polypeptide operably linked to the promoter.

The protein or polypeptide can be retained within the yeast cell. The yeast cells can be then harvested, lysed, and the protein obtained and substantially purified in accordance with conventional techniques. Such techniques include, but are not limited to chromatography, electrophoresis, extraction, and density gradient centrifugation.

In a preferred embodiment of the invention, the protein or polypeptide to be recovered will further comprise a signal peptide capable of transporting the protein or polypeptide through the membrane of a transformed yeast cell. The protein or polypeptide can be recovered from the culture medium by, for example, adsorption or precipitation.

Further, the proteins and polypeptides may be produced as a fusion protein, which includes not only the amino acid sequence of the desired protein, but also one or more additional proteins. Affinity purification protocols can be used to facilitate the isolation of fusion proteins. Typically, a ligand capable of binding with high specificity to an affinity matrix is chosen as the fusion partner for the desired protein. For example, fusion proteins made with glutathione-S-transferase can be selectively recovered on glutathione-agarose and IgG-Sepharose can be used to affinity purify fusion proteins containing staphylococcal protein A.

Preferably, the protein or polypeptide of interest can be separated from the remainder of the fusion protein. The fusion protein can be constructed so that a site for proteolytic or chemical cleavage is inserted between the protein of interest and the fusion partner. For example, sites for cleavage by collagenase, Factor Xa protease, thrombin, and enterokinase, have been inserted between the fusion partner and the protein of interest. The protein of interest can be also cleaved from the remainder of the fusion protein by chemical cleavage by, for example, hydroxylamine, cyanogen bromide (CNBr), or N-chlorosuccinamide.

The following are provided for exemplification purposes only and are not intended to limit the scope of the invention described in broad terms above. All references cited in this disclosure are incorporated by reference.

EXAMPLE 1

Preparation of Yeast Samples

S. cerevisiae Strain 11C

This example describes the growth of haploid Saccharomyces cerevisiae strain 11C. It has the genotype: ade2-161, trp1-$\Delta$63, ura3-52, lys2-801, leu2$\Delta$1 &/or leu2-3 &/or leu2-112, his3$\Delta$200 &/or his4-519. 11C was generated by crossing the strains YPH500 (Mat a ura3-52 lys2-801 ade2-161 trp1-$\Delta$63 his3$\Delta$200 leu2$\Delta$1) (Sikorski and Hieter. (1989) A system of shuttle vectors and yeast host strains designed for efficient manipulation of DNA in Saccharomyces cerevisiae. Genetics 122: 19-27) and AH22 (MATa leu2-3 leu2-112 his4-519) (Hinnen et al. (1978) Transformation of yeast. Proc. Natl. Acad. Sci. USA 75: 1929-1933).

Three sterile 500 ml conical flasks, each containing 100 ml sterile YPD broth (Sigma, Cat No. Y-1375) were inoculated with sterile 10 μl loops of differing quantities of the S. cerevisiae strain 11C from a freshly streaked YPD plate (Sigma, Cat No. Y-1500), and grown in an orbital shaker at 30° C., 200 rpm, overnight. The growth of 11C in the three flasks was measured by absorbance at 600 nm. One flask was deemed to be at the late exponential growth phase (1.98 ODU ml at 600 nm), and this culture was used to inoculate (50 ml o/n culture per flask) 2 identical 5 L sterile conical flasks (labeled E and L), each containing 1 L sterile YPD broth to a final concentration of ~0.1 ODU ml. Flasks E and L were grown in an orbital shaker at 30° C., 200 rpm. 10 ml samples were collected at times indicated below (Table 1). The samples were treated as follows: their growth was determined (A600 nm), the possibility of contamination was checked (using a light microscope), cells were harvested in a benchtop centrifuge (~2000×g for 5 minutes), and the supernatant removed and frozen at −20° C. (samples labeled E0-E3, and L0-L5).

TABLE 1

Growth of cultures E and L as measure by absorbance at 600 nm.

| Time Point | Time after inoculation (min) | Growth of flask E (ODU) | Growth of flask L (ODU) |
| --- | --- | --- | --- |
| T0 | 0 | 0.099 | 0.099 |
| T1 | 310 | 0.37 | 0.36 |
| T2 | 410 | 0.71 | 0.72 |
| T3 | 455 | 0.97 | 0.92 |
| T4 | 775 | — | 3.64 |
| T5 | 1420 | — | 6.05 |

After 455 minutes, a time deemed to be late exponential growth phase in glucose, flask E (i.e. early) was harvested (~2000×g for 5 minutes), split into 50 ml aliquots, and frozen at −80° C. After 1420 minutes, a time deemed to be growth on ethanol, flask L (i.e. late) was harvested (~2000×g for 5 minutes), split into 50 ml aliquots, and frozen at −80° C.

Determination of Glucose and Ethanol Concentration

Supernatant samples (E0-E3, and L0-L5) were defrosted, and their ethanol and glucose contents were measured using ethanol (Boehringer, Cat. No. 176290) and glucose (Boehringer, Cat. No. 176251) detection kits according to manufacturers instructions. The concentrations determined are shown below in Table 2.

TABLE 2

Glucose and Ethanol concentrations in supernatants of cultures E and L at different time points.

| Sample | Time after inoculation (min) | Glucose level in media (g L$^{-1}$) | Ethanol level in media (g L$^{-1}$) |
| --- | --- | --- | --- |
| E0 | 0 | 20.0 | 0.0 |
| E1 | 310 | 21.8 | 0.3 |
| E2 | 410 | 21.8 | 0.8 |
| E3 | 455 | 21.2 | 0.87 |
| L0 | 0 | 20.0 | 0.0 |
| L1 | 310 | 22.2 | 0.36 |
| L2 | 410 | 22.0 | 0.62 |
| L3 | 455 | 20.0 | 0.87 |
| L4 | 775 | 11.8 | 5.2 |
| L5 | 1420 | 0.0 | 11.8 |

It can seen in Table 2 that at the point of culture harvest for E (E3, 455 minutes), the cells were still utilizing glucose as a carbon source, while at the point of culture harvest for L (L5, 1420 minutes), glucose was exhausted, and the cells were utilizing ethanol as a carbon source. Calibration values used to calculate glucose concentrations are shown in Table 3. Calibration values used to calculate ethanol concentrations are shown in Table 4.

TABLE 3

Glucose standards

| GLUCOSE STANDARDS g/l | OD A340 |
| --- | --- |
| 0 | 0 |
| 0.2 | 0.246 |
| 0.4 | 0.461 |
| 0.6 | 0.726 |
| 0.8 | 0.967 |
| 1 | 1.227 |

TABLE 4

Ethanol standards

| ETHANOL STANDARDS g/L | OD A340 |
| --- | --- |
| 4.72 | 0.041 |
| 9.44 | 0.083 |
| 18.88 | 0.166 |
| 37.76 | 0.322 |
| 56.6 | 0.534 |
| 75.5 | 0.664 |
| 94.4 | 0.846 |

EXAMPLE 2

Analysis of RNA Levels from Yeast Dimorphic Growth Samples

Total RNA Isolation

Total RNA was isolated from 300 ml of culture using the hot phenol protocol. The frozen yeast pellets were resuspended in lysis buffer (4 ml) (0.5 ml Tris-CL (1M, pH 7.5), 1.0 ml EDTA (0.5 M), 2.5 ml 10% SDS, and 46.0 ml ddH$_2$O) and an equal volume of acid phenol was added and vortexed. Following incubation at 65° C. for one hour (with occasional vigorous vortexing) the mixture was placed on ice for 10 minutes then centrifuged (10 minutes). The aqueous layer was transferred to a fresh centrifuge tube and mixed with an equal volume of phenol at room temperature. The mixture was centrifuged and an equal volume of chloroform was mixed with the aqueous layer in a fresh centrifuge tube. Following centrifugation the aqueous layer was transferred to a fresh centrifuge tube and sodium acetate (to a final concentration of 0.3M) and two volumes of 100% ethanol was added to precipitate the RNA. The mixture was placed at −20° C. for 30 minutes then centrifuged for 10 minutes to pellet the RNA. The RNA pellet was washed 2-3 times with 70% ethanol then allowed to dry at room temperature. The pellet was resuspended in ddH2O (200-500 μL). The RNA was quantitated by measuring OD 260-280. Yield of total RNA was ~4.5 mg from each culture.

Poly A+RNA Purification

Poly A+RNA was purified from total RNA using Qiagen Oligotex mRNA Midi Kit (Qiagen, Cat. No. 70042). 2 mg of total RNA was used as starting material and made up to a volume of 500 μl with DEPC treated H$_2$O. To this 500 μl buffer OBB (2× binding buffer) and 55 μl oligotex suspension was added. The "Ologotex mRNA Spin Column Protocol" from the kit protocol booklet was followed. The pelleted mRNA was washed in 200 μl 75% ethanol, dried and resuspended in 10 μl DEPC treated H$_2$O. Yield of Poly A+RNA was ~8 μg for each sample.

cDNA Synthesis cDNA was synthesized using the protocol for GeneChip Expression Analysis Manual using reagents from Gibco BRL Life Technologies Superscript Choice System cat. No. 18090-019. For each sample 5 μg Poly A+RNA was added to 100 pmol of T7-(dT)$_{24}$ primer (sequence: GGCCAGT-GAATTGTAATACGACTCACTATAGGGAGGCGG-(T) 24, HPLC purified) (SEQ ID NO:15) in a total of 8 μl (made up to volume with DEPC treated H$_2$O). The reaction mixture was incubated for 10 minutes at 70° C. in a Perkin Elmer PE9600 thermalcycler then put on ice. The following reagents were added to the reaction mixture: 4 μl 5× first strand cDNA buffer; 2 μl 0.1M DTT; and 1 μl 10 mM dNTP mix. The reaction mixture was mixed and incubated at 37° C. for 2 minutes in a Perkin Elmer PE9600 thermocycler. 5 μl SuperScript II reverse transcriptase was then added. The mixture was incubated at 37° C. for 1 hour in a Perkin Elmer PE9600 thermocycler.

The first strand cDNA reaction was placed on ice and the following reagents added: 91 μl DEPC treated H$_2$O; 30 μl 5× second strand reaction buffer; 3 μl 10 mM dNTP mix; 1 μl 10 units/μl *E. coli* DNA ligase; 4 μl 10 units/μl *E. coli* DNA Polymerase I; and 1 μl 2 units/μl RNase H. The mixture was incubated at 16° C. for 2 hours in a Perkin Elmer PE9600 thermalcycler. 2 μl 5 units/μl T4 DNA Polymerase was then added. The mixture was incubated for a further 5 minutes at 16° C. in a Perkin Elmer PE9600 thermalcycler. 10 μl 0.5M EDTA was then added.

The double stranded DNA was cleaned up by phenol extraction. The reaction product transferred to a 1.5 ml eppendorf tube and 162 μl Tris pH 8.0 saturated phenol was added. The tube was mixed by vortexing, the tube was then centrifuged in a microfuge at 13,000 rpm for 5 minutes. The top fraction was recovered and cDNA precipitated by addition of 60 μl 7.5M ammonium acetate plus 400 μl absolute ethanol. This was immediately centrifuged in a microfuge at 13,000 rpm for 20 minutes. The supernatant fraction was discarded, the pellet was washed in 75% ethanol and then air-dried. The pellet was resuspended in 20 µl DEPC treated H$_2$O Synthesis of Biotin-Labeled cRNA by In Vitro Transcription (IVT)

Reagents from Ambion MEGAscript T7 kit, cat. No. 1334, were used for the synthesis of biotin-labeled cRNA by in vitro transcription (IVT). The NTP Labeling mix comprised 7.5 mM ATP; 7.5 mM GTP; 5.625 mM UTP; 1.875 mM Biotin-16-UTP (Enzo cat No. 42814); 5.625 mM CTP; and 1.875 mM Biotin-11-CTP (Enzo cat No. 42818). The IVT Labeling reaction comprised: 14.5 µl NTP Labeling mix; 2 µl 10× Ambion Transcription Buffer; 1.5 µl Double strand cDNA (from above); and 2 µl Ambion T7 Enzyme Mix.

The reaction mixture was incubated for 6 hours at 37° C. in a Perkin Elmer PE9600 thermalcycler. The biotinylated cRNA was cleaned up using Qiagen RNeasy kit, cat No. 74103. The RNeasy kit protocol was followed exactly. RNA was eluted in 2 aliquots of 30 µl DEPC treated H$_2$O. The RNA was precipitated by addition of 6 µl 3M sodium acetate pH 5.5 plus 75 µl absolute ethanol. The RNA was allowed to precipitate overnight at −20° C. Samples were centrifuged in a microfuge at 13,000 rpm for 20 minutes to pellet the RNA. The supernatant fraction was discarded and the pellet was washed in 1 ml of 75% ethanol and then allowed to air dry. The pellet was then resuspended in 20 µl DEPC treated H$_2$O. The yield of cRNA was ~40 µg for each sample.

cRNA Fragmentation

11 µg of cRNA was fragmented. 8 µl of 5× Fragmentation buffer (200 mM Tris-Acetate pH 8.1, 500 mM potassium acetate, 150 mM magnesium acetate) plus 11 µg cRNA made up to 20 µl with DEPC treated H$_2$O was used. The reaction mixture was incubated 94° C. for 35 minutes in a Perkin Elmer PE9600 thermal cycler.

Hybridization to GeneChip Microarray

The hybridization mix comprised: 20 µl (11 µg) of fragmented cRNA; 2.2 µl of control oligo B2 (50 pmol/µl) (sequence: 5'Biotin-GTCAAGATGCTACCGTTCAG 3'HPLC purified) (SEQ ID NO:16); 2.2 µl Herring Sperm DNA (10 mg/ml); 110 µl 2× Buffer (2M NaCl, 20 mM Tris pH 7.6, 0.01% Triton X-100); and 85.6 µl DEPC treated H$_2$O. The hybridization mix heated to 95° C. in a Techne hot block for 5 minutes, followed by incubation at 40° C. for 5 minutes. The hybridization mix was clarified by centrifugation in microfuge at 13,000 rpm for 5 minutes.

200 µl of supernatant to added to the GeneChip cartridge (GeneChip cartridge was previously pre-wetted with 200 µl 1× Buffer and incubated for 10 minutes at 40° C. in the rotisserie box of a GeneChip hybridization oven 320 (cat No. 800127) at maximum rpm. The sample was hybridized to the microarray overnight at 40° C. in a GeneChip hybridization oven in the rotisserie at maximum rpm.

Washing and Staining of Probe Arrays

The hybridization mix was recovered from the GeneChip cartridge and put back in the tube containing the remainder of the sample. 200 µl 6×SSPE-T (6×SSPE plus 0.005% Triton X-100) was applied to the chip and pipetted in and out twice. This process was repeated twice more. Another 200 µl 6×SSPE-T was applied to the cartridge and the cartridge was then incubated for 1 hour at 50° C. at maximum rpm in the GeneChip hybridization oven. The 6×SSPE-T was removed and 200 µl 0.5×SSPE-T was added to cartridge. The cartridge was incubated for 15 minutes at 50° C. at maximum rpm in the GeneChip hybridization oven. The 0.5×SSPE-T was removed and the cartridge was re-filled with 200 µl 6×SSPE-T.

The stain solution comprised: 190 µl 6×SSPE-T; 10 µl of 20 mg/ml acetylated BSA; and 2 µl 1 mg/ml conjugated streptavidin:phycoerythrin (Molecular Probes cat. No. S-866). 200 µl 6×SSPE-T was removed from the GeneChip cartridge and 200 µl of stain solution added. The cartridge was incubated at ambient temperature in a GeneChip hybridization oven at maximum rpm in the rotisserie for 10 minutes. The stain solution was removed and the cartridge was washed by adding 200 µl 6×SSPE-T and pipetting this in and out of the cartridge twice. This process was repeated six times. The cartridges were then completely filled with 6×SSPE-T and any bubbles removed. Hybridization, washing and staining was repeated using the same hybridization mixes until both samples had been hybridized to each of the four yeast chip sub-set arrays.

Data Collection

Data was collected by scanning the hybridized chips on a Hewlett-Packard GeneArray scanner. A "halo" effect (appearance of stain non-specifically across the array image) was seen on one of the scanned images: yeast growing in glucose rich media, sub-set C array. Scanning of this array was aborted after one scan and the chip was washed twice with 200 µl 6×SSPE-T and then re-filled as before. This array was then re-scanned three times and the data collected was the average of these three scans. All other arrays were scanned four times without problems and the data collected was the average of the four scans.

EXAMPLE 3

Isolation of Promoters and Construction of Expression Vectors.

PCR Amplification of Promoter Regions from Genomic DNA

Based on the *Saccharomyces cerevisiae* genomic sequence in the GenEMBL nucleotide database oligonucleotide primers were designed to amplify the genomic sequence 5' to the following ORFs: YLR110C (Johnston et al. (1997) Nature 1997 May 29;387(6632 Suppl):87-90), YMR251WA (common name HOR7) (Bowman et al. (1997) Nature May 29;387(6632 Suppl):90-3), YMR107W (Bowman et al. (1997) Nature May 29;387(6632 Suppl):90-3), and YOL109W (common name ZEO1) (Dujon et al. (1997) Nature May 29;387(6632 Suppl):98-102). The region amplified was the non-coding region separating the selected ORF and the next predicted *Saccharomyces cerevisiae* ORF in the 5' direction, with a minimum length of 500 bp.

Sequence of Oligonucleotide Primers used to Amplify Promoter DNA

HindIII, NheI and NdeI Cloning Sites Underlined.

| YLR110C-F | ATGC<u>AAGCTT</u>CGCGGCCGCCGTCTGATTTCCGTTT | SEQ ID NO:5 |
| YLR110C-R | CCAGGCCG<u>CATATG</u>TCATATAGTGTTTAAG | SEQ ID NO:6 |
| YMR251WA-F | AGCT<u>AAGCTT</u>CGCGGCCGCCTTTCGATTAGCACGCAC | SEQ ID NO:7 |
| YMR251WA-R | AGATACCTT<u>CATATG</u>TTATTATTAGTC | SEQ ID NO:8 |

```
YMR107W-F    AGCTAAGCTTCGCGGCCGCGCAGAAATGATGAAGG    SEQ ID NO:9
YMR107W-R    ATCCATCCCATATGTGATATCTCGATTAG          SEQ ID NO:10

ZEO1-F       AGCTAAGCTTCGCGGCCGCGGAGGTCTGCTTCACG    SEQ ID NO:11
ZEO1-R       TACGATCGCATATGTAATTGATATAAACG          SEQ ID NO:12
```

PCR reactions were set up for each primer pair as follows: For YMR251WA and ZEO1 90 µl of Reddy-Load PCR (1.1X) mix, 3.5 mM MgCl$_2$, (Advanced Biotechnologies, cat. no. AB-0628); 2 µl of forward primer (100 µM); 2 µl of reverse primer (100 µM); 1 µl of *S. cerevisiae* genomic DNA (Promega G310A, lot 8347702, 276 µg/ml); and 5 µl of H$_2$O were combined.

For YLR110C and YMR107W 90 µl of Reddy-Load PCR (1.1X) mix, 1.5 mM MgCl$_2$. (Advanced Biotechnologies, cat. no. AB-0575); 2 µl of forward primer (100 µM); 2 µl of reverse primer (100 µM); 1 µl of *S. cerevisiae* genomic DNA (Promega G310A, lot 8347702, 276 µg/ml); and 5 µl of H$_2$O were combined.

The thermocycling was carried out as follows: For the YMR251WA promoter: 94° C. for 5 minutes followed by 30 cycles of: 94° C. for 30 seconds, 60° C. for 30 seconds, 72° C. for 1 minute; followed by 72° C. for 5 minutes. The reaction mixtures were then held at 4° C. For the YMR107W and ZEO1 promoters: 94° C. for 5 minutes followed by 30 cycles of: 94° C. for 30 seconds, 45° C. for 30 seconds, 72° C. for 1 minute; followed by 72° C. for 5 minutes. The reaction mixtures were then held at 4° C. For the YLR110C promoter: 94° C. for 5 minutes followed by 30 cycles of: 94° C. for 30 seconds, 50° C. for 30 seconds, 72° C. for 1 minute; followed by 72° C. for 5 minutes. The reaction mixtures were then held at 4° C.

The PCR solutions were loaded onto an LMP gel and the bands were purified using Wizard PCR preps (Promega, cat. no. A7170) according to protocol, eluted in 50 µl, ethanol precipitated, and resuspended in 20 µl. A map of the YLR110C promoter region is shown in FIG. 13 and SEQ ID NO:29. A map of the YMR251WA promoter region is shown in FIG. 14 and SEQ ID NO:30. A map of the YMR107W promoter region is shown in FIG. 15 and SEQ ID NO:31. A map of the ZEO1 promoter region is shown in FIG. 16 and SEQ ID NO:32.

Cloning Promoter Regions into a Yeast Vector Containing Tile Luciferase Gene

Figure 2:
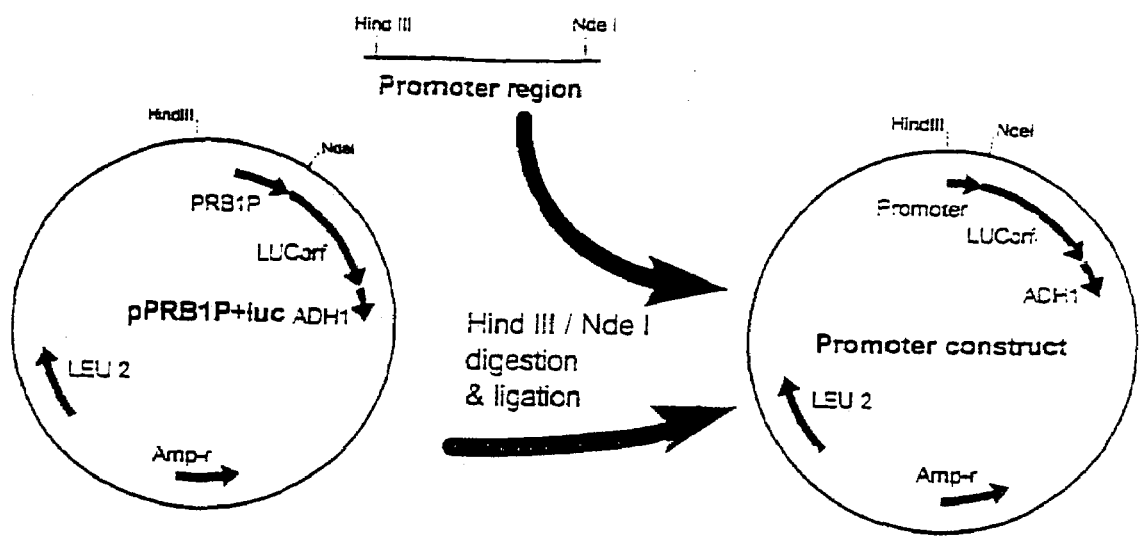
FIG. 2 schematically illustrates construction of YLR110C and YMR251WA promoter constructs.
Figure 3:
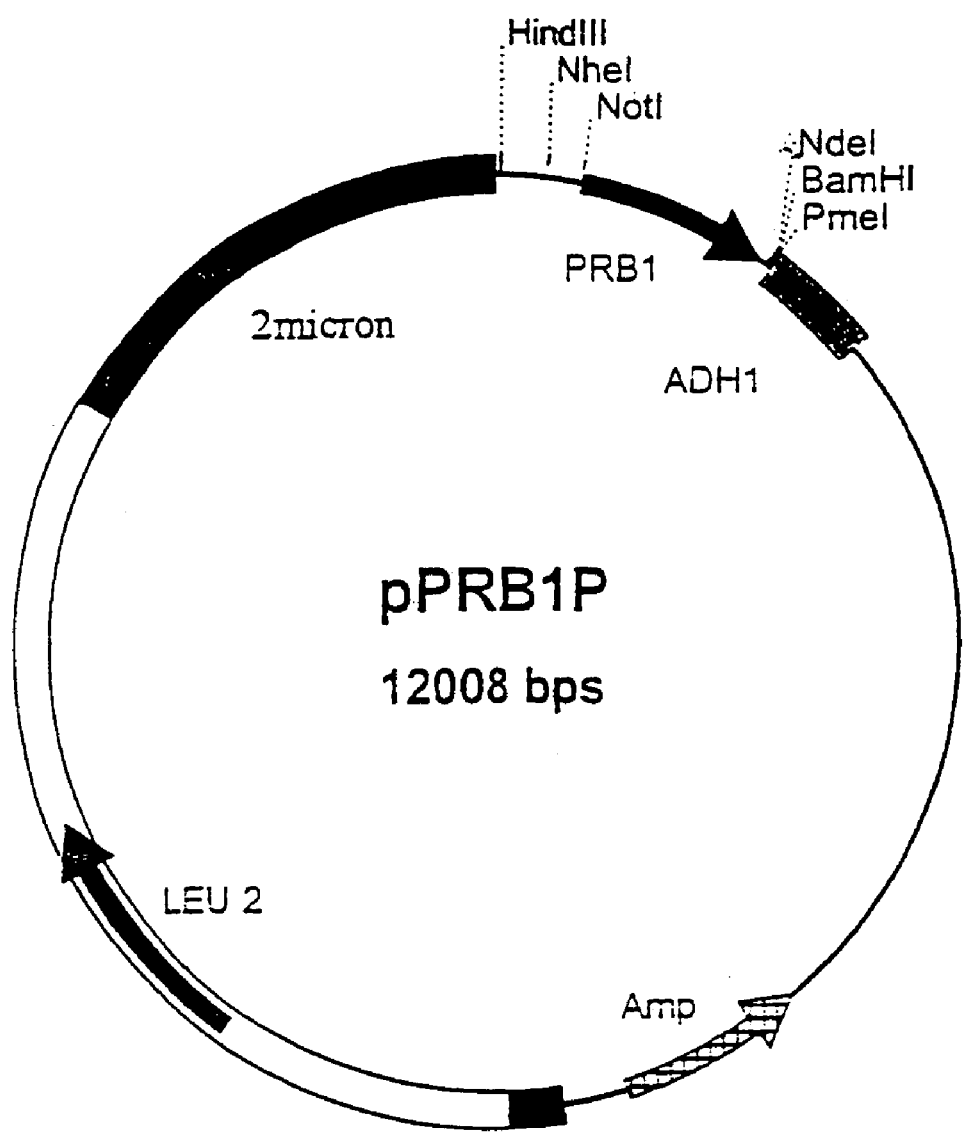
FIG. 3 is a map of pPRB1P.
Figure 4:
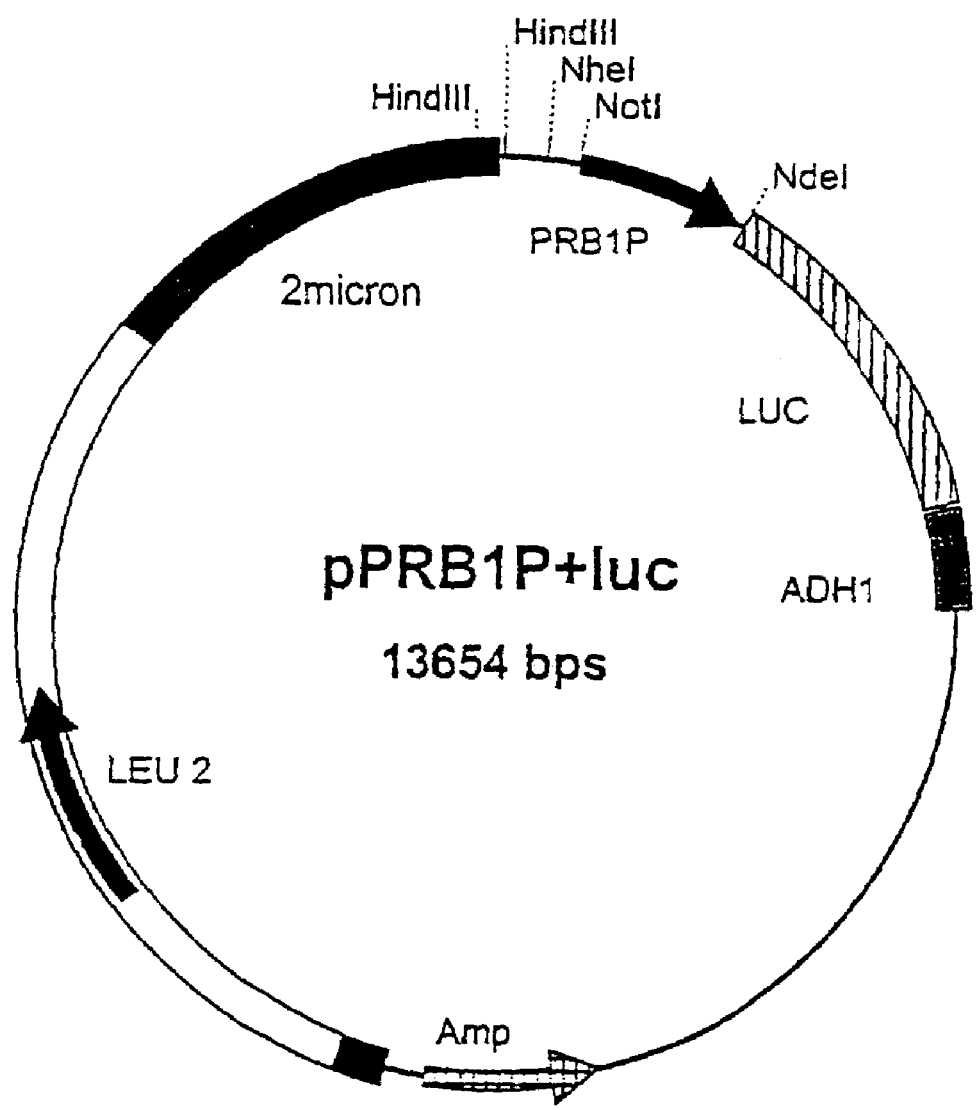
FIG. 4 is a map of pPRB1P+luc.
Figure 5:
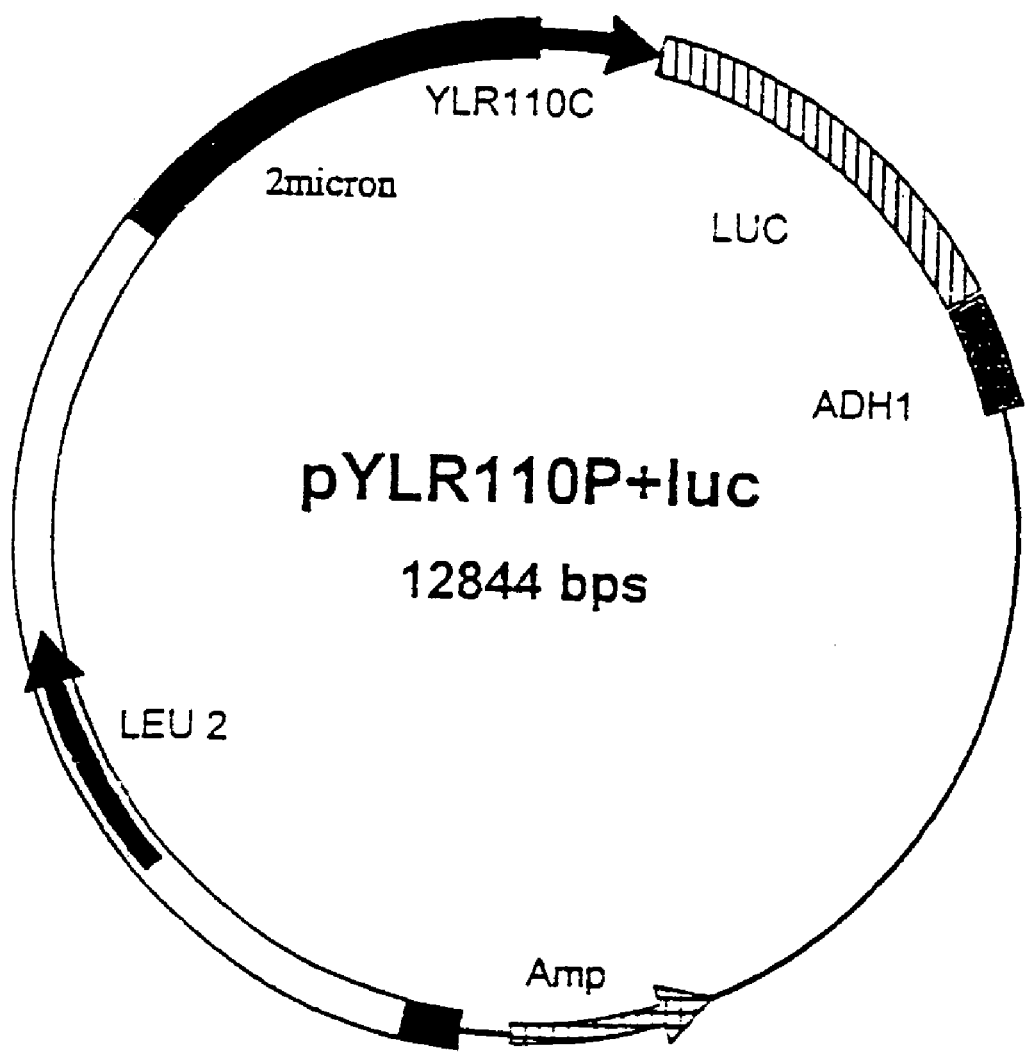
FIG. 5 is a map of pYLR110P+luc.
Figure 6:
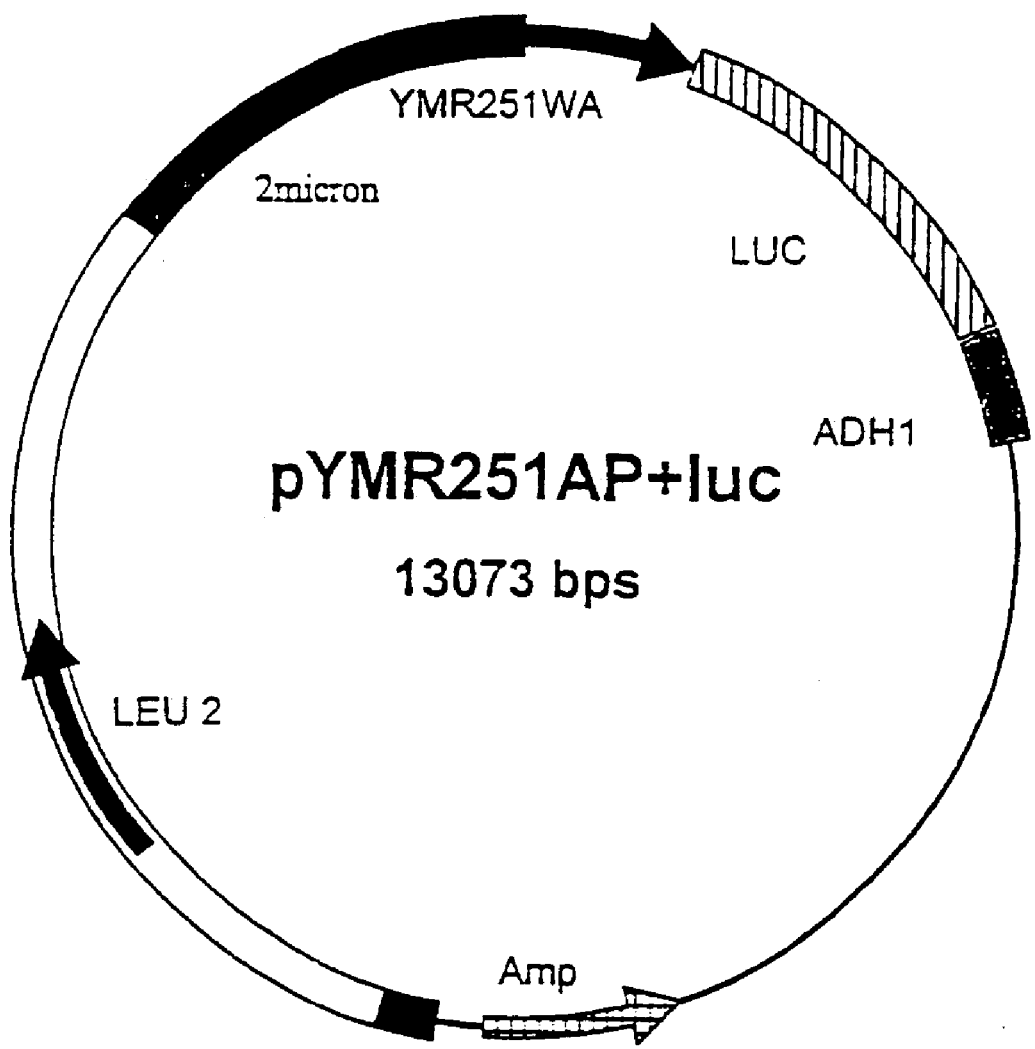
FIG. 6 is a is a map of pYMR251AP+luc.
Figure 7:
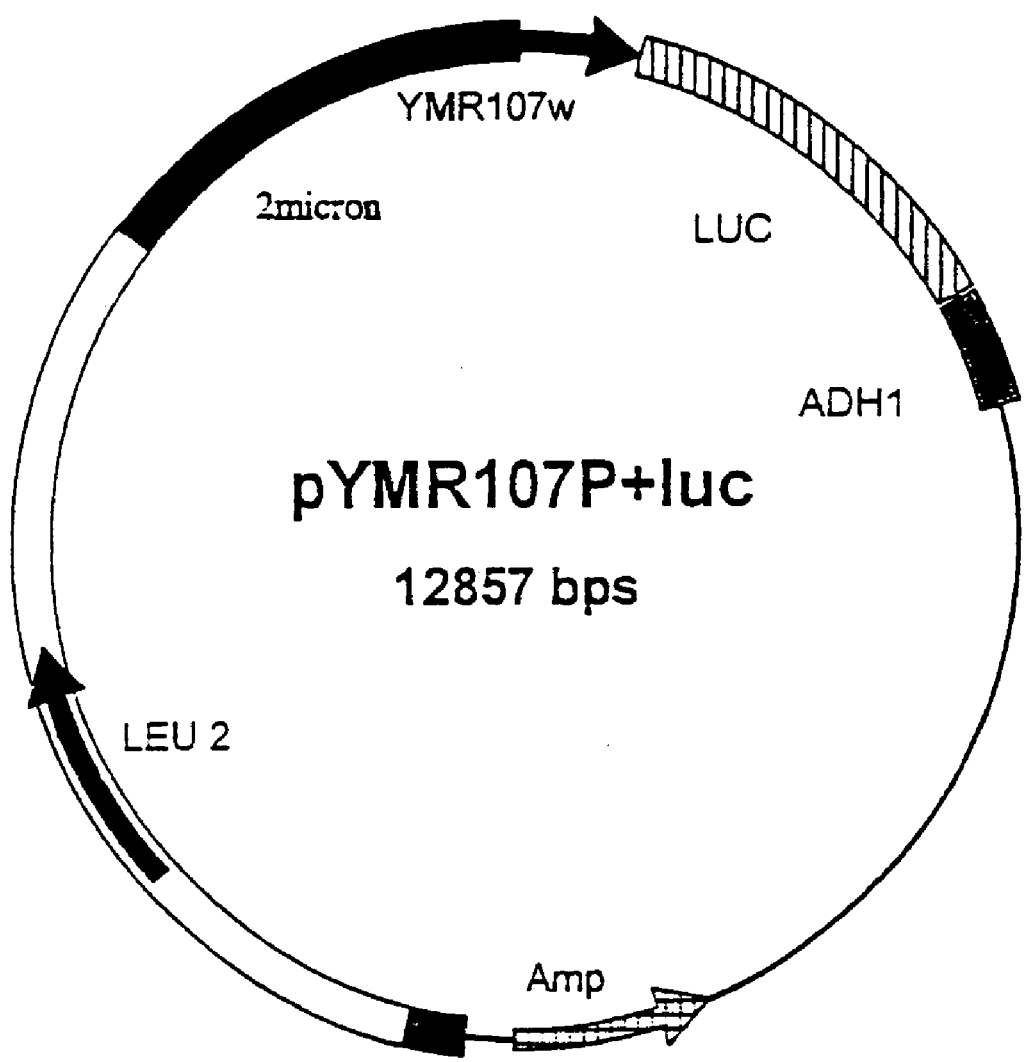
FIG. 7 is a map of pYMR107P+luc.
Figure 8:
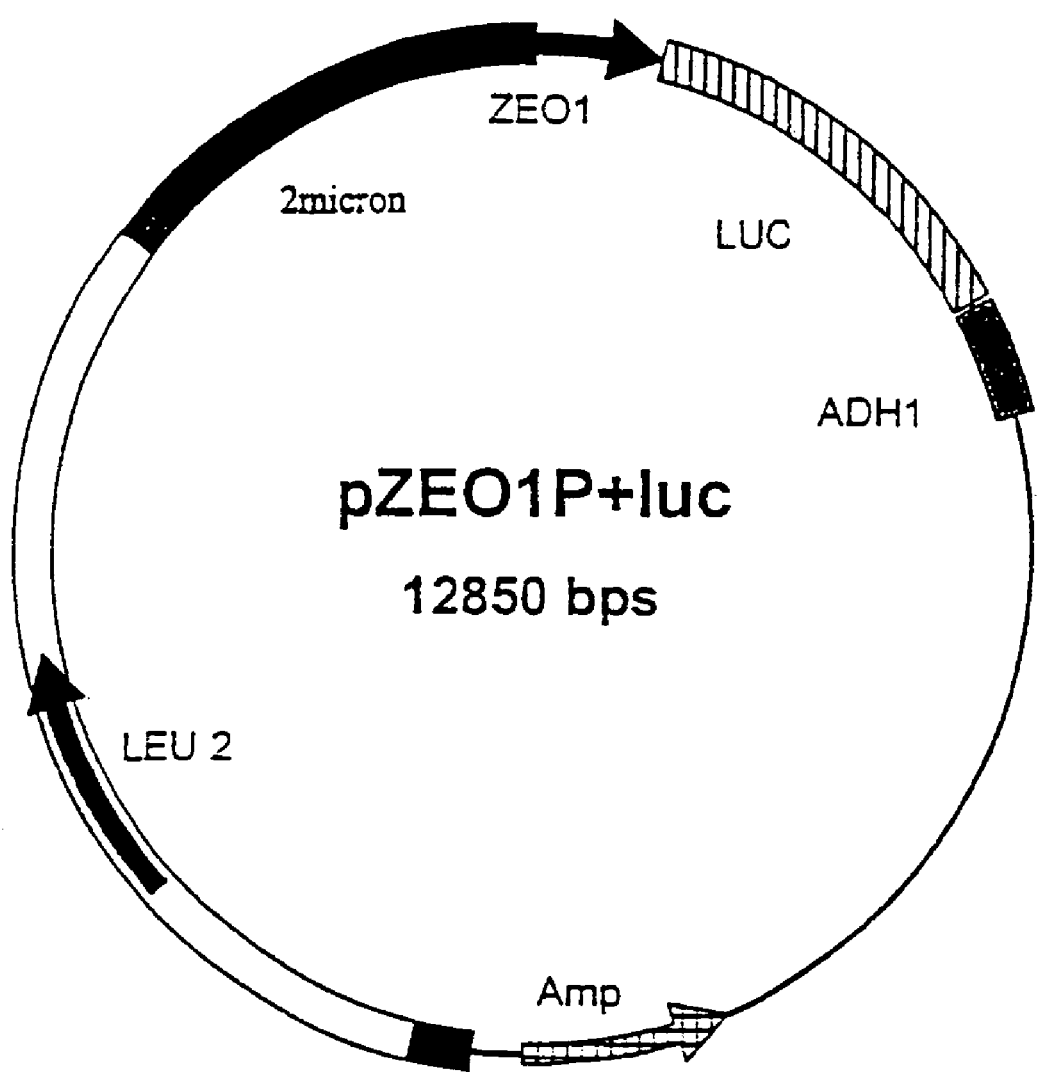
FIG. 8 is a map of pZEO1P+luc.

The PCR products representing the regions upstream of the YLR110C and YMR251WA ORFs were cloned into the suitably digested YEp13-based multicopy yeast expression vector pPRB1P+luc. A map of YEp13 is shown in FIG. 1. The Accession number for YEp13 is U03498. A map of pPRB1P is shown in FIG. 2. The sequence of pPRB1P is shown in SEQ ID NO:27. A map of pPRB1P+luc is shown in FIG. 3 and the sequence is shown in SEQ ID NO:28. The PRB1 promoter was removed from the vector by digesting with the restriction enzymes HindIII and NdeI. The digested backbone was then ligated with a HindIII/NdeI digested PCR product. See FIG. 4.

The PCR products described below, and maxi-prepped pPRB1P+luc were digested as follows. 60 µl of pPRBP1+luc (328 µg/ml), 10 µl of HindIII (Life Technologies, cat. no. 15207-012, 10 units/µl), 10 µl NdeI (Amersham, cat. no. E0216Y, 20 units/µl), 10 µl NEBuffer 2 (NEB, cat. no. 007-2), and 10 µl of H$_2$O. 14 µl YLR110C, 2 µl of HindIII (Life Technologies, cat. no. 15207-012, 10 units/µl), 2 µl NdeI (Amersham, cat. no. E0216Y, 20 units/µl), and 2 µl NEBuffer 2 (NEB, cat. no. 007-2). 14 µl YMR251WA, 2 µl of HindIII (Life Technologies, cat. no. 15207-012, 10 units/µl), 2 µl NdeI (Amersham, cat. no. E0216Y, 20 units/µl), and 2 µl NEBuffer 2 (NEB, cat. no. 007-2). The solutions were allowed to react at 37° C., for 4 hours.

The double digested pPRB1P+luc backbone was purified on an LMP gel using Wizard PCR preps (Promega, cat. no. A7170), and then ethanol precipitated. The remaining digestion products were also ethanol precipitated. The pPBR1P+luc digests were resuspended in 60 µl of H$_2$O and the PCR product digests were resuspended in 20 µl.

Ligation reactions were then carried out between each promoter region and the digested pPRBP1+luc at 16° C. overnight. The PCR products representing the regions upstream of the following ORFs; YMR107W and ZEO1, were prepared, restricted, and ligated essentially as described above, however BCL restriction buffer B and different amounts of PCR product/volumes were used.

Transformation of Ligation Products into *E. coli*

The products of the ligations described above were transformed into *E. coli* (Invitrogen's One-Shot TOP10 Competent cells, cat. no. C4040-10) according to manufacturers protocol. In each case 5 µl of the ligation product was added to the cell suspension. The total final cell suspension was plated out onto L-amp plates and incubated overnight at 37° C.

Colonies were picked from the plates and PCR screened using the PCR primers used to amplify the promoters originally. Two positive colonies from each ligation were grown in 5 ml overnight cultures and their plasmids were purified (Promega Wizard Plus SV Mini-preps, cat. no. A1330). The eluted DNA was ethanol precipitated and resuspended in 20 µl of water. Analytical restriction digests were carried out to confirm the presence of the correct promoter. Clones containing all four promoter constructs were obtained.

The new constructs were named as follows:
pPRB1+luc backbone+YLR110C promoter=pYLR110P+luc SEQ ID NO:19
pPRB1+luc backbone+YMR251WA promoter=pYMR251AP+luc SEQ ID NO:20
pPRB1+luc backbone+YMR107W promoter=pYMR107P+luc SEQ ID NO:21
pPRB1+luc backbone+ZEO1 promoter=pZEO1P+luc SEQ ID NO:22

Maps of pYLR110P+luc, pYMR251AP+luc, pYMR107P+luc, and pZEO1P+luc are shown in FIGS. 5, 6, 7, and 8, respectively. Plasmid DNA (pYLR110P+luc and pYMR251AP+luc) was prepared for transformation into yeast and sequencing using the QIAGEN Plasmid Maxi kit (cat. no. 12162). The DNA concentrations of the maxi-preps (measured by absorbance at 260 nm) were: pYLR110P+luc 463 µg/ml; pYMR251AP+luc 346 µg/ml; pYMR107P+luc ~300 µg/ml; and pZEO1P+luc ~720 µg/ml. The remaining plasmids were transformed into yeast as Wizard Plus SV Mini-prep DNA, and maxi-prep DNA was obtained for sequencing using the Gibco BRL Concert Plasmid Maxi kit (Cat no. 11452).

Sequencing of Promoter Constructs

DNA of each of the four promoter constructs were sequenced using the ABI PRISM BigDye Terminator Cycle Sequencing Kit (PE Applied Biosystems, part no. 4303153) was used to carry out the sequencing reactions. Each reaction contained 8 μl of Reaction Mix and 1 μl of 3.2 μM primer. The volumes of template DNA and H$_2$O added are as follows: 1.1 μl of pYLR110P+luc template and 9.9 μl of water; 1.4 μl of pYMR251AP+luc template and 9.6 μl of water; 2.0-6.0 μl of pYMR107P+luc template and 9.0-5.0 μl of water; and 0.5-1.5 μl of pZEO1P+luc template and 10.5-9.5 μl of water.

The thermocycling protocol is described in the ABI protocol, the PCR products were ethanol precipitated by adding 3M NaOAc and absolute Ethanol, standing at room temperature for 15 minutes, centrifuging for 20 minutes and washing with 250 μl of 70% ethanol. The precipitated DNA was resuspended in 3 μl of loading dye and 2 μl of each suspension was analyzed on an PE-ABI 377 automated sequencer.

The following promoter constructs pYLR110P+luc and pYMR251AP+luc were each sequenced using four primers:

YEp13 F2: CCTCAATTGGATTAGTCTCA—SEQ ID NO:13-aligns to the YEp13 backbone, 290 bp 5' of the Hind III site.

Luc R1: CACCTCGATATGTGCATCTG—SEQ ID NO:14-aligns to the Luc ORF, 150 bp 3' of the NdeI site.

Forward PCR primer: forward primer used to PCR clone promoter, i.e., SEQ ID NO:5 and SEQ ID NO: 7.

Reverse PCR primer: reverse primer used to PCR clone promoter, i.e., SEQ ID NO:6 and SEQ ID NO:8.

The remaining promoter constructs (pYMR107P+luc and pZEO1P+luc) were each sequenced using primers Yep13 F2 and Luc R1. Combining the data from all primers completely sequenced the promoter regions and spanned the cloning sites of the original vector.

Deviations from Published Genomic Sequences

All sequences differ by a few base pairs around the ATG, this results from the creation of an NdeI site at the 3' end of the promoter. In addition, the following further alterations from published sequences were identified.

pYLR110P+luc: A substitution of a C for a T had taken place at a base pair 361 of the sequence.

pYMR107P+luc: In the initial construct (for which luciferase reporter data is described), a cloning artifact led to the junction between the promoter region and the LUC ORF in pYMR107W+luc to have the sequence: CATAT<u>ATG</u> (where ATG is the luciferase translational start site). This sequence was modified by site directed mutagenesis to create the sequence CAT<u>ATG</u>, which generates a novel NdeI site at the promoter/luciferase junction. Subsequent luciferase expression analysis confirmed that expression from the NdeI site modified pYMR107P+luc construct did not differ significantly from the original construct, therefore the sequence of the corrected CAT<u>ATG</u> construct is included herein.

Other Modifications pYMR107P+luc: Cloning artifacts created an additional HindIII site and linker to the 5' (i.e. outside) of the pYMR107P+luc and promoters:

Instead of:

```
    hindIII   NotI     promoter 5'
    AAGCTT-CGCGGCCGCG-NNNNNNN         SEQ ID NO:17
```

The sequence is:

```
                                              SEQ ID NO:18
    hindIII  hindIII   NotI     promoter 5'
    AAGCTT-AGCT-AAGCTT-CGCGGCCGCTG-NNNNNNN.
```

EXAMPLE 4

Luciferase Assays of Promoter Activity

Transformation of *S. cerevisiae* with Promoter Constructs.

*S. cerevisiae* strain 11C was transformed with five promoter constructs. This strain carries six metabolic markers, Ade, Trp, Ura, Lys, Leu and His. It has the genotype: ade2-161, trp1-D63, ura3-52, lys2-801, leu2D1 &/or leu2-3 &/or leu2-112, hisD200 &/or hisD200. 11C was generated by crossing the strains YPH500 (Mat a ura3-52 lys2-801 ade2-161 trp1-D63 hisD200 leu2D1) and AH22 (MATa leu2-3 leu2-112 his4-519 can1.

11C cells were streaked from a glycerol stock onto a YPD plate and grown at 30° C. for two days. The cells were transformed with the five plasmids, pYLR110P+luc, pYMR251AP+luc, pYMR107P+luc, & pZEO1P+luc and pPRB1P+luc to act as a control. The transformations were carried out using the Quick and Easy method (Gietz, R. D. and R. A. Woods, 1994, *Molecular Genetics of Yeast: Practical Approaches* pp. 121-134. 10 ml of plasmid was added to the transformation mix in each case. The whole transformation mixes were plated out onto -Leu plates and incubated at 30° C. for three days. Three individual colonies from each transformation plate were picked and used to inoculate 10 ml YPD cultures. The 10 ml cultures were incubated in an orbital shaker set to 200 rpm and 30° C. Cells were harvested from the cultures at two points. First, at a point at which the OD of the culture was close to 1.0, at which time a 4 ml sample was taken. Second, a 3 ml sample was taken after an incubation time of 45 hours. The ODs and incubation time of each sample is shown in Table 5. For all harvested samples, the cells were immediately spun down at 3000 rpm and 4° C., washed in 5 ml of dH$_2$O, repelleted and frozen at −20° C.

TABLE 5

| Plasmid | Clone number | OD at time of harvesting first 4 ml sample | Incubation time at harvesting of first sample (hours) | OD at time of harvesting second 3 ml sample |
|---|---|---|---|---|
| pPRB1P + luc | 7 | 0.98 | 24.5 | 4.80 |
|  | 8 | 0.68 | 28 | 5.56 |
|  | 9 | 1.15 | 28 | 5.66 |
| pYLR110P + luc | 8 | 1.12 | 28 | 5.50 |
|  | 9 | 0.46 | 28 | 4.38 |
|  | 10 | 1.16 | 24.5 | 5.51 |
| pYMR251AP + luc | 8 | 1.20 | 24.5 | 4.99 |
|  | 9 | 1.05 | 27 | 4.71 |
|  | 10 | 1.15 | 27 | 5.18 |
| pYMR107P + luc | 1 | 1.06 | 27 | 5.47 |
|  | 2 | 0.49 | 28.5 | 4.54 |
|  | 3 | 0.97 | 25.5 | 5.58 |
| pZEO1P + luc | 1 | 1.02 | 28.5 | 4.84 |
|  | 2 | 0.62 | 28.5 | 4.97 |
|  | 3 | 0.42 | 28.5 | 4.31 |

Analysis of Luciferase Activity

All of the samples were analyzed for luciferase activity, using the LucLite Luciferase Reporter Gene Assay Kit (Packard, cat.no 6016911). The cells were prepared by resuspending in PBS and diluting to a final concentration of $6\times10^6$ cells/ml. 100 ml of each cell suspension was pipetted into wells in duplicate on two 96 well plates, so that each well contained $6\times10^5$ cells. The plates were incubated at 30° C. for 10 minutes. 100 ml of a 1 in 2 dilution of reconstituted substrate was added to each well, and the plate was further incubated at room temperature for 10 minutes. The luminescence was then measured using the Packard TopCount. The luminescence readings obtained after 0.03 min are shown below in counts per second (CPS) in Table 6.

promoter was ligated and used to transform E. coli. Correct recombinants were screened for.

EXAMPLE 5

Isolation of Active Promoter Fragments

Operative fragments of the YLR110C, YMR251WA, YMR107W and ZEO1 promoters can be generated using restriction endonucleases, 5' or 3' deletion mutagenesis, PCR, site specific deletion, or a combination thereof. For

TABLE 6

| Plasmid | Clone number | First sample Readings | (CPS) | Average | Average | Second sample Readings | (CPS) | Average | Average |
|---|---|---|---|---|---|---|---|---|---|
| pPRB1P + luc | 7 | 35890 | 35690 | 35790 | 34898 | 20322 | 20975 | 20648 | 19867 |
|  | 8 | 25498 | 25276 | 25387 | 24495 | 52997 | 51778 | 52388 | 51607 |
|  | 9 | 24137 | 27797 | 25967 | 25075 | 49192 | 46971 | 48081 | 47300 |
| pYLR110P + luc | 8 | 52354 | 53618 | 52986 | 52094 | 41789 | 38904 | 40346 | 39565 |
|  | 9 | 105299 | 99776 | 102537 | 101645 | 85562 | 84468 | 85015 | 84234 |
|  | 10 | 107531 | 109226 | 108379 | 107486 | 22507 | 22436 | 22471 | 21690 |
| pYMR251AP + luc | 8 | 71993 | 69797 | 70895 | 70003 | 40869 | 40202 | 40536 | 39755 |
|  | 9 | 98853 | 98389 | 98621 | 97729 | 51159 | 49828 | 50493 | 49712 |
|  | 10 | 83210 | 87546 | 85378 | 84485 | 70091 | 74576 | 72334 | 71553 |
| pYMR107P + luc | 1 | 9046 | 8650 | 8848 | 6790 | 29413 | 28505 | 28959 | 28124 |
|  | 2 | 3996 | 4009 | 4002 | 1945 | 24391 | 23915 | 24153 | 23318 |
|  | 3 | 3018 | 3236 | 3127 | 1069 | 23866 | 23408 | 23637 | 22802 |
| pZEO1P + luc | 1 | 64137 | 63162 | 63649 | 61592 | 47469 | 45769 | 46619 | 45784 |
|  | 2 | 19579 | 18329 | 18954 | 16897 | 44910 | 42982 | 43946 | 43111 |
|  | 3 | 87572 | 90317 | 88944 | 86887 | 142414 | 142262 | 142338 | 141503 |

The results are summarized in Table 7.

TABLE 7

| Promoter | mRNA levels | Luciferase Expression Glucose | Luciferase Expression Ethanol |
|---|---|---|---|
| PRB1 | Ethanol Induced | 1.00 | 1.00 |
| YLR110C | Highly Ethanol and Glucose Induced | 3.03 | 1.22 |
| YMR251WA | Highly Ethanol and Glucose Induced | 2.92 | 1.35 |
| YMR107W | Ethanol Induced | 0.21 | 0.95 |
| ZEO1 | Very Highly Ethanol and Glucose Induced | 3.62 | 2.89 |

Three promoters give higher levels of expression than PRB1 at both ODs, these are: YLR110C, YMR251WA, and ZEO1. The promoter showing the greatest fold induction is YMR107W.

Creating Vectors with Promoters but without the Luciferase Gene

Figure 9:
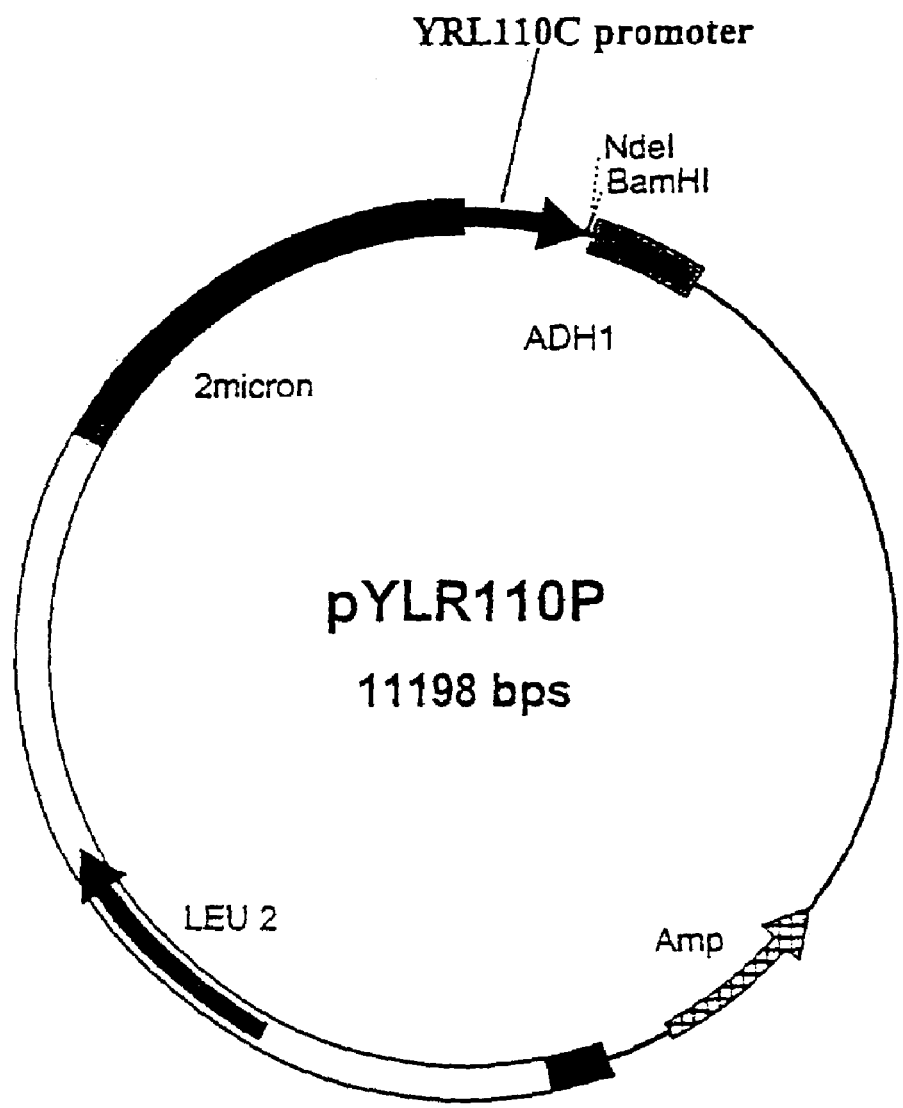
FIG. 9 is a map pYLR110P.
Figure 10:
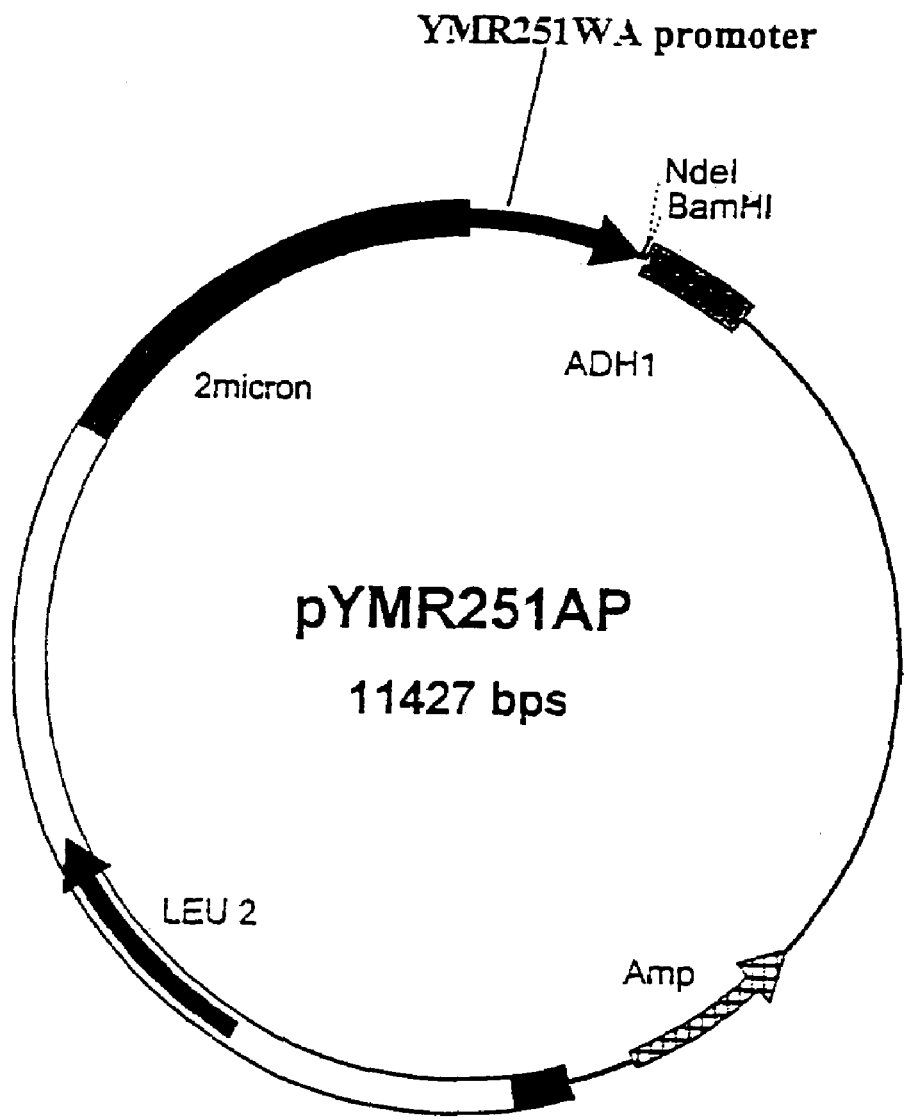
FIG. 10 is a map of pYMR251AP.
Figure 11:
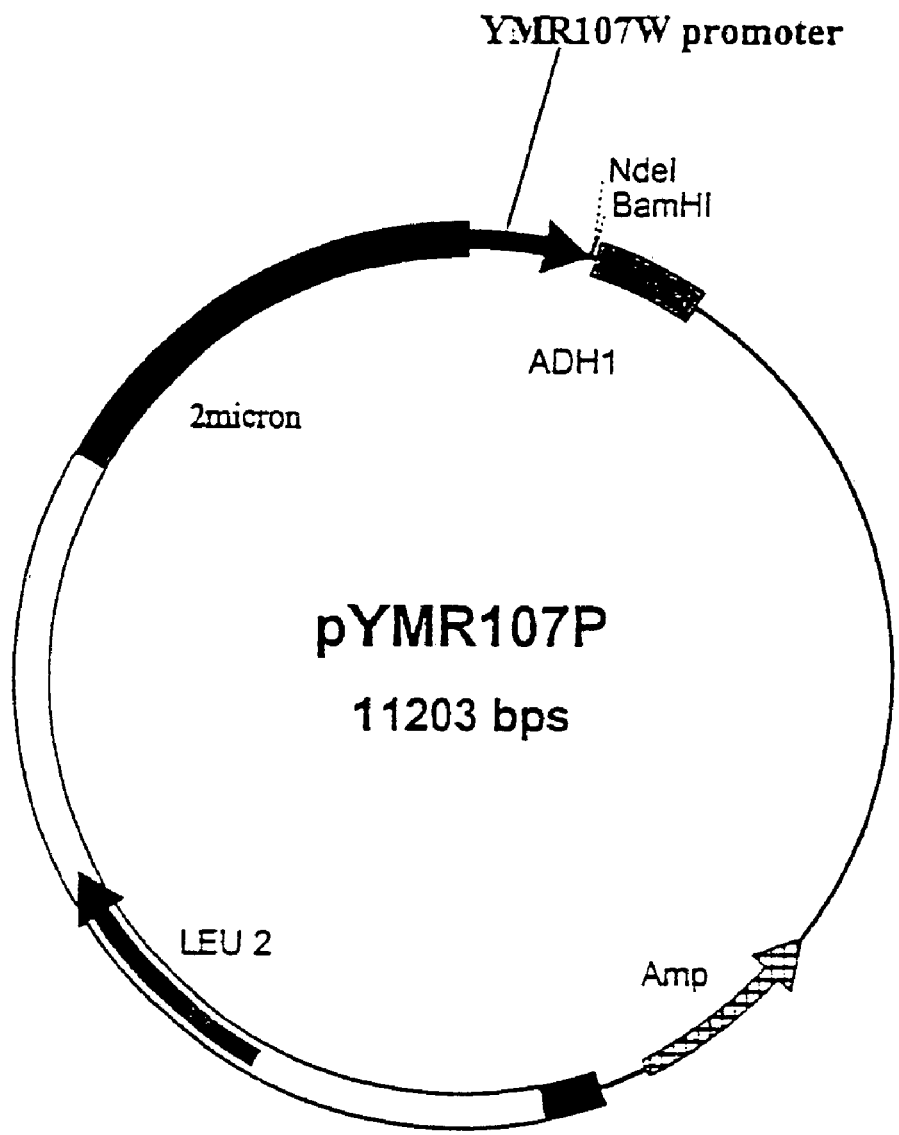
FIG. 11 is a map of pYMR107P.
Figure 12:
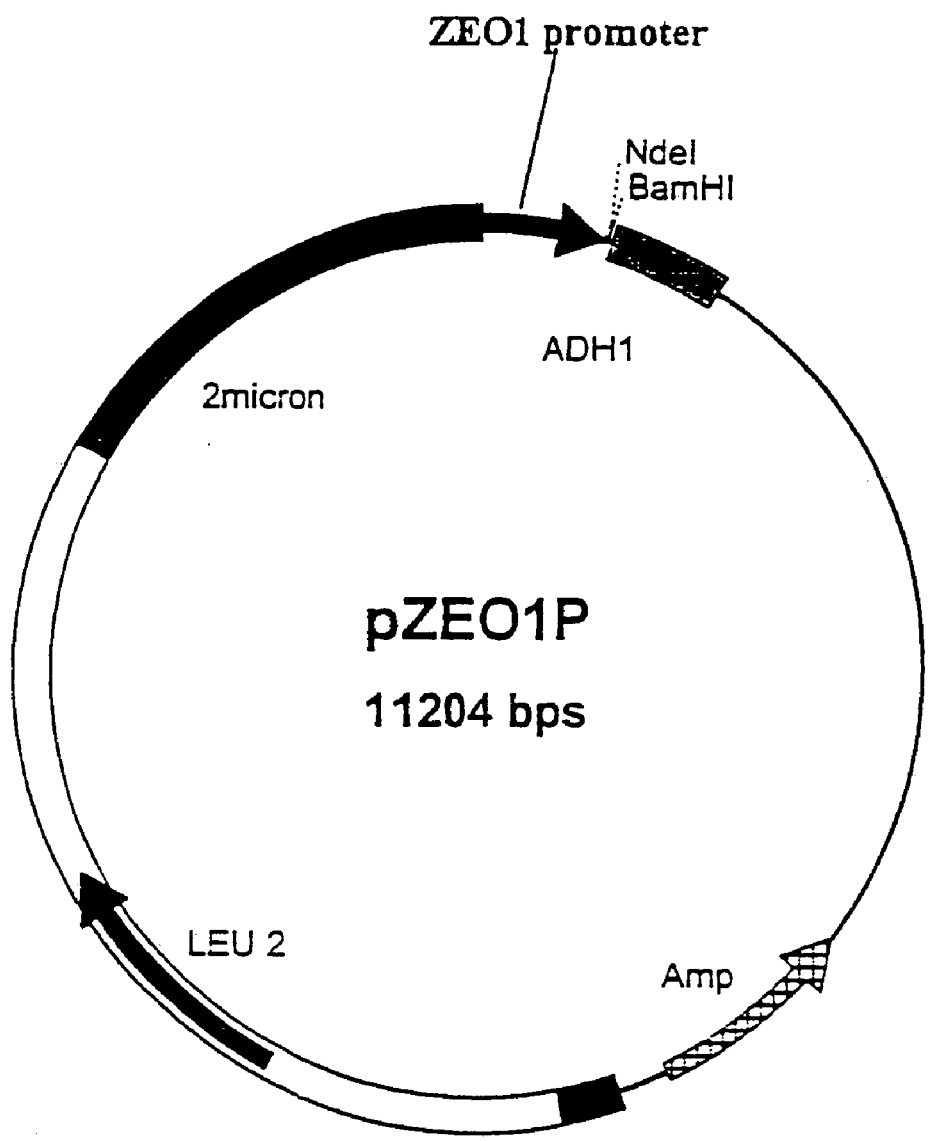
FIG. 12 is a map of pZEO1P.

Based on the analysis of luciferase expression four further promoter constructs have been made. The lack the luciferase gene and can be used to clone nucleic acid molecules encoding polypeptides of interest downstream of the promoters such that they drive expression of the nucleic molecules of interest. The sequences of these four plasmids are named: G1: pYLR110P (SEQ ID NO:23) (map at FIG. 9); G2: pYMR251AP (SEQ ID NO:24) (map at FIG. 10); G3 pYMR107P (SEQ ID NO:25) (map at FIG. 11); and G4: pZEO1P (SEQ ID NO:26) (map at FIG. 12). These were constructed by digesting pPRB1P (SEQ ID NO:27) with HindIII and NdeI to obtain the vector. The promoter+luc construct was digested with HindIII and NdeI to obtain the promoter fragment. The vector and promoter DNA was purified from LMP agarose using PCRpreps. The vector and example, purified pYLR110P+luc, pYMR251AP+luc, pYMR107P+luc or pZEO1P+luc plasmids, as generated in Example 3, can be subjected to restriction endonucleases to generate fragments of the YLR110C, YMR251WA, YMR107W or ZEO1 promoters. Restriction endonuclease sites, preferably unique restriction endonuclease sites, within the promoter sequences shown in SEQ ID NO:1, SEQ ID NO:2, SEQ ID NO:3, and SEQ ID NO:4 can be identified that generate fragments of the promoter upon restriction endonuclease digestion. Such fragments are preferably, 17, 25, 50, 75, 100, 150, 200, 250, 300, 350, 400, 450, 500, 550, 600, 650 or 700 nucleotides in length.

The fragments generated by restriction endonuclease digestion of the promoters shown in SEQ ID NO:1, SEQ ID NO:2, SEQ ID NO:3, or SEQ ID NO:4 can be separated by agarose gel electrophoresis. The agarose gel band corresponding to the desired promoter fragment can be cut out of the agarose gel. The fragment can be isolated and purified from the agarose gel by, for example, electroelution or kits such as QIAquick™ gel extraction kit or QIAEX® II Gel Extraction System (Qiagen Cat. No. 28704 and 20021).

The purified promoter fragment can be ligated into the isolated and purified HindIII, NdeI double-digested pPRBP1+luc backbone such that the promoter fragment is operably linked to a luciferase gene and transformed into E. coli, as described in Example 3. The new expression vector comprising a fragment of YLR110C, YMR251WA, YMR107W, or ZEO1 promoter region can be isolated and purified from E. coli, sequenced, and transformed into yeast as described in Example 3.

To analyze promoter activity, luciferase assays as described in Example 4, can be conducted using S. cerevisiae cultures that have been transformed with the expression vector comprising a fragment of the YLR110C, YMR251WA, YMR107W, or ZEO1 promoter operably linked to a luciferase gene and S. cerevisiae cultures that have been transformed with pPRB1P+luc. The *S. cerevisiae* cultures are grown in medium containing a non-fermentable carbon source, such as ethanol, or a fermentable carbon source, such as glucose, or both. Cells are obtained from the cultures and analyzed for luciferase activity as described in Example 4.

A promoter fragment is operative if it expresses at least 75% of the luciferase activity as the PRB1 promoter. Preferably, an operative promoter fragment expresses at least 100%, 200%, 300%, 400%, or more of the luciferase activity as the PRB1 promoter.

BRIEF DESCRIPTION OF THE SEQUENCES

SEQ ID NO:1 Polynucleotide sequence of promoter YLR110C
SEQ ID NO:2 Polynucleotide sequence of promoter YMR251WA
SEQ ID NO:3 Polynucleotide sequence of promoter YMR107W
SEQ ID NO:4 Polynucleotide sequence of promoter ZEO1
SEQ ID NO:5 Forward PCR primer for YLR110C
SEQ ID NO:6 Reverse PCR primer for YLR110C
SEQ ID NO:7 Forward PCR primer for YMR251WA
SEQ ID NO:8 Reverse PCR primer for YMR251WA
SEQ ID NO:9 Forward PCR primer for YMR107W
SEQ ID NO:10 Reverse PCR primer for YMR107W
SEQ ID NO:11 Forward PCR primer for ZEO1
SEQ ID NO:12 Reverse PCR primer for ZEO1
SEQ ID NO:13: Yep13 Forward PCR primer
SEQ ID NO:14: Luc RI Forward PCR primer
SEQ ID NO:15 Primer used in cDNA sequencing
SEQ ID NO:16 Control oligonucleotide used in GeneChip Microarray assay
SEQ ID NO:17 Original pYMR107P+luc sequence
SEQ ID NO:18 Modified pYMR107P+luc sequence
SEQ ID NO:19 Nucleotide sequence of pYLR110P+luc
SEQ ID NO:20 Nucleotide sequence of pYMR251AP+luc
SEQ ID NO:21 Nucleotide sequence of pYMR107P+luc
SEQ ID NO:22 Nucleotide sequence of pZEO1P+luc
SEQ ID NO:23 Nucleotide sequence of pYLR110P
SEQ ID NO:24 Nucleotide sequence of pYMR251AP
SEQ ID NO:25 Nucleotide sequence of pYMR107P
SEQ ID NO:26 Nucleotide sequence of pZEO1P
SEQ ID NO:27 Nucleotide sequence of pPRB1P
SEQ ID NO:28 Nucleotide sequence of pPRB1P+luc
SEQ ID NO:29 YLR110C promoter region
SEQ ID NO:30 YMR251WA promoter region
SEQ ID NO:31 YMR107W promoter region
SEQ ID NO:32 ZEO1 promoter region

We claim:

1. An isolated and purified polynucleotide consisting of SEQ ID NO:3 wherein the polynucleotide is operative as a promoter to express a nucleic acid molecule encoding a polypeptide when operably linked to said nucleic acid molecule.

2. A yeast expression vector comprising the polynucleotide of claim 1.

3. The yeast expression vector of claim 2 wherein the yeast expression vector is selected from the group consisting of pYMR107P+luc and pYMR107P.

4. A yeast cell transformed with the yeast expression vector of claim 2.

5. A yeast cell transformed with the yeast expression vector of claim 3.

6. A method for producing a polypeptide comprising the steps of:
   (a) constructing a yeast expression vector wherein the expression of a nucleic acid molecule encoding the polypeptide is controlled by the polynucleotide of claim 1;
   (b) transforming a culture of yeast cells with the yeast expression vector;
   (c) maintaining the yeast cells in culture so that the polypeptide is expressed; and
   (d) recovering the polypeptide.

7. A method for producing a polypeptide comprising the steps of:
   (a) cloning a nucleic acid molecule encoding the polypeptide into an expression vector selected from the group consisting of pYMR107P+luc and pYMR107P, wherein the nucleic acid molecule is operably linked to a promoter of the expression vector;
   (b) transforming a culture of yeast cells with the yeast expression vector;
   (c) maintaining the yeast cells in culture so that the polypeptide is expressed; and
   (d) recovering the polypeptide.

8. A method for producing a polypeptide comprising the steps of:
   (a) constructing a yeast expression vector wherein the expression of a nucleic acid molecule encoding the polypeptide is controlled by the polynucleotide of claim 1;
   (b) transforming a culture of yeast cells with the yeast expression vector;
   (c) maintaining the yeast cells in culture medium and controlling the expression of the nucleic acid molecule encoding the polypeptide by varying the level of a fermentable carbon source in the culture medium; and
   (d) recovering the polypeptide.

9. The method of claim 8 wherein the fermentable carbon source is glucose.

10. A method for producing a polypeptide comprising the steps of:
   (a) constructing a yeast expression vector wherein the expression of a nucleic acid molecule encoding the polypeptide is controlled by the polynucleotide of claim 1;
   (b) transforming a culture of yeast cells with the yeast expression vector;
   (c) maintaining the yeast cells in culture medium and controlling the expression of the nucleic acid molecule encoding the polypeptide by varying the level of a non-fermentable carbon source in the culture medium; and
   (d) recovering the polypeptide.

11. The method of claim 10 wherein the non-fermentable carbon source is ethanol.

12. A method for producing a polypeptide comprising the steps of:

(a) constructing a yeast expression vector wherein the expression of a nucleic acid molecule encoding the polypeptide is controlled by the polynucleotide of claim 1;

(b) transforming a culture of yeast cells with the yeast expression vector;

(c) maintaining the yeast cells in culture medium and controlling the expression of the nucleic acid molecule encoding the polypeptide by varying the level of a fermentable carbon source and a non-fermentable carbon source in the culture medium; and (d) recovering the polypeptide.

13. The method of claim 12 wherein the fermentable carbon source is glucose.

14. The method of claim 12 wherein the non-fermentable carbon source is ethanol.

15. A method of identifying a promoter fragment, wherein the fragment has promoter activity comprising the steps of:

(a) generating a fragment comprising at least 17 contiguous nucleotides of an isolated and purified polynucleotide which is SEQ ID NO:3;

(b) cloning the fragment into a yeast expression vector, wherein the fragment is operably linked to a reporter gene;

(c) transforming yeast cells with the yeast expression vector;

(d) growing the yeast cells in yeast cell culture under conditions favorable for expression of the reporter gene; and (e) assaying the yeast culture for a reporter protein expressed by the reporter gene;

wherein expression of the reporter gene indicates the fragment has promoter activity.

* * * * *